United States Patent
McDonnell

(10) Patent No.: US 9,907,593 B2
(45) Date of Patent: *Mar. 6, 2018

(54) WOVEN RETENTION DEVICES, SYSTEMS AND METHODS

(71) Applicant: Woven Orthopedic Technologies, LLC, Manchester, CT (US)

(72) Inventor: Christopher McDonnell, Sandy Hook, CT (US)

(73) Assignee: WOVEN ORTHOPEDIC TECHNOLOGIES, LLC, Manchester, CT (US)

( * ) Notice: Subject to any disclaimer, the term of this patent is extended or adjusted under 35 U.S.C. 154(b) by 343 days.

This patent is subject to a terminal disclaimer.

(21) Appl. No.: 14/569,542

(22) Filed: Dec. 12, 2014

(65) Prior Publication Data

US 2016/0038206 A1    Feb. 11, 2016

Related U.S. Application Data

(60) Provisional application No. 62/033,455, filed on Aug. 5, 2014.

(51) Int. Cl.
*A61B 17/84* (2006.01)
*A61B 17/86* (2006.01)
*A61B 17/68* (2006.01)

(52) U.S. Cl.
CPC .......... *A61B 17/869* (2013.01); *A61B 17/686* (2013.01); *A61B 17/86* (2013.01); *A61B 2017/8655* (2013.01)

(58) Field of Classification Search
CPC ..... A61B 17/84; A61B 17/686; A61B 17/869; A61B 2017/8655; A61B 17/86; A61B 17/8625; A61B 17/8685

See application file for complete search history.

(56) References Cited

U.S. PATENT DOCUMENTS

| 517,668 A | 4/1894 | Still |
|---|---|---|
| 1,486,527 A | 3/1924 | Larkin |

(Continued)

FOREIGN PATENT DOCUMENTS

| CN | 201046258 Y | 4/2008 |
|---|---|---|
| EP | 1614402 A1 | 1/2006 |

(Continued)

OTHER PUBLICATIONS

International Search Report and Written Opinion in International Application No. PCT/US2015/043471, dated Nov. 3, 2015.

(Continued)

*Primary Examiner* — Samuel Hanna

(74) *Attorney, Agent, or Firm* — Venable LLP; Michael V. Frank

(57) ABSTRACT

A woven retention device for interfacing with a bone surface is provided that includes a sleeve body that can surround a fastener, a proximal end for receiving the fastener, and a distal end. The sleeve body includes interwoven monofilaments of different diameters forming a substantially tubular lattice with protuberances distributed on interior and exterior surfaces of the lattice at a predetermined spatial relationship. In a first state, the sleeve body has a plurality of combinations of filament cross-section geometries at the intersection points, forming a plurality of protuberance thicknesses as measured in a radial direction of the sleeve body. In a second state when a fastener is inserted into the tubular lattice, pressure from the fastener is transmitted to the tubular lattice such that the spatial relationship of the protuberances changes according to a function of bone density and an interfacing surface shape of the fastener.

35 Claims, 38 Drawing Sheets

(56) References Cited

U.S. PATENT DOCUMENTS

| | | |
|---|---|---|
| 1,516,652 A | 11/1924 | Tomkinson |
| 2,148,164 A | 2/1939 | Krippendorf |
| 2,326,453 A | 8/1943 | Gelpcke |
| 2,388,693 A | 11/1945 | Jeckel |
| 2,879,687 A | 3/1959 | Leimbach |
| 2,936,670 A | 5/1960 | Walter |
| 2,983,182 A | 5/1961 | Shobert |
| 3,054,406 A | 9/1962 | Francis |
| 3,187,752 A | 6/1965 | Glick |
| 3,199,398 A | 8/1965 | Weisz |
| 3,232,163 A | 2/1966 | George |
| 3,363,502 A | 1/1968 | Florentine |
| 3,371,573 A | 3/1968 | Koreki |
| 3,710,789 A | 1/1973 | Ersek |
| 3,714,862 A | 2/1973 | Berger |
| 3,921,496 A | 11/1975 | Helderman |
| 4,011,602 A | 3/1977 | Rybicki et al. |
| 4,064,567 A | 12/1977 | Burstein et al. |
| 4,158,984 A | 6/1979 | Griffiths |
| 4,182,339 A | 1/1980 | Hardy, Jr. |
| 4,205,399 A | 6/1980 | Shalaby et al. |
| 4,304,169 A | 12/1981 | Cimprich et al. |
| 4,383,527 A | 5/1983 | Asnis et al. |
| 4,394,370 A | 7/1983 | Jefferies |
| 4,409,974 A | 10/1983 | Freedland |
| 4,453,539 A | 6/1984 | Raftopoulos et al. |
| 4,520,821 A | 6/1985 | Schmidt et al. |
| 4,563,489 A | 1/1986 | Urist |
| 4,566,466 A | 1/1986 | Ripple et al. |
| 4,567,917 A | 2/1986 | Millard |
| 4,584,722 A | 4/1986 | Levy et al. |
| 4,610,688 A | 9/1986 | Silvestrini et al. |
| 4,640,271 A | 2/1987 | Lower |
| 4,708,132 A | 11/1987 | Silvestrini |
| 4,716,807 A | 1/1988 | Fischer |
| 4,753,149 A | 6/1988 | Celani |
| 4,760,843 A | 8/1988 | Fischer et al. |
| 4,777,860 A | 10/1988 | Bassett et al. |
| 4,790,852 A | 12/1988 | Noiles |
| 4,803,909 A | 2/1989 | Smith |
| 4,870,957 A | 10/1989 | Goble et al. |
| 4,894,063 A | 1/1990 | Nashef |
| 4,913,028 A | 4/1990 | Yoshiya |
| 5,013,318 A | 5/1991 | Spranza, III |
| 5,059,211 A | 10/1991 | Stack |
| 5,084,050 A | 1/1992 | Draenert |
| 5,171,148 A | 12/1992 | Wasserman et al. |
| 5,186,992 A | 2/1993 | Kite, III |
| 5,211,647 A | 5/1993 | Schmieding |
| 5,221,261 A | 6/1993 | Termin et al. |
| 5,257,571 A | 11/1993 | Richardson |
| 5,268,001 A | 12/1993 | Nicholson et al. |
| 5,300,075 A | 4/1994 | Gordon |
| 5,354,292 A | 10/1994 | Braeuer et al. |
| 5,380,334 A | 1/1995 | Torrie et al. |
| 5,383,387 A | 1/1995 | Chesterfield et al. |
| 5,385,077 A | 1/1995 | Akiyama et al. |
| 5,443,499 A | 8/1995 | Schmitt |
| 5,456,721 A | 10/1995 | Legrand |
| 5,458,601 A | 10/1995 | Young, Jr. et al. |
| 5,501,133 A | 3/1996 | Brookstein et al. |
| 5,520,084 A | 5/1996 | Chesterfield et al. |
| 5,571,184 A | 11/1996 | DeSatnick |
| 5,628,788 A | 5/1997 | Pinchuk |
| 5,629,077 A | 5/1997 | Turnlund et al. |
| 5,641,256 A | 6/1997 | Gundy |
| 5,713,904 A | 2/1998 | Errico et al. |
| 5,716,359 A | 2/1998 | Ojima et al. |
| 5,718,159 A | 2/1998 | Thompson |
| 5,725,541 A | 3/1998 | Anspach, III et al. |
| 5,741,325 A | 4/1998 | Chaikof et al. |
| 5,756,457 A | 5/1998 | Wang et al. |
| 5,758,562 A | 6/1998 | Thompson |
| 5,766,250 A | 6/1998 | Chervitz et al. |
| 5,785,713 A | 7/1998 | Jobe |
| D397,794 S | 9/1998 | Geber |
| 5,849,013 A | 12/1998 | Whittaker et al. |
| 5,871,504 A | 2/1999 | Eaton et al. |
| 5,876,432 A | 3/1999 | Lau et al. |
| 5,904,685 A | 5/1999 | Walawalkar |
| 5,941,901 A | 8/1999 | Egan |
| 5,957,974 A | 9/1999 | Thompson et al. |
| 5,961,524 A | 10/1999 | Crombie |
| 5,984,926 A | 11/1999 | Jones |
| 6,019,786 A | 2/2000 | Thompson |
| 6,039,740 A | 3/2000 | Olerud |
| 6,042,592 A | 3/2000 | Schmitt |
| 6,056,751 A | 5/2000 | Fenton, Jr. |
| 6,080,155 A | 6/2000 | Michelson |
| 6,099,530 A | 8/2000 | Simonian et al. |
| 6,126,663 A | 10/2000 | Hair |
| 6,143,029 A | 11/2000 | Rippstein |
| 6,231,606 B1 | 5/2001 | Graf et al. |
| 6,241,757 B1 | 6/2001 | An et al. |
| 6,264,676 B1 | 7/2001 | Gellman et al. |
| 6,314,856 B1 | 11/2001 | Keith et al. |
| 6,319,255 B1 | 11/2001 | Grundei et al. |
| 6,325,822 B1 | 12/2001 | Chouinard et al. |
| 6,336,940 B1 | 1/2002 | Graf et al. |
| 6,342,068 B1 | 1/2002 | Thompson |
| 6,355,044 B1 | 3/2002 | Hair |
| 6,375,662 B1 | 4/2002 | Schmitt |
| 6,398,807 B1 | 6/2002 | Chouinard et al. |
| 6,413,260 B1 | 7/2002 | Berrevoets et al. |
| 6,495,227 B1 | 12/2002 | Cahuzac |
| 6,500,203 B1 | 12/2002 | Thompson et al. |
| 6,540,770 B1 | 4/2003 | Tornier et al. |
| 6,544,281 B2 | 4/2003 | ElAttrache et al. |
| 6,551,352 B2 | 4/2003 | Clerc et al. |
| 6,582,461 B1 | 6/2003 | Burmeister et al. |
| 6,616,694 B1 | 9/2003 | Hart |
| 6,616,996 B1 | 9/2003 | Keith et al. |
| 6,622,604 B1 | 9/2003 | Chouinard et al. |
| 6,631,666 B2 | 10/2003 | Cahuzac |
| 6,645,211 B2 | 11/2003 | Magana |
| 6,652,571 B1 | 11/2003 | White et al. |
| 6,669,706 B2 | 12/2003 | Schmitt et al. |
| 6,685,738 B2 | 2/2004 | Chouinard et al. |
| 6,746,483 B1 | 6/2004 | Bojarski et al. |
| 6,767,350 B1 | 7/2004 | Lob |
| 6,792,979 B2 | 9/2004 | Konya et al. |
| 6,827,743 B2 | 12/2004 | Eisermann et al. |
| 6,840,769 B2 | 1/2005 | Augthun et al. |
| D503,802 S | 4/2005 | Bjarnason |
| 6,875,216 B2 | 4/2005 | Wolf |
| 6,908,466 B1 | 6/2005 | Bonutti et al. |
| 6,942,666 B2 | 9/2005 | Overaker et al. |
| 6,942,693 B2 | 9/2005 | Chouinard et al. |
| 6,991,647 B2 | 1/2006 | Jadhav |
| 7,004,967 B2 | 2/2006 | Chouinard et al. |
| 7,022,124 B2 | 4/2006 | Takei et al. |
| 7,052,513 B2 | 5/2006 | Thompson |
| 7,093,527 B2 | 8/2006 | Rapaport et al. |
| 7,101,183 B2 | 9/2006 | Augthun et al. |
| 7,213,495 B2 | 5/2007 | McCullagh et al. |
| 7,237,466 B2 | 7/2007 | Chen |
| 7,255,712 B1 | 8/2007 | Steinberg |
| 7,275,471 B2 | 10/2007 | Nishri et al. |
| 7,279,008 B2 | 10/2007 | Brown et al. |
| 7,309,355 B2 | 12/2007 | Donnelly et al. |
| 7,311,031 B2 | 12/2007 | McCullagh et al. |
| 7,341,592 B1 | 3/2008 | Walters et al. |
| 7,341,601 B2 | 3/2008 | Eisermann et al. |
| 7,344,559 B2 | 3/2008 | Gray et al. |
| 7,407,512 B2 | 8/2008 | Bojarski et al. |
| 7,435,254 B2 | 10/2008 | Chouinard et al. |
| 7,513,865 B2 | 4/2009 | Bourne et al. |
| 7,547,321 B2 | 6/2009 | Silvestri et al. |
| 7,572,283 B1 | 8/2009 | Meridew |
| 7,572,298 B2 | 8/2009 | Roller et al. |
| 7,582,108 B2 | 9/2009 | Hierlemann et al. |
| D612,499 S | 3/2010 | Ondracek et al. |
| 7,682,392 B2 | 3/2010 | Serhan et al. |
| 7,699,893 B2 | 4/2010 | Donnelly et al. |

(56) References Cited

U.S. PATENT DOCUMENTS

| | | |
|---|---|---|
| 7,731,750 B2 | 6/2010 | Bojarski et al. |
| 7,749,233 B2 | 7/2010 | Farr et al. |
| 7,758,642 B2 | 7/2010 | Bojarski et al. |
| 7,785,357 B2 | 8/2010 | Guan et al. |
| D626,648 S | 11/2010 | Ahlgren |
| 7,824,433 B2 | 11/2010 | Williams |
| 7,833,249 B2 | 11/2010 | Shaolian et al. |
| 7,892,203 B2 | 2/2011 | Lenker et al. |
| 7,896,901 B2 | 3/2011 | Whittaker |
| 7,938,853 B2 | 5/2011 | Chouinard et al. |
| 7,963,972 B2 | 6/2011 | Foerster et al. |
| 7,967,851 B2 | 6/2011 | Bickley et al. |
| 7,988,732 B2 | 8/2011 | Bojarski et al. |
| 8,052,720 B2 | 11/2011 | Kuester et al. |
| 8,114,141 B2 | 2/2012 | Appenzeller et al. |
| 8,128,626 B2 | 3/2012 | Justin |
| 8,142,415 B2 | 3/2012 | Warnock, Jr. et al. |
| 8,151,682 B2 | 4/2012 | Lilbum et al. |
| 8,162,998 B2 | 4/2012 | Schlienger et al. |
| 8,163,031 B2 | 4/2012 | Truckai et al. |
| 8,202,306 B2 | 6/2012 | Dreyfuss |
| 8,221,479 B2 | 7/2012 | Glazer et al. |
| 8,226,714 B2 | 7/2012 | Beck, Jr. et al. |
| 8,226,715 B2 | 7/2012 | Hwang et al. |
| 8,241,340 B2 | 8/2012 | Froehlich |
| 8,257,395 B2 | 9/2012 | Bhatnagar et al. |
| 8,298,262 B2 | 10/2012 | Stone et al. |
| 8,308,779 B2 | 11/2012 | Reiley |
| 8,317,799 B2 | 11/2012 | Schon et al. |
| 8,317,863 B2 | 11/2012 | Cauldwell et al. |
| 8,347,772 B2 | 1/2013 | Dow et al. |
| 8,353,941 B2 | 1/2013 | Fricker et al. |
| 8,361,078 B2 | 1/2013 | Beyar et al. |
| 8,366,711 B2 | 2/2013 | Rabiner et al. |
| 8,372,115 B2 | 2/2013 | Kohm et al. |
| 8,382,849 B2 | 2/2013 | Thomas |
| 8,414,635 B2 | 4/2013 | Hyodoh et al. |
| 8,420,113 B2 | 4/2013 | Zhao |
| 8,435,293 B2 | 5/2013 | Donnelly et al. |
| 8,443,706 B2 | 5/2013 | Egres, Jr. |
| 8,459,164 B2 | 6/2013 | Lilbum et al. |
| 8,523,902 B2 | 9/2013 | Heaven et al. |
| 8,523,916 B2 | 9/2013 | Anderson et al. |
| 8,523,951 B2 | 9/2013 | Kania |
| 8,545,499 B2 | 10/2013 | Lozier et al. |
| 8,546,456 B2 | 10/2013 | Rose et al. |
| 8,546,752 B2 | 10/2013 | Henion et al. |
| 8,568,413 B2 | 10/2013 | Mazur et al. |
| 8,585,762 B2 | 11/2013 | Hall |
| 8,591,582 B2 | 11/2013 | Anderson et al. |
| 8,617,185 B2 | 12/2013 | Bonutti et al. |
| 8,636,753 B2 | 1/2014 | Buevich et al. |
| 8,652,171 B2 | 2/2014 | Stone et al. |
| 8,663,296 B2 | 3/2014 | Williams |
| 8,663,672 B2 | 3/2014 | Manrique et al. |
| 8,671,815 B2 | 3/2014 | Hancock et al. |
| 8,677,874 B2 | 3/2014 | Lilbum et al. |
| 8,690,962 B2 | 4/2014 | Dignam et al. |
| 8,696,748 B2 | 4/2014 | Bojarski et al. |
| 8,709,055 B2 | 4/2014 | Beyar et al. |
| 8,721,519 B2 | 5/2014 | Sheu et al. |
| 8,747,470 B2 | 6/2014 | Beck, Jr. et al. |
| 8,753,391 B2 | 6/2014 | Lu et al. |
| 8,770,081 B2 | 7/2014 | David et al. |
| 8,794,118 B2 | 8/2014 | Dow et al. |
| 8,833,224 B2 | 9/2014 | Thompson et al. |
| 8,857,304 B2 | 10/2014 | Govari et al. |
| 8,910,554 B2 | 12/2014 | Kinugasa |
| D723,166 S | 2/2015 | Igaki et al. |
| 8,956,394 B1 | 2/2015 | McDonnell |
| 8,992,537 B1 | 3/2015 | McDonnell |
| 9,388,517 B2 | 7/2016 | Lilbum et al. |
| 9,416,472 B2 | 8/2016 | Scherrible et al. |
| 9,532,806 B2 | 1/2017 | McDonnell |
| 9,585,695 B2 | 3/2017 | Jones et al. |
| 2002/0055749 A1 | 5/2002 | Esnouf et al. |
| 2002/0083821 A1 | 7/2002 | Uchida |
| 2002/0143340 A1 | 10/2002 | Kaneko |
| 2002/0147454 A1 | 10/2002 | Neto |
| 2003/0036761 A1 | 2/2003 | Smothers et al. |
| 2003/0045880 A1 | 3/2003 | Michelson |
| 2004/0024456 A1 | 2/2004 | Brown, Jr. et al. |
| 2004/0068267 A1 | 4/2004 | Harvie et al. |
| 2004/0094024 A1 | 5/2004 | Kim |
| 2004/0133204 A1 | 7/2004 | Davies |
| 2005/0015154 A1 | 1/2005 | Lindsey et al. |
| 2005/0070930 A1 | 3/2005 | Kammerer |
| 2005/0150370 A1 | 7/2005 | Nishri et al. |
| 2005/0216006 A1 | 9/2005 | Orbay et al. |
| 2005/0251143 A1 | 11/2005 | Dillard |
| 2005/0255230 A1 | 11/2005 | Clerc et al. |
| 2006/0089646 A1 | 4/2006 | Bonutti |
| 2006/0129148 A1 | 6/2006 | Simmons et al. |
| 2007/0060923 A1 | 3/2007 | Dreyfuss |
| 2007/0093899 A1 | 4/2007 | Dutoit et al. |
| 2007/0118131 A1 | 5/2007 | Gooch |
| 2007/0118144 A1 | 5/2007 | Truckai et al. |
| 2007/0191956 A1 | 8/2007 | Prewett et al. |
| 2007/0250114 A1 | 10/2007 | Drapeau |
| 2007/0270941 A1 | 11/2007 | Headley et al. |
| 2008/0027445 A1 | 1/2008 | Brown et al. |
| 2008/0255560 A1 | 10/2008 | Myers et al. |
| 2008/0262630 A1 | 10/2008 | Fulmer et al. |
| 2008/0281430 A1 | 11/2008 | Kelman et al. |
| 2009/0024147 A1 | 1/2009 | Ralph et al. |
| 2009/0136898 A1 | 5/2009 | Kim |
| 2009/0193961 A1 | 8/2009 | Jensen et al. |
| 2009/0216338 A1 | 8/2009 | Gingras et al. |
| 2009/0254124 A1 | 10/2009 | Bickley et al. |
| 2009/0279980 A1* | 11/2009 | Gruber .................. F16B 13/04 411/22 |
| 2009/0306777 A1 | 12/2009 | Widmer et al. |
| 2010/0016940 A1 | 1/2010 | Shokoohi et al. |
| 2010/0076503 A1 | 3/2010 | Beyar et al. |
| 2010/0125273 A1 | 5/2010 | Schwieger et al. |
| 2010/0152786 A1 | 6/2010 | Behrbalk |
| 2010/0168505 A1 | 7/2010 | Inman et al. |
| 2010/0179591 A1 | 7/2010 | Saltzman et al. |
| 2010/0292738 A1 | 11/2010 | Reiley |
| 2010/0318085 A1 | 12/2010 | Austin et al. |
| 2010/0324607 A1 | 12/2010 | Davis |
| 2010/0331881 A1 | 12/2010 | Hart |
| 2011/0061519 A1 | 3/2011 | Fields |
| 2011/0106177 A1 | 5/2011 | Lewis |
| 2011/0144766 A1 | 6/2011 | Kale et al. |
| 2011/0184472 A1 | 7/2011 | Niederberger et al. |
| 2011/0213467 A1 | 9/2011 | Lozier et al. |
| 2011/0230948 A1 | 9/2011 | Ehrenreich et al. |
| 2012/0065649 A1 | 3/2012 | Towler |
| 2012/0123416 A1 | 5/2012 | Gelfand et al. |
| 2012/0172934 A1 | 7/2012 | Fisher et al. |
| 2012/0239145 A1 | 9/2012 | Peterson et al. |
| 2012/0245704 A1 | 9/2012 | Childs |
| 2012/0259372 A1 | 10/2012 | Glazer et al. |
| 2012/0264084 A1 | 10/2012 | Hansson et al. |
| 2013/0013065 A1 | 1/2013 | Bills |
| 2013/0014544 A1 | 1/2013 | Winkler |
| 2013/0018318 A1 | 1/2013 | Ravichandran et al. |
| 2013/0103166 A1 | 4/2013 | Butler et al. |
| 2013/0131684 A1 | 5/2013 | Farrell |
| 2013/0178946 A1 | 7/2013 | Monaghan et al. |
| 2013/0184819 A1 | 7/2013 | Donnelly et al. |
| 2013/0226204 A1 | 8/2013 | Kumar |
| 2013/0289621 A1 | 10/2013 | Fulmer et al. |
| 2014/0046454 A1 | 2/2014 | Rose et al. |
| 2014/0052178 A1 | 2/2014 | Dooney, Jr. |
| 2014/0090549 A1 | 4/2014 | Hurlen |
| 2014/0094805 A1 | 4/2014 | Bonutti et al. |
| 2014/0100590 A1 | 4/2014 | Gingras et al. |
| 2014/0128916 A1 | 5/2014 | Williams |
| 2014/0207145 A1 | 7/2014 | Sennett |
| 2014/0277150 A1 | 9/2014 | Jones et al. |
| 2014/0277449 A1 | 9/2014 | Jones |
| 2014/0358145 A1 | 12/2014 | Schaller et al. |

(56) References Cited

U.S. PATENT DOCUMENTS

| | | |
|---|---|---|
| 2015/0045831 A1 | 2/2015 | Allen |
| 2015/0275408 A1 | 10/2015 | Tahara et al. |
| 2015/0342764 A1 | 12/2015 | Ramzipoor et al. |
| 2016/0010248 A1 | 1/2016 | Lariviere et al. |
| 2016/0038187 A1 | 2/2016 | McDonnell |
| 2016/0058524 A1 | 3/2016 | Tehrani et al. |
| 2016/0074071 A1 | 3/2016 | McDonnell et al. |
| 2016/0074072 A1 | 3/2016 | McDonnell et al. |
| 2016/0074084 A1 | 3/2016 | McDonnell et al. |
| 2016/0168769 A1 | 6/2016 | McDonnell |
| 2016/0183942 A1 | 6/2016 | Allen |
| 2016/0317332 A1 | 11/2016 | Lilbum et al. |
| 2016/0345676 A1 | 12/2016 | Bruce et al. |
| 2017/0035481 A1 | 2/2017 | Magee et al. |
| 2017/0035482 A1 | 2/2017 | Magee et al. |
| 2017/0071634 A1 | 3/2017 | McDonnell |
| 2017/0128100 A1 | 5/2017 | Jones et al. |
| 2017/0165077 A1 | 6/2017 | McDonnell |
| 2017/0215934 A1 | 8/2017 | McDonnell |

FOREIGN PATENT DOCUMENTS

| | | |
|---|---|---|
| FR | 2725615 A1 | 4/1996 |
| FR | 2955259 A1 | 7/2011 |
| GB | 2 307 179 A | 5/1997 |
| WO | 1983/002555 A1 | 8/1983 |
| WO | 1989/001320 A1 | 2/1989 |
| WO | 1994/007425 A1 | 4/1994 |
| WO | 1996/003084 A1 | 2/1996 |
| WO | 2001/056506 A1 | 8/2001 |
| WO | 2001/070135 A2 | 9/2001 |
| WO | 2006/105935 A1 | 10/2006 |
| WO | 2007/103404 A2 | 9/2007 |
| WO | 2010/042293 A1 | 4/2010 |
| WO | 2012/116319 A2 | 8/2012 |
| WO | 2012/121726 A1 | 9/2012 |
| WO | 2013/004763 A1 | 1/2013 |
| WO | 2016/022491 A1 | 2/2016 |
| WO | WO 2016/044471 A1 | 3/2016 |
| WO | 2017/024277 A1 | 2/2017 |
| WO | 2017/024280 A1 | 2/2017 |

OTHER PUBLICATIONS

International Search Report and Written Opinion in International Application No. PCT/US2016/045899, dated Oct. 11, 2016.
International Search Report and Written Opinion in International Application No. PCT/US2016/045903, dated Nov. 2, 2016.
U.S. Appl. No. 29/524,091: Office Action dated Jun. 5, 2015.
U.S. Appl. No. 29/524,091: Notice of Allowance dated Jan. 25, 2016.
U.S. Appl. No. 29/524,091 filed Apr. 16, 2015.
International Search Report and Written Opinion in corresponding International Application No. PCT/US2015/065028, dated Feb. 12, 2016.
International Search Report in International Application No. PCT/US15/50483, dated Dec. 28, 2015.
International Search Report and Written Opinion in International Application No. PCT/US2015/050506, dated Dec. 14, 2015.
Alves et al., "Injectability Evaluation of Tricalcium Phosphate Bone Cement", J Mater Sci Mater Med., vol. 19(5), 2008 (Abstract).
Non-Final Office Action issued in corresponding U.S. Appl. No. 14/209,514 dated Jul. 27, 2017 (10 pages).
Non-Final Office Action issued in corresponding U.S. Appl. No. 14/569,541 dated Feb. 27, 2017 (21 pages).
Non-Final Office Action issued in corresponding U.S. Appl. No. 14/487,895 dated Mar. 24, 2017 (6 pages).
Non-Final Office Action issued in corresponding U.S. Appl. No. 14/487,951 dated Mar. 22, 2017 (6 pages).
Non-Final Office Action issued in corresponding U.S. Appl. No. 15/359,021 dated Feb. 1, 2017 (16 pages).
Notice of Allowance issued in corresponding U.S. Appl. No. 15/359,021 dated Sep. 13, 2017 (8 pages).
ACE Surgical Supply Co., Inc. Titanium Augmentation Micro Mesh—7, http://www.acesurgical.com/bone-grafting/graft-holding-mesh-foils/mic . . . , Jun. 19, 2014.
Biomesh® Neurological Patches N3L—Spinal dura-mater substitutes—Cousin Biotech, <http://www.cousin-biotech.com/uk/produit.php?idrubrique=16&idspecialite=35&idproduit=81>, Jun. 19, 2014.
Bioretec—ActivaScrew Cannulated—Surgical Technique, <http://www.bioretec.com/products/pro_orthotrauma/activascrew-cannulated/surgical-technique.php>, Jun. 12, 2014.
ConMed, Fixation Implants, <http://www.conmed.com/products/knee-fixation.php>, Jun. 10, 2014.
Gore-Tex® Soft Tissue Patch, <http://www.goremedical.com/stp/>, Jun. 19, 2014.
Medtronic Sofamor Danek, Vertex® Max, Reconstruction System Surgical Technique, © 2005.
The Open Prosthetics Project: suspension, <http://openprosthetics.org/suspension>, Jun. 16, 2014.
Synthes GmbH, Angular Stable Locking System (ASLS). For angular stable locking of intra-medullary nails, Technique Guide, © Oct. 2008.
Synthes GmbH, DLS Dynamic Locking Screw. Combined with LCP Locking Compression Plate, Instructions for Use, © Oct. 2012.
Vicryl® (polyglactin 910) Woven Mesh—Ethicon, <http://www.ethicon.com/healthcare-professionals/products/tissue-hemia/meshNicryl-polyglactin-910-woven-mesh>.
K.P. Chellamani et al., Medical textiles using Braiding Technology, Journal of Academia and Industrial Research (JAIR), vol. 2, Issue 1, Jun. 2013, pp. 21-26.
Ho Jung Kang et al., An Experimental Intraarticular Implantation of Woven Carbon Fiber Pad into Osteochondral Defect of the Femoral Condyle in Rabbit, Yonsei Medical Journal, vol. 32, No. 2, 1991, pp. 108-116.
D. S. Muckle et al., Biological Response to Woven Carbon Fibre Pads in the Knee, The Journal of Bone and Joint Surgery, 1989, 7I-B, pp. 60-62.
Takanobu Nishizuka et al., Intramedullary-fixation Technique for Long Bone Fragility Fractures Using Bioabsorbable Materials, Orthopedic Research Annual Meeting, Mar. 2014.
Maureen Suchenski, M.D. et al., Material Properties and Composition of Soft-Tissue Fixation, Arthroscopy: The Journal of Arthroscopic and Related Surgery, vol. 26, No. 6, Jun. 2010, pp. 821-831.
Stephanie C. Von Plocki, et al., Biodegradable Sleeves for Metal Implants to Prevent Implant-Associated Infection: An Experimental In Vivo Study in Sheep, Veterinary Surgery, vol. 41, Issue 3, Apr. 2012, pp. 410-421.
Andre Weimann, M.D., et al., Primary Stability of Bone-Patellar Tendon-Bone Graft Fixation With Biodegradable Pins, Arthroscopy: The Journal of Arthroscopic and Related Surgery, vol. 19, No. 10, Dec. 2003, pp. 1097-1102.
McDonnell, U.S. Appl. No. 14/452,054, filed Aug. 5, 2014.
McDonnell, U.S. Appl. No. 14/487,873, filed Sep. 16, 2014.
McDonnell, U.S. Appl. No. 14/487,895, filed Sep. 16, 2014.
McDonnell, U.S. Appl. No. 14/487,951, filed Sep. 16, 2014.
McDonnell, U.S. Appl. No. 14/569,541, filed Dec. 12, 2014.

* cited by examiner

WOVEN RETENTION DEVICES, SYSTEMS AND METHODS

CROSS-REFERENCE TO RELATED APPLICATIONS

This application claims priority to U.S. Provisional Application No. 62/033,455, filed Aug. 5, 2014, the disclosure of which is incorporated herein by reference in its entirety.

TECHNICAL FIELD

The present invention relates to devices, systems and methods for use in fixing fasteners to bone tissue.

BACKGROUND

In orthopedic surgery it is common to secure a bone screw to a patient's bone. Bone fracture repair is surgery to fix a broken bone using plates, nails, screws, or pins. It is common in the treatment of fractures to attach a plate to the bone utilizing bone screws. The resulting construct prevents motion of the fractured bone so that the bone can heal. Alternatively, one or more screws may be inserted across the break to hold it place.

In the treatment of spinal disorders, pedicle screws are inserted into the patient's vertebrae to serve as anchor points that can then be connected with a rod. This construct prevents motion of the vertebral segments that are to be fused.

In the treatment of detached tendons, screw-like tissue anchors are inserted into the patient's bone to serve as an anchor for the reattachment of the tendon.

One complication with the use of bone screws is the loss of fixation or grip between the bone screw and the patient's bone. Another complication with the use of bone screws is the stripping of the hole in the bone when the bone screw is inserted. This results in the loss of purchase and holding strength of the bone screw.

The presence of osteoporotic bone can increase the likelihood of complications by reducing the purchase or grip of the bone screw to the patient's bone, resulting in a loss of holding strength and loosening of the bone screw or pullout of the bone screw.

Current solutions to secure bone screws have not adequately addressed screw failure and the underlying causes of screw failure.

BRIEF SUMMARY OF THE INVENTION

There is a need for devices, systems and methods that enhance the surface of a bone hole to provide enhanced fixation of a bone anchor to the bone. Additionally, there is a need for devices, systems and methods for repairing the surface of the bone hole following damage to the bone hole as in the case of stripping of the hole in the bone when a bone screw is over-tightened. Also, there is a need for devices, systems and methods for providing an enhanced bone hole surface for the reattachment of tendons in, for example anterior/posterior cruciate ligament repair procedures, rotator cuff repair procedures, etc. There is a need for a device that enhances the surface of a bone hole to enhance fixation of a bone anchor to bone and permits bone ingrowth into its structure. There is a need for a single device that enhances the surface of a bone hole to enhance fixation of a bone anchor to bone and accommodates variations in the diameter and depth of the bone hole.

According to an embodiment of the invention, a woven retention device for interfacing with a bone surface is provided. The retention device may include a sleeve body having a plurality of sets of interwoven monofilaments that form a substantially tubular lattice, and the sleeve body may be able surround at least a portion of a fastener. A plurality of protuberances is distributed on an interior surface and an exterior surface of the tubular lattice at a predetermined spatial relationship. The plurality of sets of interwoven monofilaments may have a plurality of different diameters. The retention device also includes a proximal end that is proximal to the sleeve body and that may receive at least a portion of the fastener. The retention device also includes a distal end that is distal to the sleeve body. In a first state, the sleeve body has a plurality of combinations of filament cross-section geometries at the intersection points, the plurality of combinations of filament cross-section geometries may form a plurality of protuberance thicknesses, where a thickness of each protuberance may be measured in a radial direction of the sleeve body. In a second state when a fastener is inserted into the tubular lattice, pressure from the fastener is transmitted to the tubular lattice such that the spatial relationship of the protuberances changes according to a function of bone density and according to a function of an interfacing surface shape of the fastener.

In an aspect of an embodiment, the plurality of sets of interwoven monofilaments can include a first plurality of monofilaments that runs in a first helical direction and a second plurality of monofilaments that runs in a direction intersecting the first plurality of monofilaments. For each set of the first and second plurality of monofilaments, there can be a substantially same arrangement of cross-section geometries at every other intersection along that set, the substantially same arrangement being different from an arrangement of cross-section geometries at remaining intersections along that set. The retention device may further include a first plurality of multifilaments that runs in the first helical direction and a second plurality of multifilaments that runs in the second direction. The first plurality of monofilaments and the first plurality of multifilaments may form a first plurality of sets of filaments and the second plurality of monofilaments and the second plurality of multifilaments may form a second plurality of sets of filaments.

In an aspect of an embodiment, each of the first plurality of sets of filaments comprises a first outer filament and a first inner filament, and each of the second plurality of sets of filaments comprises a second outer filament and a second inner filament. In another aspect of an embodiment, the distal end has a distal tip with a first diameter, and the receiving portion has a second diameter that is greater than the first diameter.

Each of the first plurality of sets of filaments may include a first outer filament and a first inner filament, and each of the second plurality of sets of filaments may include a second outer filament and a second inner filament. The first plurality of monofilaments can be thinner in diameter than the second plurality of monofilaments.

The plurality of interwoven filaments can follow a two-under/two-over configuration, where at each intersection, the second plurality of monofilaments either overlies both of the intersecting monofilaments or is overlain by both of the intersecting monofilaments and the second plurality of monofilaments overlies one of the intersecting filaments and is overlain by the other of the intersecting filaments. In another aspect, the plurality of interwoven filaments can be arranged in a one-under/one-over configuration. In a further aspect, the plurality of interwoven filaments can be arranged in a two-over/one-under configuration. In another aspect of an embodiment, the plurality of interwoven filaments can be arranged in a three-under/three-over configuration.

In an aspect of an embodiment, the first plurality of monofilaments can have a diameter in a range of about 0.1 mm-0.4 mm. In a further aspect, the first plurality of monofilaments can have a diameter of 0.2 mm. The plurality of interwoven filaments can include a plurality of flat multifilaments.

According to an aspect of an embodiment, the interwoven filaments can outline interstices that allow for bone ingrowth, and the interstices formed by the intersecting filaments can include differently shaped and differently sized interstices. The distal end of the retention device can be closed.

In an aspect of an embodiment, in the relaxed state, the interwoven filaments extend around the tubular lattice at an angle of about 45 degrees with respect to a longitudinal direction of the woven retention device. According to another aspect, the distributed protuberances can be arranged in a diamond-shaped pattern grid.

According to an aspect of an embodiment, the tubular lattice can have an outer radius spanning from a furthest outwardly extending protuberance in the radial direction on the exterior surface of the tubular lattice to a center point of the tubular lattice, the tubular lattice having an inner radius spanning from a furthest inwardly protruding protuberance in the axial direction on the interior surface of the tubular lattice to the center point of the tubular lattice, and the tubular lattice having an average radius that is an average between the outer radius and the inner radius. The outer radius of the tubular lattice can be greatest at the intersection point of two of the thick monofilaments. In some embodiments, the tubular lattice can have an average diameter that is in a range of about 1.5 mm to 9.0 mm. The woven retention device may have a length in a range from about 30 mm to 40 mm, according to some embodiments.

According to some embodiments, the fastener can be a screw having a screw thread and the interior surface is configured to interact with the screw. The fastener can apply pressure to the inner surface, and the pressure can be transmitted to protuberances on the outer surface adjacent to the protuberance on the outer surface that inner surface and exerting pressure on bone material. In an aspect of an embodiment, the retention device includes the fastener.

In a further aspect of an embodiment, in the second state when the sleeve body distributes pressure from the fastener on the interior surface to the exterior surface, the fastener may require at least 10% more pullout force to pull the fastener out of the bone with the retention device than the pullout force required for a fastener in the bone hole without the retention device According to an embodiment of the present invention, a retention device for interfacing with a bone surface is provided. The retention device includes a substantially tubular lattice of intersecting fibers that can be inserted into a bone tunnel. The tubular lattice includes a proximal end and a distal end, and the proximal end has a receiving portion that can receive a fastener along a longitudinal axis of the retention device. The tubular lattice may include an inner surface that has a distributed interface with protruding and recessed portions that can interact with an outer surface of the fastener, The tubular lattice may further include an outer surface that has protruding and recessed multiple points of contact configured to interact with an interior bone surface. The tubular lattice can have a degree of stability that maintains a three-dimensional structure of the tubular lattice and have a degree of flexibility. The degree of stability and flexibility may allow for the distributed interface of the inner surface to distribute applied pressure to the protruding and recessed multiple points of contact of the outer surface.

In an aspect of an embodiment, the plurality of intersecting fibers includes sets of a first plurality of monofilaments that runs in a first helical direction and a second plurality of monofilaments that runs in a direction intersecting the first plurality of monofilaments. For each set of the first and second plurality of monofilaments, there can be a substantially same arrangement of cross-section geometries at every other intersection along that set, the substantially same arrangement being different from an arrangement of cross-section geometries at remaining intersections along that set. The first plurality of monofilaments may be thinner in diameter than the second plurality of monofilaments. In some embodiments, the first plurality of monofilaments may have a diameter in a range of about 0.1 mm-0.4 mm. The distal end can have a distal tip with a first diameter, and the receiving portion has a second diameter that is greater than the first diameter.

In another aspect of an embodiment, the intersecting fibers follow a two-under/two-over configuration, where at each intersection, the second plurality of monofilaments either overlies both of the intersecting monofilaments or is overlain by both of the intersecting monofilaments and the second plurality of monofilaments overlies one of the intersecting filaments and is overlain by the other of the intersecting filaments. In some embodiments, the intersecting fibers can outline interstices that allow for bone ingrowth, and the interstices formed by the intersecting fibers can include differently shaped and differently sized interstices.

In the relaxed state, the intersecting fibers can extend around the tubular lattice at an angle of about 45 degrees with respect to a longitudinal direction of the woven retention device. In an aspect of an embodiment, the tubular lattice can have an outer radius spanning from a furthest outwardly extending protuberance in the radial direction on the exterior surface of the tubular lattice to a center point of the tubular lattice, and the tubular lattice can have an inner radius spanning from a furthest inwardly protruding protuberance in the axial direction on the interior surface of the tubular lattice to the center point of the tubular lattice. The tubular lattice can have an average radius that is an average between the outer radius and the inner radius, and the outer radius of the tubular lattice may be greatest at the intersection point of two of the thick monofilaments. When the fastener applies pressure to the inner surface, the pressure can be transmitted to protuberances on the outer surface adjacent to the protuberance on the outer surface that inner surface and exerting pressure on bone material. In the second state when the sleeve body distributes pressure from the fastener on the interior surface to the exterior surface, the fastener may require at least 10% more pullout force to pull the fastener out of the bone with the retention device than the pullout force required for a fastener in the bone hole without the retention device.

According to another embodiment of the present invention, a method of inserting a woven retention device is provided. The method includes inserting the woven retention device into a bone hole, and distributing pressure from a fastener being inserted into the woven retention device from an interior surface of the woven retention device to an exterior surface of the woven retention device for transmission of pressure to bone surface of the bone hole according to a function of bone density and according to a function of an interfacing surface shape of the fastener. The pressure from the fastener may change the spatial relationship of protuberances on the interior surface of the woven retention device, and the pressure from the interior surface may change the spatial relationship of protuberances of the exterior surface of the woven retention device.

In an aspect of an embodiment, the fastener can be inserted into the woven retention device after the woven retention device has been inserted into the bone hole. According to another aspect, the fastener can be inserted into the woven retention device before the woven retention device has been inserted into the bone hole. The pressure transmitted to the bone surface can be adapted to change shape of the bone surface of the bone hole in some embodiments. The distributing of pressure can include dynamic micro-loading of the woven retention device based on differences in loading patterns of the woven retention device and the interfacing surface shape of the fastener In an aspect of an embodiment, the method may further include providing a woven retention device according to any of the embodiments discussed herein.

The method may further include elongating or constricting the woven retention device for fitting the woven retention device inside the bone hole, and expanding the woven retention device upon entering the bone hole Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

DETAILED DESCRIPTION OF THE INVENTIONS

The devices, systems and methods described herein may be used in the area of orthopedics and, in particular, orthopedic repairs. These include various devices, systems and methods directed to fixing and/or retaining fasteners in orthopedic applications. Fixing or retaining fasteners to bone tissue is complicated by the underlining bone tissue. Understanding that an underlying cause of failure with internal fixation in bone tissue is the bone, the devices, systems and methods described herein provide for solutions that address the implant site. At the implant site, the hole and the bone benefit from an enhanced interface.

The fixation and/or retention devices, systems and methods described herein maximize fixation and/or retention in the bone tissue, including, osteoporotic bone, bone of a poor quality, and mechanically poor bone in addition to healthy bone tissue. The fixation and/or retention devices, systems and methods described herein may be used with any type of fixation including, any types of screws.

The devices, systems and methods described herein enhance the interaction of a bone anchor to a bone hole to provide enhanced fixation. Additionally, the devices, systems and methods may repair the surface of the bone hole following damage to the bone hole as in the case of stripping of the hole in the bone when a bone screw is over-tightened. Also, the devices, systems and methods provide for an enhanced bone hole surface for the reattachment of tendons in, for example, anterior/posterior cruciate ligament repair procedures, rotator cuff repair procedures, etc. The devices enhance the surface of a bone hole to enhance fixation of a bone anchor to bone and permits bone ingrowth into its structure. The devices enhance the interaction between the surface of a bone hole and the fixation device. The devices interdigitate with the bony structure and interact with the fixation device. The device alone, as a single device, enhances the surface of a bone hole to enhance fixation of a bone anchor to bone and accommodates variations in the diameter and depth of the bone hole. The devices, systems and methods can enhance fixation without requiring the use of cement and/or adhesives.

Figure 1A:
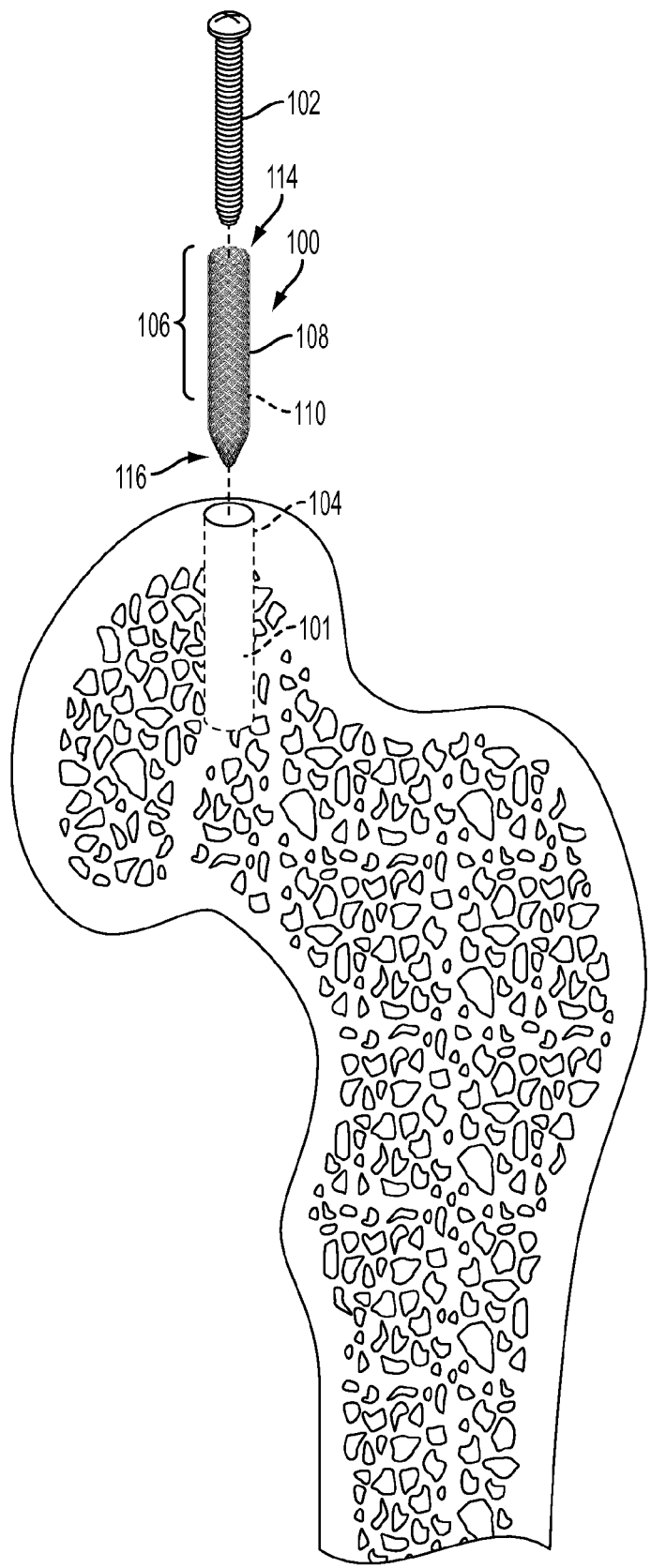
FIG. 1A shows a perspective view of a screw, a woven retention device and a bone, according to an embodiment of the present invention.
Figure 1B:
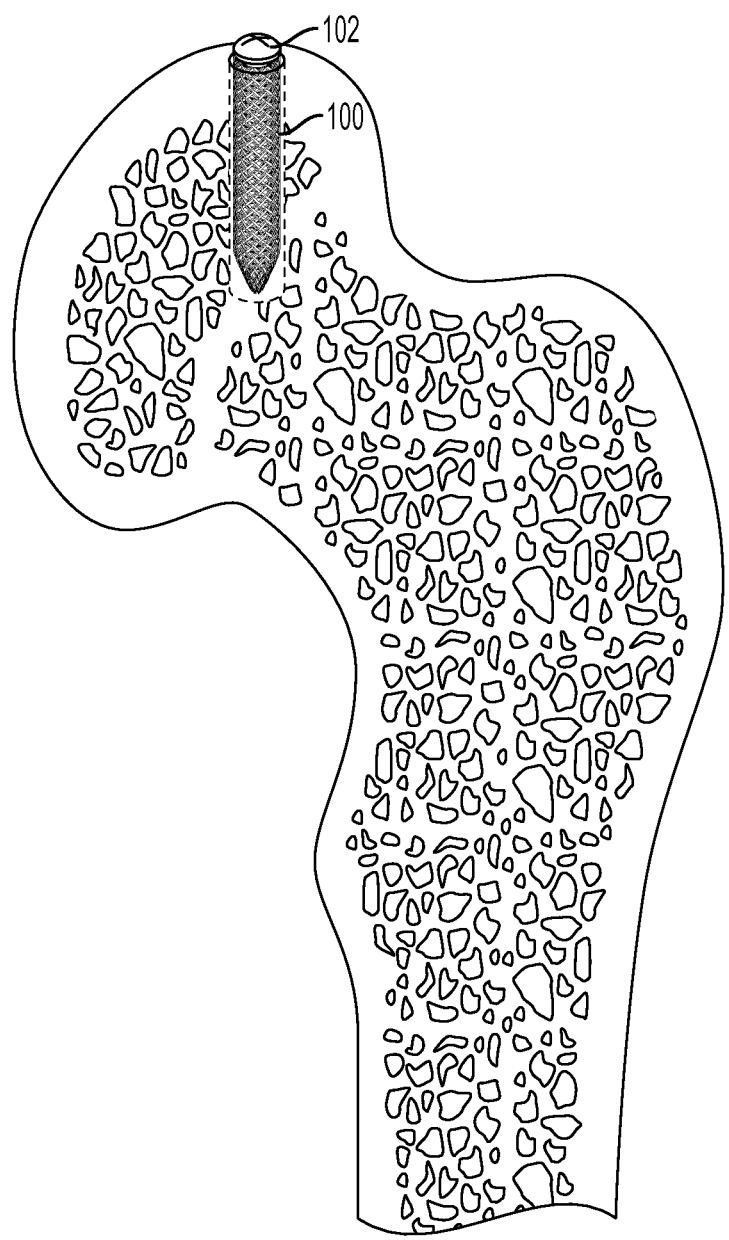
FIG. 1B shows a screw and a woven retention device fixed inside a bone hole, according to an embodiment of the present invention.

Referring now to the figures, FIGS. 1A and 1B show a woven retention device 100 for interfacing with a bone surface 104, according to an example of an embodiment. The retention device 100, as shown, may have a general configuration or construction in the form of a hollow tubular shape shown as a sleeve body 106 including a plurality of interwoven filaments that may form a substantially tubular lattice. The general configuration of the hollow tubular shape can be selected to accommodate a typical shape of a pilot hole in bone, for example. Various configurations of the sleeve body 106 can be contemplated in accordance with the principles of the invention.

The lattice may include a plurality of protuberances distributed on an interior surface 110 and an exterior surface 108 of the lattice at a predetermined spatial relationship. Each of the plurality of protuberances may be formed by an intersection of filaments. More particularly, each of the plurality of protuberances may be formed by an intersection point of two or more of the plurality of interwoven filaments. The intersection can be referred to as a location and/or point. Additionally, the interwoven filaments may outline interstices that allow for bone ingrowth. The woven retention device can also have a proximal end 114 that is proximal to the sleeve body 106 and that is configured to receive at least a portion of a fastener 102 such that the sleeve body 106 may surround at least a portion of the fastener 102 when inserted therein. The woven retention device 100 can also have a distal end 116 that is distal to the sleeve body 106. In some embodiments, the distal end 116 is formed to ease insertion of the woven retention device 100 into the bone hole 101. For example, the distal end 116 in FIG. 1A is tapered. The lattice can be a tubular lattice.

The woven retention device 100 can be inserted into a hole in a bone and interact with both the bone and a screw. While the woven retention device 100 can achieve an interference fit functionality by providing additional interference in between the fastener and the bone, in some embodiments, the woven retention device can instead of and/or in addition to function as a woven retention device in accordance with the configurations, functions and advantages that are discussed herein. For example, the woven retention device can have a dual interface between a radial screw surface on one side and multiple points of contact on a bone surface on the other side. The dual interfaces on the retention device are configured to be adapted to the bony structure on the outside and the screw on the inside, as described herein in accordance with the principles of the invention. The woven retention device can be particularly beneficial for osteoporotic or weakened bone that has more space gaps than normal bone to allow additional points of contact for the interface to contact.

FIG. 1A shows the woven retention device 100 in an exploded state with the fastener 102 outside of the retention device, and both the fastener 102 and the retention device 100 are outside of the bone hole. FIG. 1B shows the fastener 102 inside the woven retention device 100, which is inside the bone. FIGS. 1A and 1B also illustrate an example of a porous interior structure of the bone. However, embodiments of the invention are not limited to being used with the exact porous structure shown, as the structure and porosity of bone can vary. In addition, although the bone illustrated in FIGS. 1A and 1B resembles a human femur, embodiments of the invention are not limited to a particular bone. An advantage of some embodiments of the invention is that a woven retention device can be provided for use in a variety of bones and bones exhibiting varying levels of porosity.

Figure 2A:
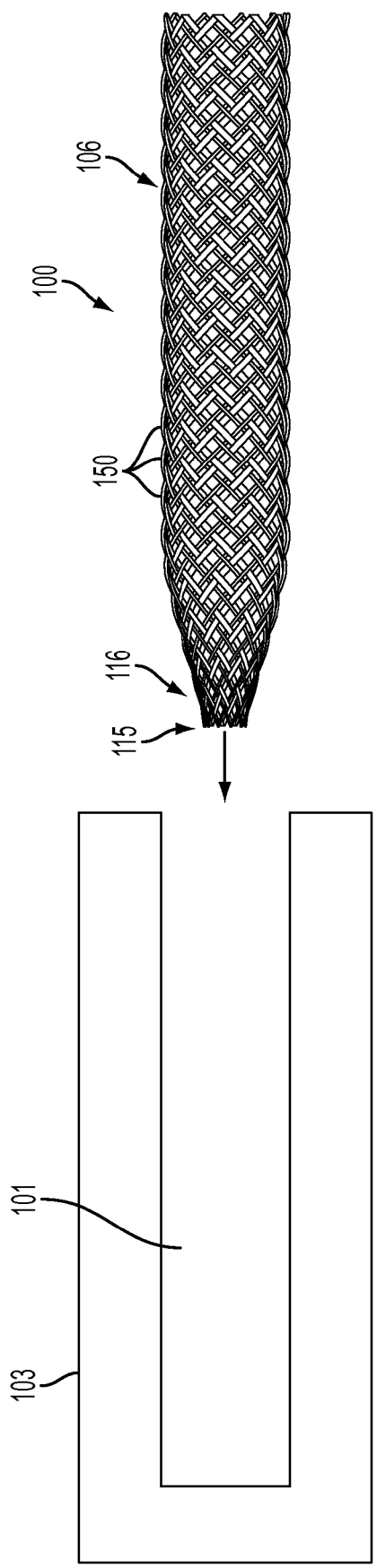
FIG. 2A shows a schematic cross-section view of a bone hole with a woven retention device to be inserted, according to an embodiment of the present invention.

FIG. 2A shows a sleeve body 106 to be inserted into a bone hole 101 in a bone 103. According to this embodiment, the distal end 116 tapers to a distal tip 115 that has a smaller diameter than the sleeve body 106. The tapering at the distal tip 115 can ease insertion of the woven retention device 100 into the bone hole 101. For example, in some embodiments, the diameter of the sleeve body 106 may be equal to or larger than a diameter of the bone hole 101, and the tapering at the distal tip 115 can allow the distal end 116 to find its way into the bone hole 101. For example, after the distal end 116 is at least partially inserted into the bone hole 101, a remainder of the woven retention device 100 can more easily be inserted into the bone hole 101, and, in a case where the diameter of the sleeve body 106 is larger than the diameter of the bone hole 101, the woven retention device 100 can compress radially as the sleeve body 106 is inserted into the bone hole 101. In addition, as discussed further below, the tapering of the distal end 116 and smaller diameter of the distal tip 115 can provide a surface on the interior of the woven retention device 100 for pushing against with a push rod to insert the woven retention device 100 into the bone hole 101, according to some embodiments. The woven retention device 100 may be in a first, relaxed state at the position shown in FIG. 2A. During or after insertion into the bone hole 101, however, the woven retention device 100 may also assume a radially contracted or radially expanded state.

The plurality of interwoven filaments, according to an embodiment of the woven retention device 100, are visible in FIG. 2A. As discussed in detail further below, these filaments may include one or more varieties of filament shapes and sizes such that the sleeve body 106 can have a plurality of combinations of filament cross-section geometries at the intersection of the filaments, which can also be referred to as intersection points of the filaments. Because each intersection of the filaments may form a protuberance 150, the plurality of combinations of filament cross-section geometries may form a plurality of protuberance thicknesses, each thickness being measured in a radial direction of the sleeve body 106. For example, a cross-section geometry can include a shape of the cross-section and/or a size of the cross-section. The combination of the filament cross-section geometries can include the cross-section geometries of both filaments at the intersection.

Figure 2B:
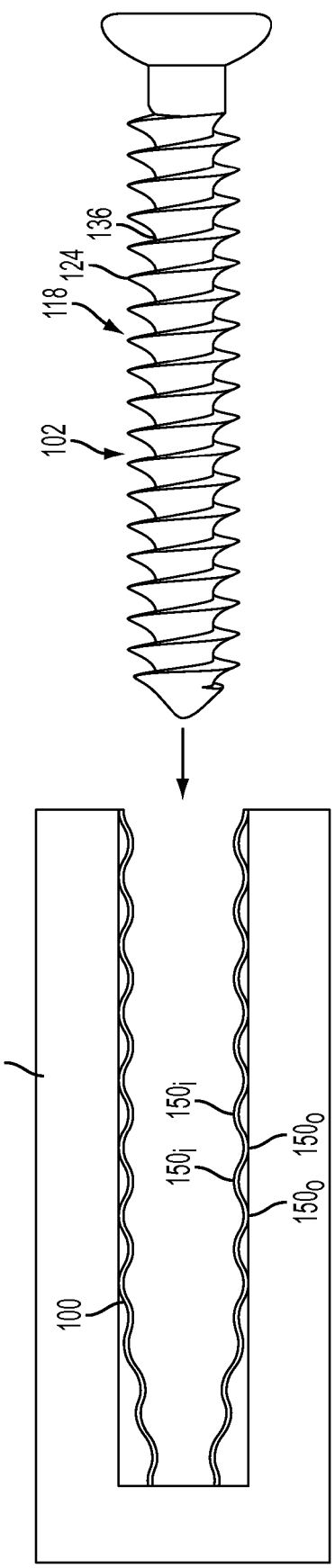
FIG. 2B shows a schematic cross-section side view of a woven retention device inside a bone hole and a fastener outside the bone hole to be inserted, according to an embodiment of the present invention.

FIG. 2B shows a simplified schematic cross-section of the bone hole 101 and the woven retention device 100 inserted therein. For example, the undulating lines representing the sides of the woven retention device 100 in FIG. 2B may represent the plurality of protuberances $150_o$, $150_i$ on the exterior and interior, respectively, of the woven retention device 100 by the series of peaks formed on the respective walls of the woven retention device 100. In the implanted state the woven retention device 100 is adapted to receive the fastener 102. In one embodiment, the fastener 102 can be a screw having a winding protrusion 118, such as a thread of a screw. The woven retention device 100 can be configured such that when the protrusion 118 applies pressure to a protuberance on the interior surface, the pressure is transmitted to protrusions on the exterior surface extending around the protrusion on the interior surface and exerting pressure on bone material.

Embodiments of the invention are not limited to being used with a screw-type fastener. In some embodiments, the fastener may be a nail, rod, prosthetic, or other device for implanting at least partially in a bone. Additionally, in some embodiments a biological material or structure, such as a ligament, may be inserted into the woven retention device.

Figure 2C:
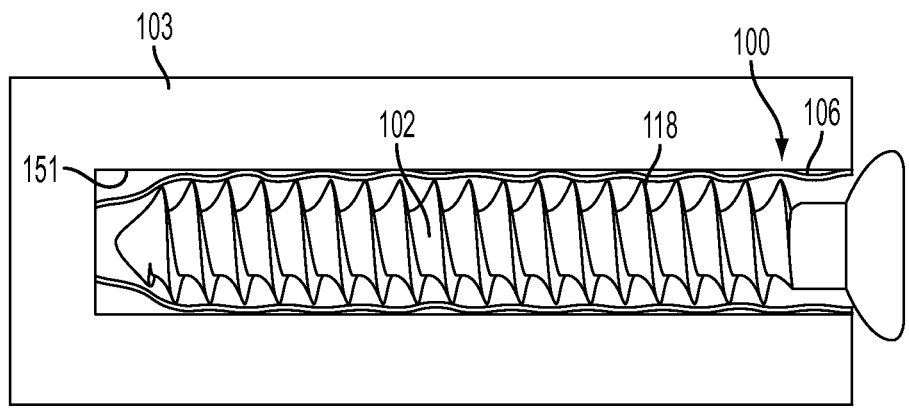
FIGS. 2C and 2D show schematic side cross-section views of a fastener inserted into a bone hole and within a woven retention device where the bone has a different density in each of FIGS. 2C and 2D, according to an embodiment of the present invention.
Figure 2D:
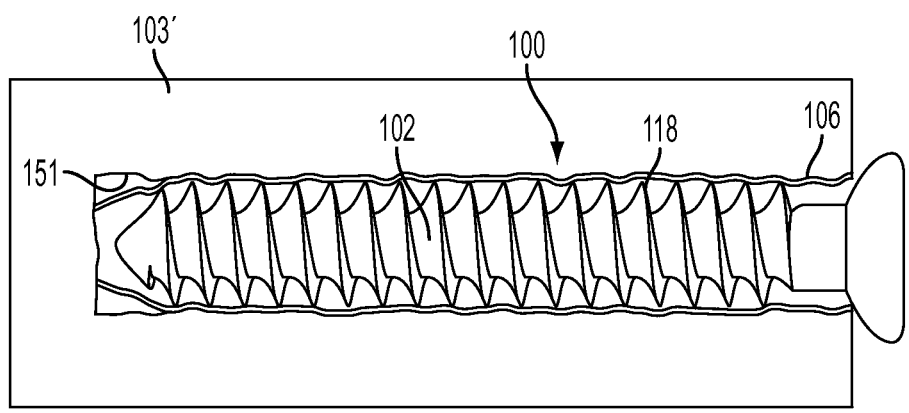

FIGS. 2C and 2D show that in a second state, when surrounding at least a portion of the fastener 102, the sleeve body 106 is configured to engage the bone 103 surrounding the bone hole 101, and may distribute pressure from the fastener 102 to multiple points of contact on the exterior surface of the woven retention device 100 such that the spatial relationship of the plurality of protuberances may change. The spatial relationship of the plurality of protuberances may change as a function of bone density of the bone surface 104. For example, FIG. 2C shows a bone 103 that is more dense than the bone 103' of FIG. 2D. Thus, when the fastener 102 applies pressure on the woven retention device 100, the woven retention device 100 is displaced more prominently in the less dense surface of FIG. 2D than the denser bone surface of FIG. 2C. This displacement of the woven retention device 100 corresponds to a change in the spatial relationship of the plurality of protuberances (the protuberances themselves are not shown in the simplified schematic view of FIGS. 2C and 2D) on the exterior surface, which can allow for greater interdigitation of the woven retention device 100 with the bone surface. In one embodiment, the force from the protuberances on the exterior surface changes the shape of the bone. It is noted that the illustration of the bones 103 and 103' in FIGS. 2C and 2D are simplified schematic representations. In practice, the surfaces of the bones 103 and 103' that are engaged by the woven retention device 100 may be irregular, including a series of voids and projections, for example. Accordingly, the variation in displacement of the sides of the woven retention device 100 when the fastener 102 is inserted can accomplish improved engagement between the woven retention device 100 and the bone 103 (and correspondingly provide the fastener 102 with greater purchase in the bone).

The spatial relationship of the plurality of protuberances can also change as a function of loading and/or the fastener. The spatial relationship of the plurality of protuberances can change as a function of an interfacing surface shape of the fastener 102. As shown in FIG. 2C, the fastener 102 can be a screw. In one embodiment, the screw can be a cancellous screw. In another embodiment, the screw can be a cortical screw. The screw can have crests 124 that are the most outwardly protruding portions of the thread of the screw and can have valleys 136, which are the innermost portions of the screws. The screw can have various levels of coarseness of the threads, representing larger pitch (fewer threads per axial distance). In one embodiment, where the screw has a larger pitch, for instance in a larger size of screw, the retention device when interfacing with the screw can change to accommodate the coarse threads. For example, the retention device can adapt to follow the crests 124 and the valleys 136 to create a general wave pattern. On the other hand, in the case of a smaller diameter screw, or a finer thread with smaller pitch, the retention device can deform or bend over the peaks of the threads less. Thus, in one embodiment, the absolute value of pullout resistance can be greater with a larger screw but the delta between the differential can be smaller with the larger diameter screw because of additional interwinding of the intermediary point of contact. That is, in one embodiment, the protuberances on the exterior surface do not interface as much with the bone because of some of the protuberances folding inward because of the coarseness of the thread. Whereas on the small diameter screw, the woven retention device can move more uniformly, which can allow for greater interdigitation. Thus, because there can be less chance for those interdigitation points to reach into the valleys of the threads, there is more interaction with the bony surface.

The spatial relationship of the plurality of protuberances can also change as a function of an interfacing surface shape based on the length of the surface. For example, the surface of the fastener 102 can also be various lengths. As seen from FIGS. 20-22, even though the change in pullout resistance can be greater with large screws than small screws in total pullout resistance, the small screw can have greater pullout resistance as a measure of percent change. One factor that affects the small screw having a greater pullout resistance in percent change is that more interaction with the woven retention device 100 can be possible with a smaller fastener as a percentage of the fastener's percentage of coverage. This can result in a larger differential in pull out resistance in the smaller sizes than there is in the larger sizes because of the increased interaction. In one embodiment, the mechanical properties of the woven retention device can compensate for differences in the fastener surface. For example, to increase bone surface interaction with a fastener 102 that has a coarse thread, a woven retention device with a greater level of stability can be used to prevent the filaments from retreating too far into the valleys 136 and instead interacting with the bone surface.

In some embodiments, the woven retention device 100 may be specifically configured for a bone of a particular density or range of densities. For example, the structural configuration, material properties, or other aspects of the woven retention device may be adjusted to provide desired engagement with the bone surface of a particular density or range of densities. However, in some embodiments, a particular woven retention device may be suitable for use in bones of varying densities.

Figure 3A:
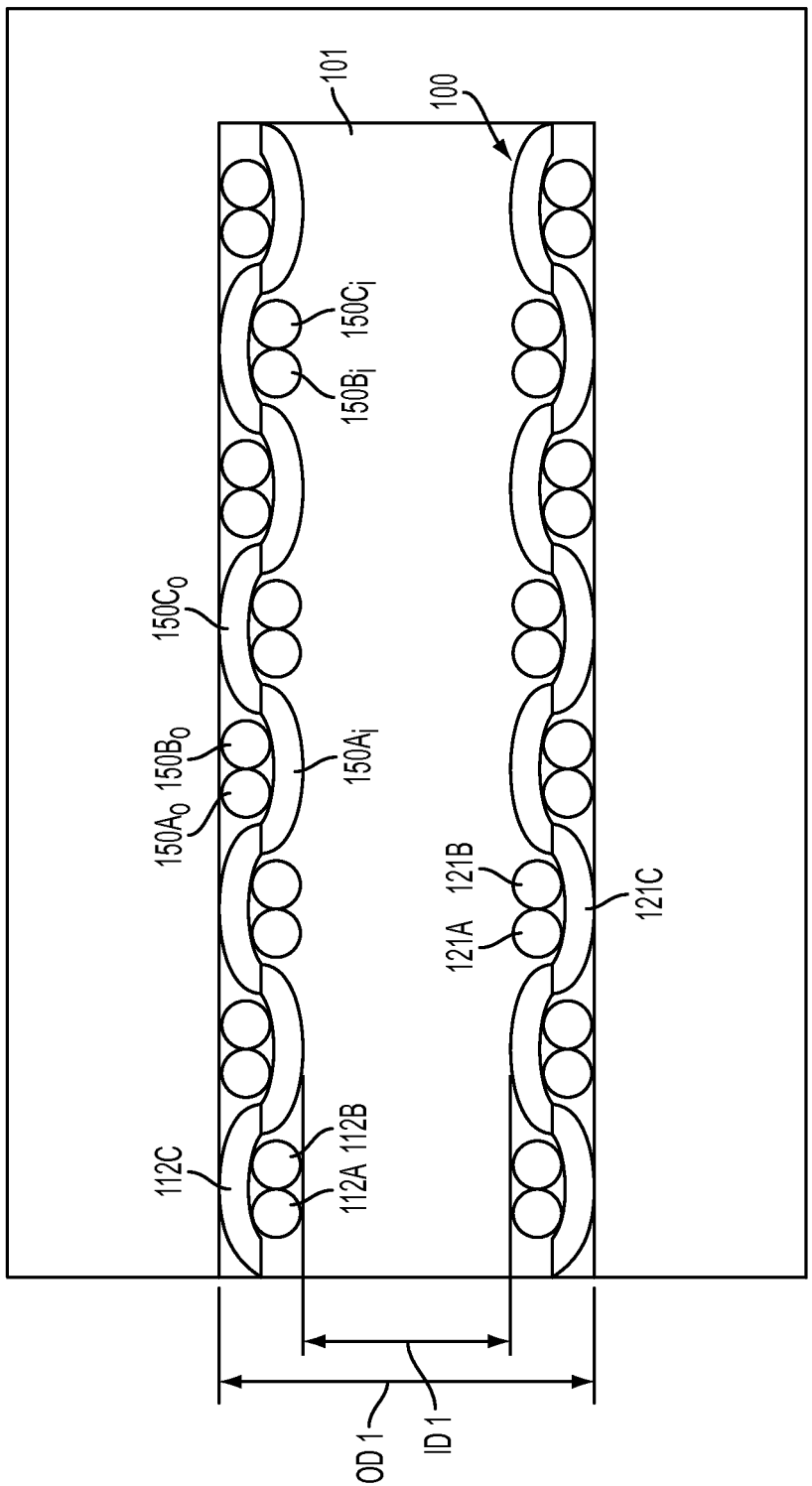
FIG. 3A shows a schematic longitudinal cross-section view of a woven retention device in a bone hole, according to an embodiment of the present invention.

FIG. 3A shows an alternative schematic representation of a cross-section of the woven retention device 100, according to an embodiment. The cross-section of the woven retention device in FIG. 3A reveals an example of the constituent filament cross-section geometries 121A, 121B, 121C that contribute to the protuberances $150A_o$, $150B_o$, $150C_o$, $150A_i$, $150B_i$, $150C_i$ of the woven retention device 100. At least one filament 112C can be seen weaving over and under adjacent filaments 112A, 112B with substantially circular cross-sections. The woven retention device in FIG. 3A is positioned within the bone hole 101 but without the fastener, resulting in an inner diameter ID1 and an outer diameter OD1 of the woven retention device 100. Outer diameter OD1 can be a distance from an outermost protuberance on the exterior surface of one side to a protuberance on the exterior surface on the opposing side. Further, inner diameter ID1 can be a distance from an innermost protuberance on the interior surface of one side to an innermost protuberance on the interior surface of an opposing side. The relationship between the outer diameter OD1 and the inner diameter ID1 can be based on the thickness or diameter of the filaments.

Figure 3B:
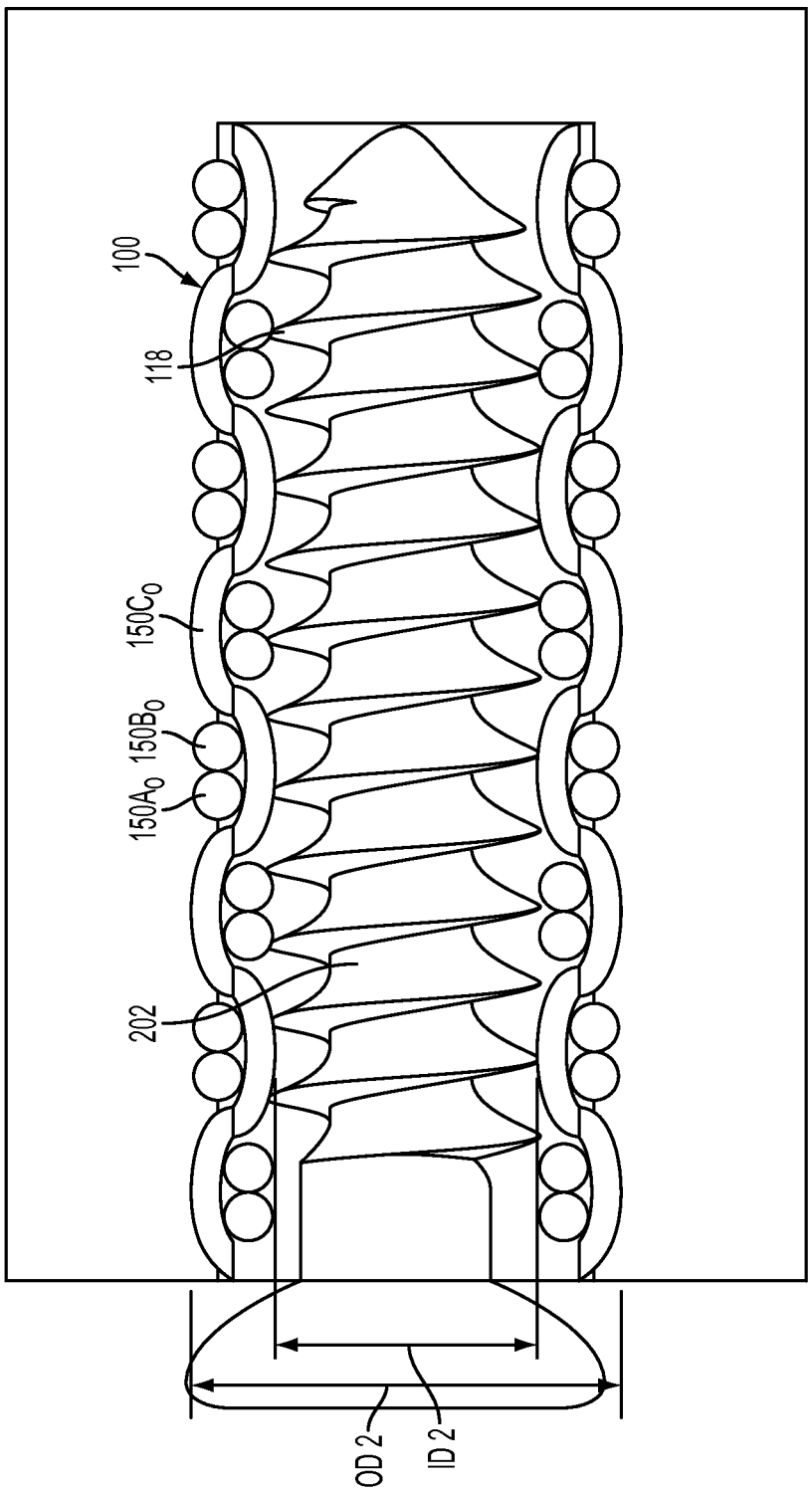
FIG. 3B shows the schematic longitudinal cross-section view of a woven retention device in a bone hole along with an inserted screw, according to an embodiment of the present invention.

FIG. 3B shows an alternative fastener 202 that interfaces with the woven retention device 100. As can be seen, FIG. 3B shows that the fastener 202 changes the spatial relationship of the protuberances (e.g., protuberances $150_o$) from the spatial relationship in FIG. 3A. While outer diameter OD2 can still be a distance from an outermost protuberance on the exterior surface of one side to a protuberance on the exterior surface on the opposing side and inner diameter ID2 can still be a distance from an innermost protuberance on the interior surface of one side to an innermost protuberance on the interior surface of an opposing side, a change in the spatial relationship can result in a larger inner diameter ID2 and outer diameter OD2. The OD2 distance can be a distance larger than outer diameter OD1. Similarly, in one embodiment, the distance ID2 can be larger than the distance ID1. The amount of change of the spatial relationship of the protuberances may change based on the alternative constructions of the fasteners 102 and 202 in FIGS. 2C and 3B, respectively. For example, bone screws are provided in various size and types, which may have different minor diameters, major diameters, thread pitches, pitch diameters, and lengths.

The change in the spatial relationship of the protuberances between FIGS. 3A and 3B can be, in one embodiment, understood as a radial expansion of the woven retention device 100 upon insertion of a fastener therein. This radial expansion can be substantially uniform, as indicated by the uniform displacement of the woven retention device 100 from ID1, OD1 in FIG. 3A to ID2, OD2 in FIG. 3B. As the radial expansion occurs, the spatial relationship between the protuberances on the surface of the woven retention device changes (i.e., the protuberances may spread apart from one another like points on the surface of an inflating balloon). However, according to some embodiments of the present invention, the woven retention device 100 may not expand uniformly when in the bone hole 101. For example, depending on the specific structure of a non-uniform bone surface within the bone hole 101, and depending on the characteristics of the fastener and configuration of the woven retention device, the change in spatial relationship of the protuberances may not be uniform, and may instead include localized changes in the protuberance dispositions. Such localized changes may occur in multiple areas of the woven retention device and may include varying degrees of disposition changes between different areas of the retention device. This capability and/or flexibility provided by some embodiments of the present invention may provide for better bone engagement and fastener retention.

Figure 3C:
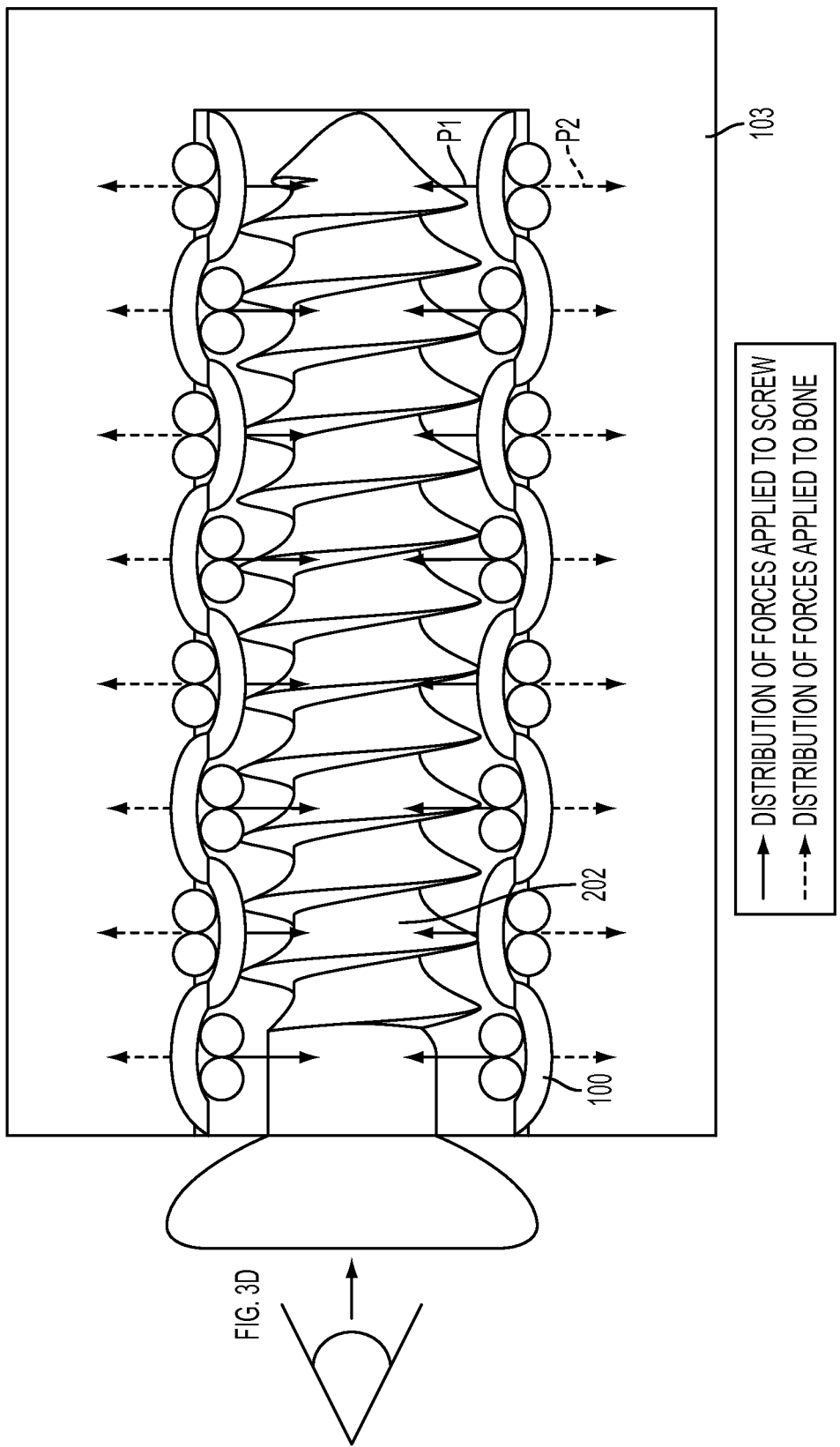
FIG. 3C shows interaction forces between a screw, a woven retention device and a bone, according to an embodiment of the present invention.

FIG. 3C shows the different radial pressures that can be applied when the fastener 202 is inserted into the woven retention device 100, which is disposed in the bone 103. For example, after the fastener 202 is inserted, the outward radial pressure supplied by the fastener alters the disposition of the woven retention device 100, as discussed above. As a result, pressure P1 is exerted between the retention device 100 and fastener 202. Thus, corresponding pressure P2 is exerted between the retention device 100 and the bone 103 from the pressure transferred by the retention device 100 from the fastener 202. In other words, the woven retention device 100 is a dual-interface. The dual interface includes an inner, fastener-retention device interface and an outer, retention device-bone interface. These two interfaces work in conjunction to provide improved fastener retention and holding power in the bone.

Figure 3D:
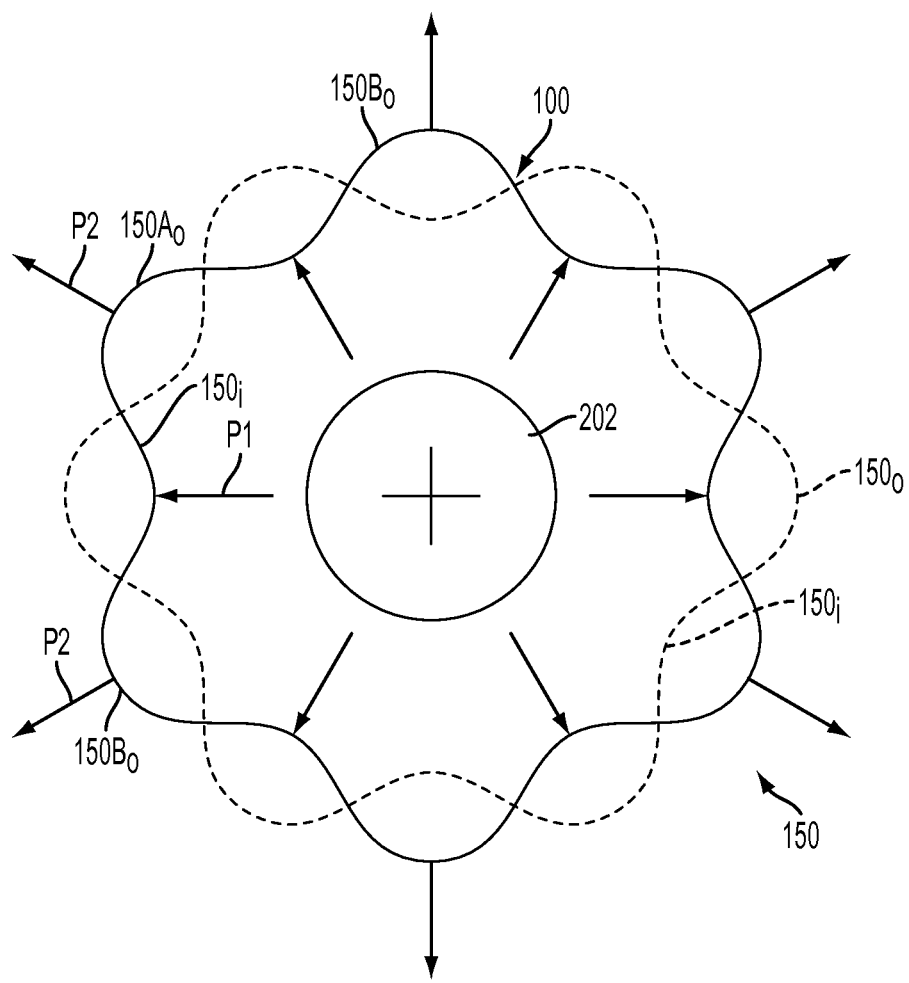
FIG. 3D shows a schematic axial view of a fastener in a woven retention device along with resulting pressures, according to an embodiment of the present invention.

FIG. 3D shows a schematic axial view of the retention device 100 and fastener 202 that are shown in FIG. 3C. For clarity with respect to the pressure forces P1, FIG. 3D shows space between the fastener 202 and an inside of the woven retention device 100, and thus FIG. 3D is not to scale. From the perspective in FIG. 3D, it can be appreciated that the pressures P1 and P2 can radiate in all directions with respect to a center of the woven retention device 100. In addition, according to some embodiments of the invention, a pressure P1 exerted between the fastener 202 and an interior protuberance $150_i$ can be transferred through the woven retention device 100 to multiple exterior protuberances $150A_o$ and $150B_o$ to exert pressure P2 at multiple points of contact with the bone.

Figure 4:
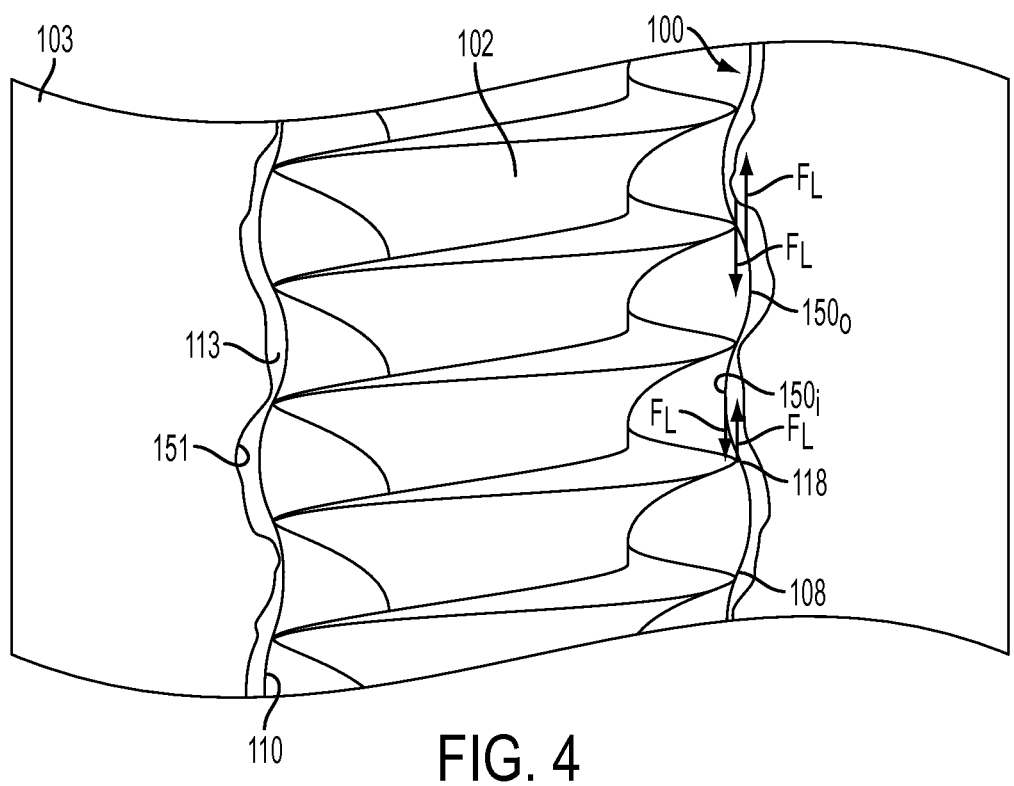
FIG. 4 shows forces in a longitudinal direction of a woven retention device, according to an embodiment of the present invention.

FIG. 4 shows a side view of a fastener 102 inside of a retention device 100 and inside a bone hole 101, according to an embodiment of the present invention. Longitudinal forces $F_L$ can act between interdigitated portions of the retention device (e.g., the protuberances $150_i$, $150_o$) and the bone surface 151, and between the retention device 100 and the fastener 102. These longitudinal forces can act to prevent pullout of the fastener 102, which can add to the resiliency of the fastener 102 in the longitudinal direction. For example, because of the interaction between the protuberances $150_i$ on the interior surface 110 of the woven retention device 100 and the surface of the fastener (which can optionally be screw ridge 118), there is increased resistance and it is more difficult for the fastener 102 to be pulled out. Similarly, because of the interaction between the protuberance $150_o$ on the exterior surface 108 and the surface 151 of the bone 103, there is increased resistance to pullout the fastener 102. FIG. 4 also shows a gap 113 between the exterior surface 108 of the woven retention device 100 and the bone surface 151. The gap 113 may be smaller or larger depending on the porosity of the bone 103, the configuration of the woven retention device 100, and the characteristics of the fastener 102.

Figure 5A:
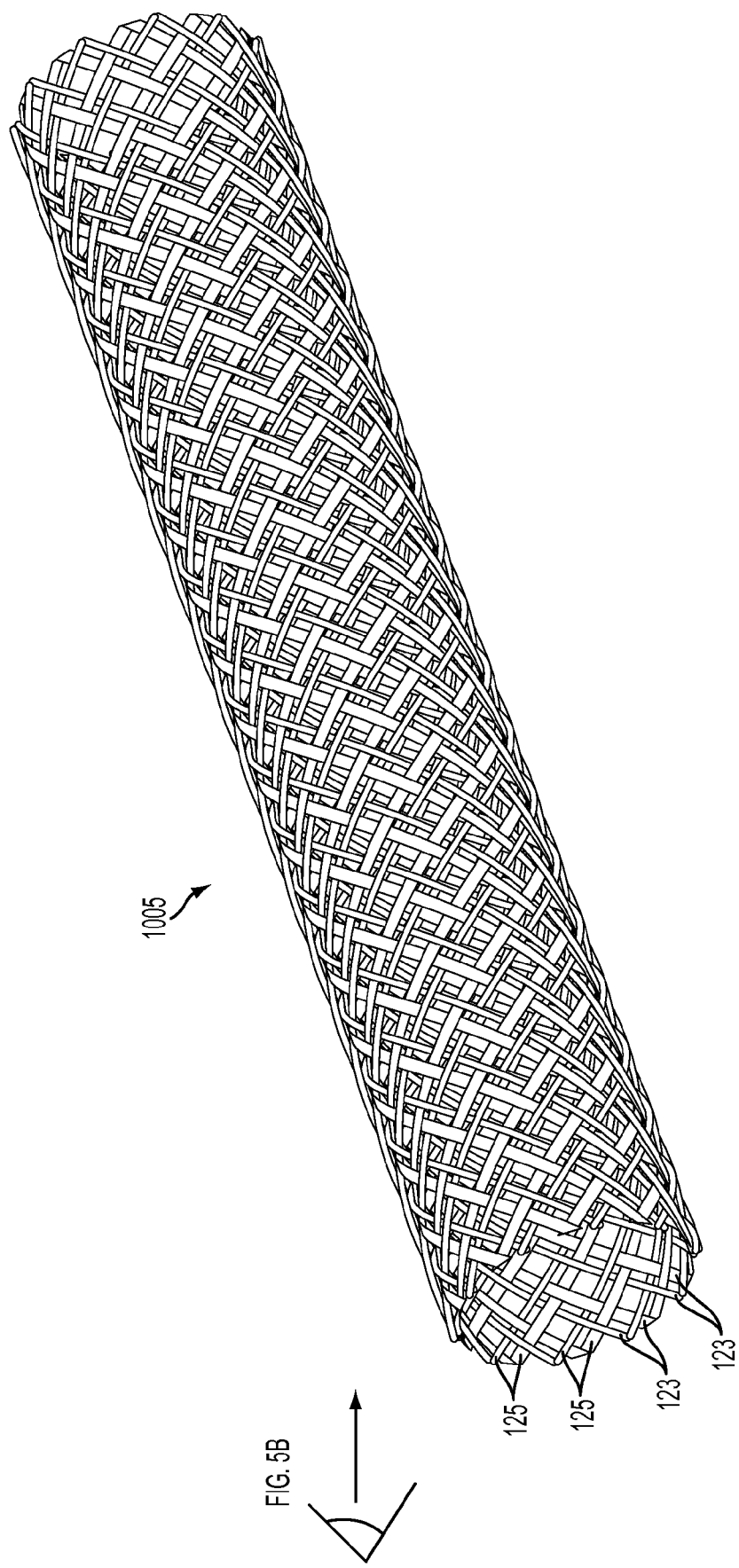
FIG. 5A shows an illustration of a woven retention device, according to an embodiment of the present invention.

FIG. 5A shows a woven retention device 1005 according to an embodiment of the invention. In this embodiment, the interwoven filaments of the woven retention device 100 can include a first plurality 123 of sets of filaments 120 (FIG. 6) that runs in a first helical direction and a second plurality 125 of sets of filaments 122 (FIG. 6) that runs in a direction intersecting the first plurality 123 of sets of filaments. As seen in FIG. 5A, each intersection of the first plurality 123 of sets of filaments with the second plurality 125 of sets of filaments may result in an arrangement of one or more cross-section geometries. At every other intersection along a particular set of either one of the first or second plurality 123, 125 of sets of filaments, the arrangement of the one or more cross-section geometries has a substantially same arrangement of cross-section geometries, and at other intersections along that set of either one of the first or second plurality 123, 125 of sets of filaments, there is a substantially different arrangement of cross-section geometries.

In one embodiment, the sets of filaments have a degree of stability and rigidity to form a tubular lattice in the relaxed state. The flexibility and stability of the tubular lattice may be such that the woven retention device 100 is able to return to an initial state from a deformed state. The deformed state may be the result of the woven retention device being in compression or tension either radially or longitudinally, and the deformation may be elastic deformation.

Figure 5B:
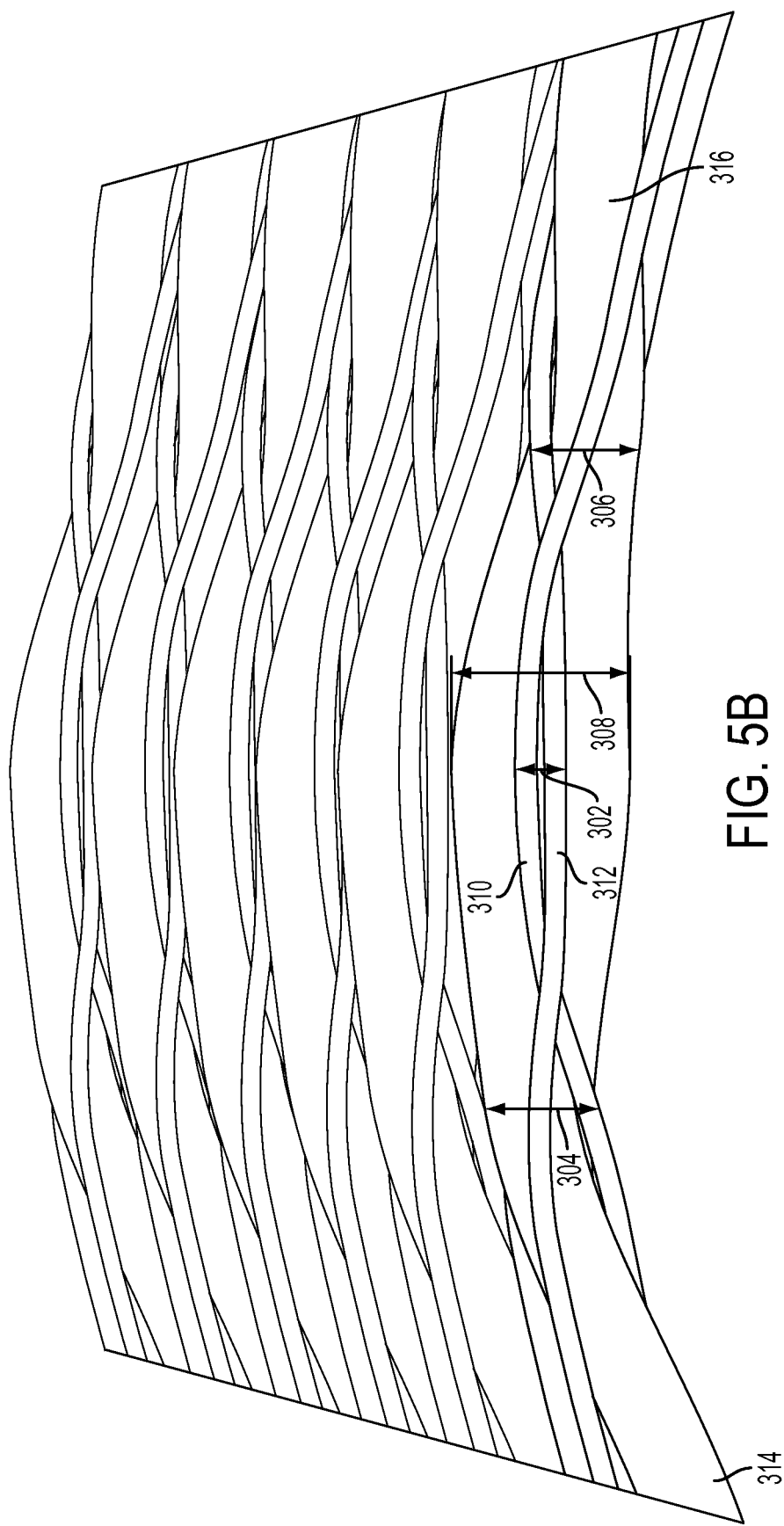
FIG. 5B shows a slanted sectional slice of FIG. 5A.

FIG. 5B shows one embodiment of the plurality of combinations of filament cross-section geometries forming a plurality of protuberance geometries of the retention device shown in FIG. 5A. The geometries may include, for example, shape, configuration, arrangement, and/or thickness of the filament(s) and/or the protuberance(s). For example, a first thickness 302 represents the thickness of an intersection of two filaments 310, 312, each having a relatively small thickness. In some embodiments, this intersection maybe formed by monofilament 310 overlapping another monofilament 312. In one embodiment, monofilament 310 can have a same diameter as monofilament 312. However, in another embodiment, the monofilament 310 can have a different diameter than monofilament 312.

Further, a second thickness 304 represents the thickness of an intersection of two filaments 310, 314, the filament 310 having a relatively small thickness and the filament 314 having a relatively large thickness. In some embodiments, this intersection may be formed by a multifilament (310) overlapping a monofilament (314). In another embodiment, filament 310 can be a monofilament having a smaller diameter than monofilament 314. Thus, in another embodiment, intersection 304 can be formed by a monofilament 310 overlapping a monofilament 314.

A third thickness 306 represents the thickness of an intersection of two filaments 312, 316. In an embodiment, this intersection may be formed by a multifilament (312) over a monofilament (316). In another embodiment, filament 312 can be a monofilament having a thinner diameter than monofilament 316. Thus, in another embodiment, the third thickness 306 can be formed by an intersection of monofilament 312 overlapping monofilament 316. The thicknesses 304 and 306 may have a same thickness if the filaments 310 and 312 have a same thickness, and the filaments 314 and 316 have a same thickness. Alternatively, the thicknesses of filaments 310 and 312 may be different, and the thickness of filaments 310 and 312 may be different, while the thicknesses 304 and 306 may be the same or different.

Next, a fourth thickness 308 represents the thickness between two relatively thick filaments 314, 316. In an embodiment, this intersection may be formed by a monofilament 314 overlapping a monofilament 316. Thus, each of the protuberance geometries and/or thicknesses 302, 304, 306, 308 allow for interfacing with the fastener on one side and the bone on the other side, and distributing pressure outwardly from the fastener to the bone in a distributed manner. In one embodiment, monofilament 314 can have a same diameter as monofilament 316. However, in another embodiment, the monofilaments 314, 316 can have different thicknesses.

As described above, protuberances on the interior surface of the woven retention device interface with the fastener and the protuberances of the exterior surface of the woven retention device interface with the bone surface. According to the varying protuberance thicknesses described above, the tubular lattice of the woven retention device 100 may have an outer radius spanning from a furthest outwardly extending protuberance in the radial direction on the exterior surface of the tubular lattice to a center point and/or central axis of the tubular lattice, the tubular lattice having an inner radius spanning from a furthest inwardly protruding protuberance in the radial direction on the interior surface of the tubular lattice to the center point of the tubular lattice. The tubular lattice may have an average radius that is an average between the outer radius and the inner radius. In one embodiment, the outer radius of the woven retention device 100 is greatest at the cross-section geometries that have the greatest protuberance thicknesses. Further, the inner radius of the woven retention device 100 may be the smallest at the cross-section geometries that have the largest protuberance thicknesses.

In one embodiment in a relaxed state, distributed protuberances on the outer surface can have more than two different heights in relation to the distance from a center point of the cross-section of the tubular lattice to peaks of the distributed protuberances on the exterior surface. Further, the distributed protuberances on the exterior surface can have more than two different angles of protrusions, or amplitudes, where the amplitude of a monofilament overlying a monofilament has a higher amplitude than where the monofilament overlies a multifilament. Further, the angle, protrusion, and/or curvature of the multifilament overlying a monofilament is greater than that of a multifilament overlying a multifilament because the variance or the steepness of the curve of the multi-filament is greater. The filaments, density, and/or pick count, for example, can contribute to the difference in the sharpness, angle and/or amplitude of the protrusions. The more pronounced the protrusion, the sharper the protrusion can be considered. Various relationships between the diameter of the retention device, the thickness of the first filament(s) and, the thickness of the overlying filament(s), and the weave pattern contribute to the resulting protuberances and protuberance geometries. Varying the protuberances and protuberance geometries can provide for woven retention devices having predetermined protuberances that accommodate various bony structures. The different heights and angles of distributed protuberances on the exterior surface can allow for interdigitation with bone surfaces, especially if the bone surface is irregularly shaped.

In a second state when a fastener is inserted into the tubular lattice, pressure from the fastener can be transmitted to the tubular lattice such that at least one of (i) the heights of the protuberances on the exterior surface, (ii) the amplitudes of the protuberances on the exterior surface, and (iii) the ratio of the height to the average radius, can change to accommodate deviations in the bone surface.

Figure 6:
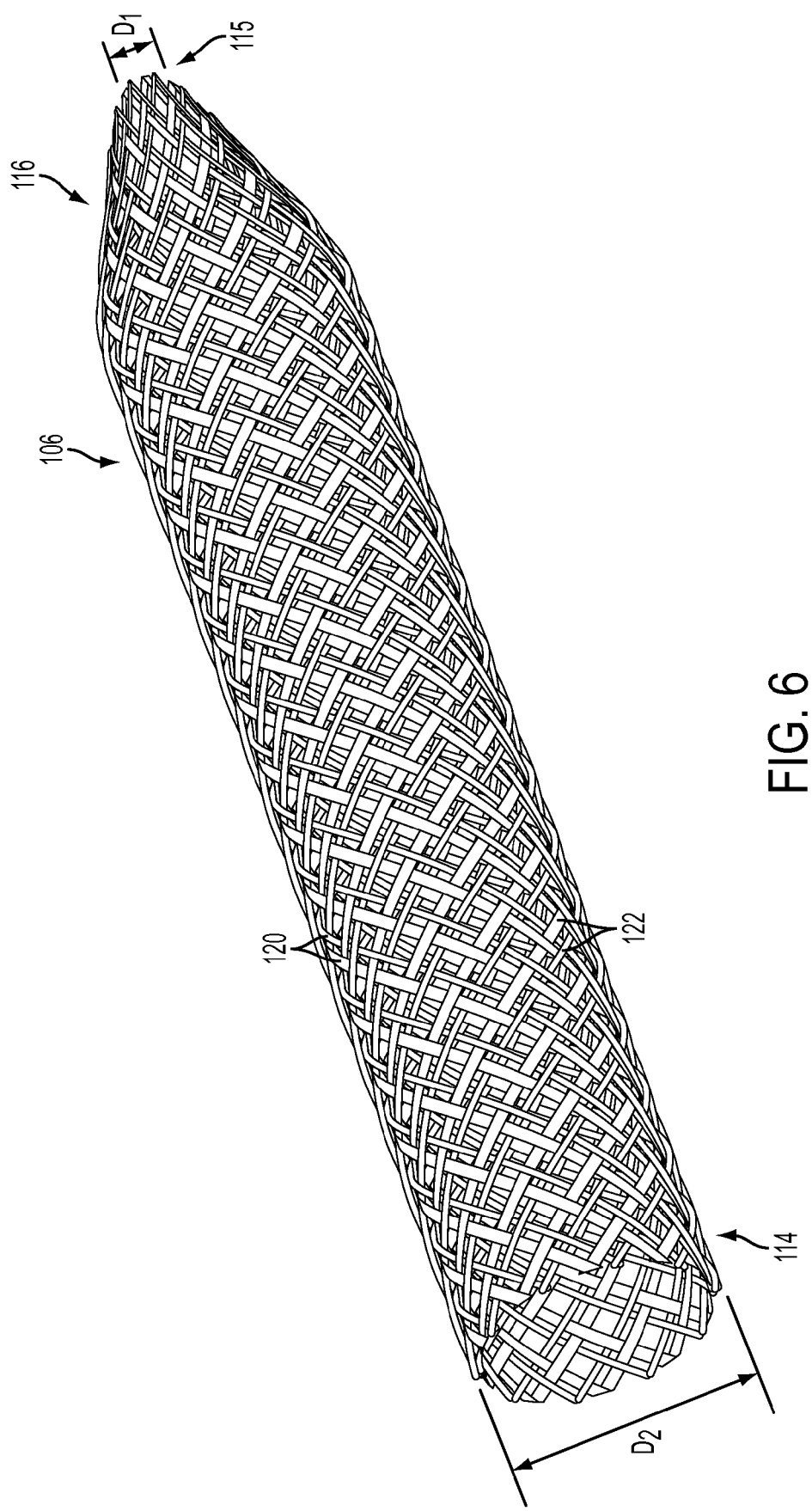
FIG. 6 shows an illustration of a woven retention device having a tapered end, according to an embodiment of the present invention.
Figure 7:
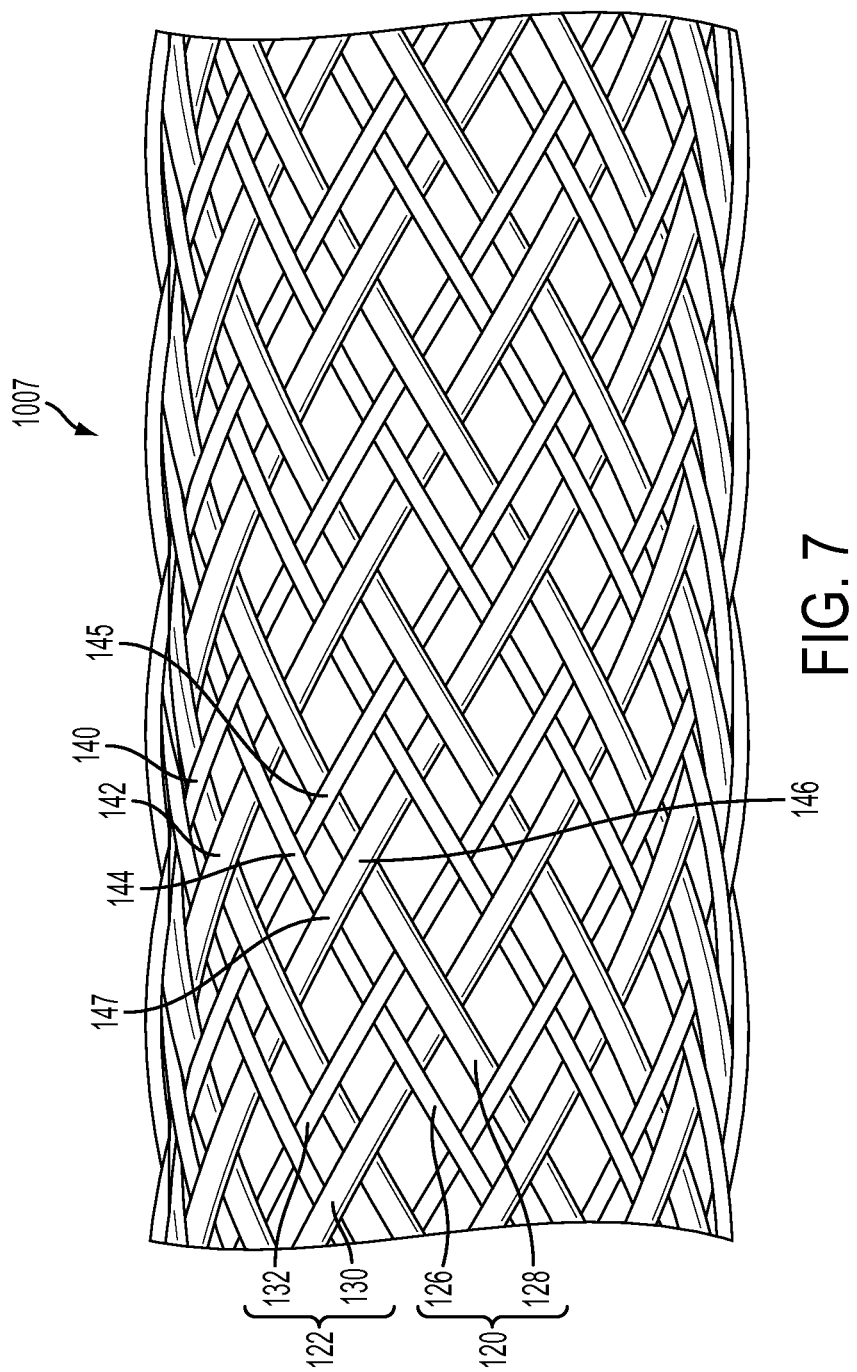
FIG. 7 shows a two-over/two-under monofilament/monofilament weave of a woven retention device, according to an embodiment of the present invention.

FIG. 6 shows a woven retention device according to an embodiment where a distal end 116 of the woven retention device 100 has a distal tip 115 with a first diameter $D_1$, and the receiving portion has a second diameter $D_2$ that is greater than the first diameter $D_1$. In one embodiment, a diameter $D_2$ of the proximal end 114 is substantially same as a diameter of the sleeve body 106. In contrast to FIG. 5A, the embodiment shown in FIG. 6 may have the distal end 116 tapered. For example, a set 120 of the first plurality 123 of sets of filaments includes a monofilament 126 and a monofilament 128 (as shown in FIG. 7). A set 122 of the second plurality 125 of sets of filaments includes a monofilament 132 and a monofilament 130 (as shown in FIG. 7).

According to an embodiment, the woven retention device 100 can include up to ten sets of filaments in each of the first and second plurality 123, 125 of sets of filaments. In another embodiment, for each of the first and second plurality 123, 125 of sets of filaments, the woven retention device 100 can include at least two sets of filaments. Thus, each of the sets of filaments may have a degree of flexibility that allows for expandability of the woven retention device 100. The filament properties and characteristics can be varied, and the number of filaments used in the weave contributes to the stability and/or rigidity of the woven retention device. For example, a small-sized woven retention device may include a half set of filaments such as 12 filament in one direction and 12 in the other direction. Whereas, a larger size may weave 24 filaments and 24 filaments. Depending upon the size of the woven retention device, a range of the quantity of filaments can vary from 2/2 to 36/36. For example, the quantity of filaments can be 8/8, 10/10, 12/12, 24/24 and/or 36/36, according to some embodiments. Additionally, other filament quantities are also possible. An even number of filaments and bobbins are contemplated, resulting in a symmetrical pattern. But an odd number of filaments can be utilized as well and would result in a non-symmetrical pattern.

FIG. 7 shows a close-up of the woven retention device 1007 according to an embodiment having a combination of different filaments. The filaments can be of different shapes and diameters. For example, the filaments can be a combination of round filaments and flat filaments, or all flat filaments, or all round filaments. The shapes of the filaments are not limited to flat and round, however, and may also include rectangular, triangular, and elliptical shapes, or other cross-section shapes. As shown in FIG. 7, the woven retention device has flat multifilaments 142 and round monofilaments 140. In another embodiment, filament 142 can be a monofilament having a different or the same diameter as monofilament 140. In another embodiment, the flat multifilaments 142 have a larger width than height. In one embodiment, the round monofilaments 140 can have a substantially circular cross-section. In one embodiment, the round monofilaments 142 can have a substantially circular cross-section. According to some embodiments, the thickness of the monofilaments 140 is greater than the thickness of the multifilaments 142. According to the combinations of different filaments used, different types of filament intersections can be provided. For example, each of intersections 144, 145, 146, and 147 can comprise a different arrangement and/or combination of filaments, as discussed further below.

As shown in FIG. 7, a set 120 of the first plurality 123 of sets of filaments includes a set 120 including a monofilament 126 and a monofilament 128 having different or the same diameters. In another embodiment, the set 120 of the first plurality 123 of sets of filaments can include a monofilament and a multifilament. A set 122 of the second plurality 125 of sets of filaments includes a monofilament 132 and a monofilament 130 having the same or different diameters. In another embodiment, the set 122 of the second plurality 125 of sets of filaments can include a monofilament and a multifilament.

Figure 8:
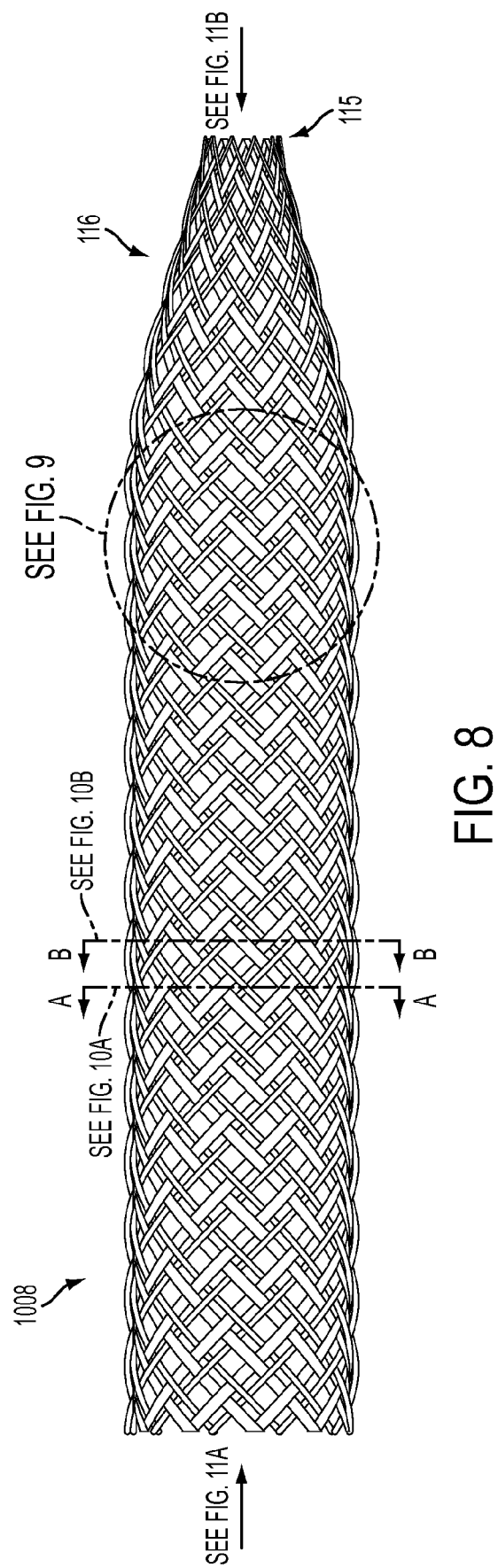
FIG. 8 shows a woven retention device with a tapered end along its longitudinal axis, according to an embodiment of the present invention.

FIG. 8 shows the woven retention device 1008 with a tapered distal end 116 along its longitudinal axis.

Figure 9:
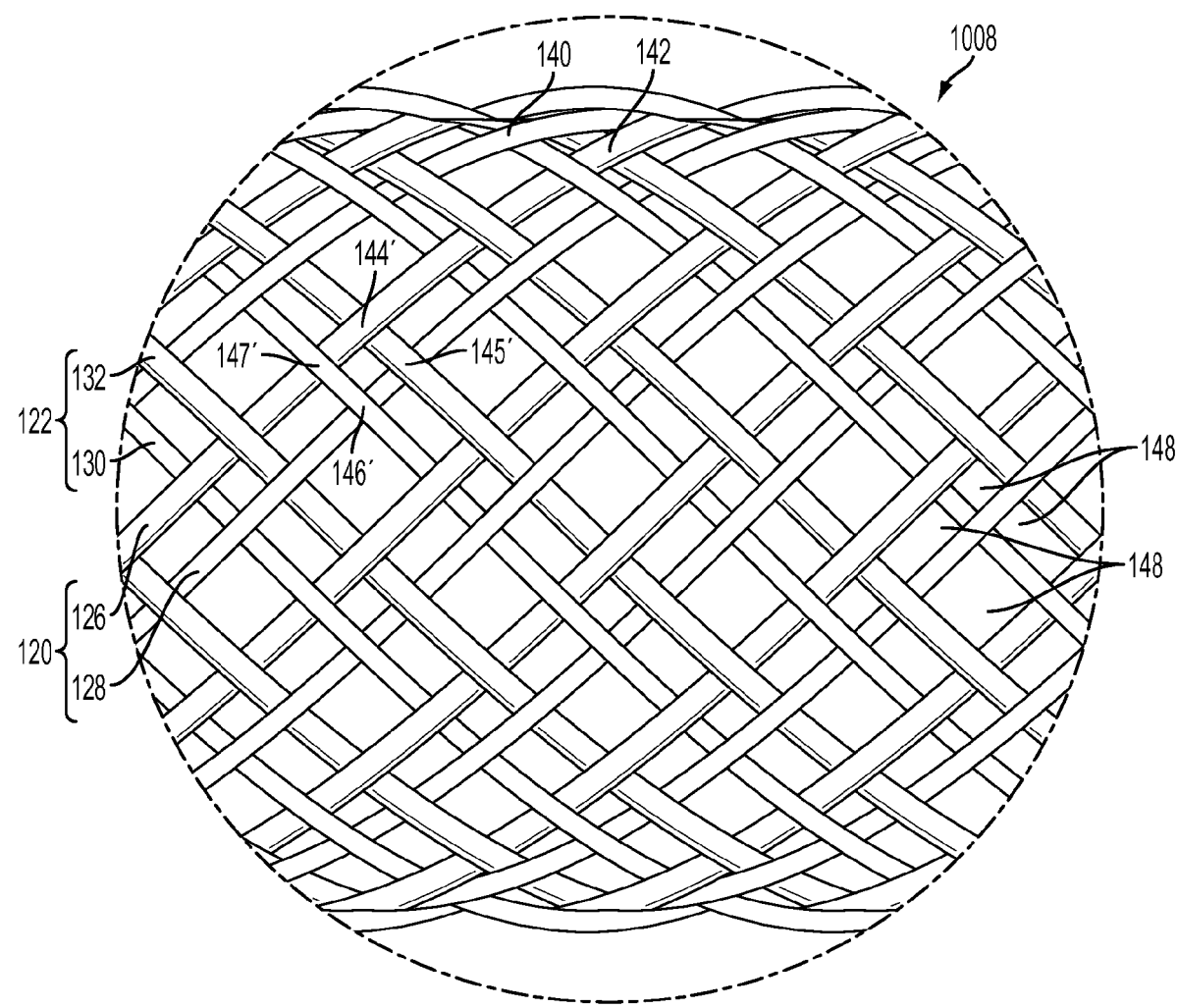
FIG. 9 shows a close-up view of a portion of the woven retention device shown in FIG. 8.

FIG. 9 shows a close-up view of the woven retention device 1008 of FIG. 8, according to one embodiment. As explained below, a set of filaments can include one or more filaments. In one embodiment, a set of filaments can include filaments that are side by side and the filaments including an inner filament and an outer filament. The inner filament in one embodiment can be disposed on the left of the outer filament, as viewed facing the receiving portion in a longitudinal direction. For example, FIG. 9 shows one embodiment of a woven retention device 1008, wherein each of the first plurality 123 (FIG. 5A) of sets of filaments 120 includes a first inner filament 126 and a first outer filament 128, and each of the second plurality 125 (FIG. 5A) of sets of filaments 122 includes a second inner filament 132 and a second outer filament 130. In one embodiment, one of the outer filaments and the inner filaments can be a round monofilament 140 and one of the outer filaments and the inner filaments can be a flat multifilament 142. However, in another embodiment, filament 142 can be a round monofilament with a different or a same diameter as monofilament 140. In one embodiment, the woven retention device 1008 is configured such that the plurality of interwoven filaments are comprised of alternating round monofilaments and flat multifilaments. In this embodiment, each of the sets of filaments can have a consistent and uniform order of filaments, which allows for a uniform arrangement of protuberances. In another embodiment, the plurality of interwoven filaments are comprised of alternating round monofilaments of a first diameter and round filaments of a second diameter that is greater than or less than the first diameter.

As shown in FIG. 9, in one embodiment, the first inner filament 126 can be a flat multifilament 142, the first outer filament 128 can be a round monofilament 140, the second inner filament 132 can be a flat multifilament 142 and the second outer filament 130 can be a round monofilament 140. In another embodiment as shown in FIG. 7, the first inner filament 126 can be a round monofilament 140, the first outer filament 128 can be a flat multifilament 142 and the second outer filament 130 can be a flat multifilament 142 and the second inner filament 132 can be a round monofilament 140. In another embodiment, the first inner filament 126 can be a flat multifilament 142 and the first outer filament 128 can be a flat multifilament 142 while the second outer filament 130 can be a round monofilament 140 and the second inner filament 132 can be a round monofilament 140.

In alternate embodiments, the first inner filament 126 can be a round monofilament 142, the first outer filament 128 can be a round monofilament 140 having the same or different diameter as monofilament 142, the second inner filament 132 can be a round monofilament 142 and the second outer filament 130 can be a round monofilament 140 having a same or different diameter as round monofilament 142.

Each of the different monofilament/multifilament arrangements allow for the protuberances to occur at different regions. In FIG. 9, the protuberances form a diamond arrangement shown by the shape defined by intersection points 144', 145', 146', and 147'. For example, as shown in FIG. 7, the first inner filament 126 and the second outer filament 130 being monofilaments results in a pronounced protuberance (e.g., a protuberance having the thickness 308 in FIG. 5B) to occur at a top intersection point 144 of a diamond arrangement of the combination of intersections, the diamond arrangement being defined by the shape outlined by intersection points 144, 145, 146, and 147. On the other hand, as shown in FIG. 9, having the first outer filament 128 and the second outer filament 130 being monofilaments results in a pronounced protuberances to occur at a bottom 146' of a diamond arrangement of the combination of intersections, the diamond arrangement being defined by the shape outlined by intersection points 144', 145', 146', and 147'.

As can be seen from FIG. 9, the woven retention device 1008 can be configured so that the plurality of interwoven filaments follow a two-under/two-over configuration, where each of the filaments overlie two intersecting filaments and underlie two intersecting filaments. In another embodiment, at each intersection point, a round monofilament either overlies both of the intersecting filaments or is overlain by both of the intersecting filaments and the flat multifilament overlies one of the intersecting filaments and is overlain by the other of the intersecting filaments. However, other contemplated embodiments include a one-over-one weave provided that there is sufficient rigidity and flexibility of the filaments to generate the protuberances.

Alternative weaving patterns besides the two-over/two-under configuration are also contemplated within the broad inventive principles disclosed herein. A one-over/one-under configuration is contemplated where each filament alternatingly overlies and underlies an intersecting filament. In one embodiment, a three-over/three-under weave pattern is contemplated where each filament overlies three intersecting filaments before underlying three intersecting filaments. In another embodiment, a two-over/one-under is contemplated where each filament overlies two intersecting filaments and then underlies one intersecting filament. Alternatively, a one-over/two-under arrangement is also possible where a filament overlies one intersecting filament before underlying two intersecting filaments. In another embodiment, a three-over/one-under is contemplated where each filament overlies three intersecting filaments and then underlies one intersecting filament. Alternatively, a one-over/three-under arrangement is also possible where a filament overlies one intersecting filament before underlying three intersecting filaments. With each of these weaving patterns, sufficient stability, rigidity, compressibility, sheer strength, and/or tensile strength can allow for the pressure from the fastener is able to transmit force in a distributed manner to the bone surface.

Figure 10A:
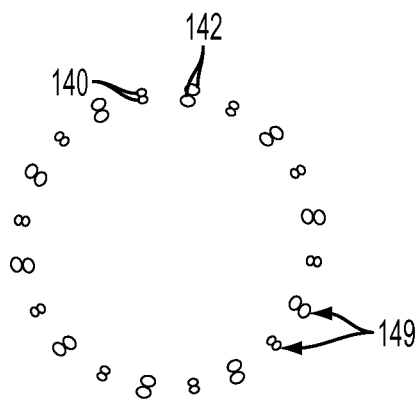
FIG. 10A shows a cross-sectional view along line A-A in FIG. 8 of the woven retention device.
Figure 10B:
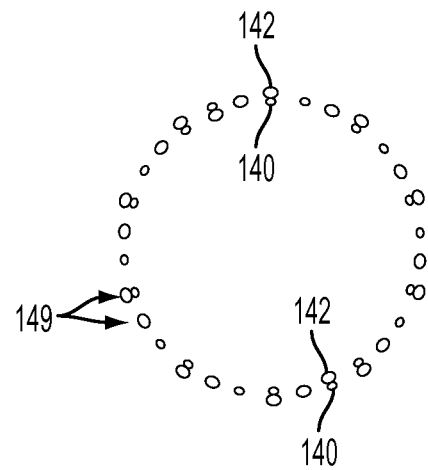
FIG. 10B shows a cross-sectional view along line B-B in FIG. 8 of the woven retention device.

FIGS. 10A and 10B show cross sections showing the intersecting filaments of the woven retention device 1008, representing various cross-sectional geometries 149 at the sections A-A and B-B indicated in FIG. 8. The woven device 1008 can be configured as shown such that the intersecting sets of filaments form a plurality of cross-sectional geometries and/or thicknesses. In FIG. 10A, section A-A of FIG. 8, the large round over round grouping represents the intersection of a relatively large round monofilament 142 over another relatively large round monofilament 142. The cross-sections of these relatively large round monofilaments 142, 142 can be the same or have different thicknesses from each other. On the other hand, the smaller round-over-round grouping represent a relatively small round monofilament 140 over another relatively small round monofilament 140 intersection where the round monofilaments 140, 140 can have the same or different thicknesses from each other. In FIG. 10B, section B-B of FIG. 8, the large circle over the small circle grouping represents a round monofilament 142 over a round monofilament 140 where the diameter of round monofilament 142 is greater than round monofilament 140. Further, a small circle over large circle cross-section geometry represents a round monofilament 140 over a round monofilament 142 where the diameter of the round monofilament 140 is smaller than round monofilament 142.

The round monofilaments of the woven retention device can have differing diameters. In one embodiment, the round monofilaments can have a diameter in a range of about 0.1 mm-0.4 mm. In one embodiment, the round monofilament of the woven retention device is 0.2 mm.

The multifilaments of the woven retention device according to some embodiments can have various thicknesses and widths. For example, a multifilament may have a thickness of less than 0.1 mm. The cross-sectional shape, e.g., flat or round, and the texture, for example, of the multifilaments can also be relevant. The number of filaments and pattern can also be relevant. As such, with those considerations, various filament linear mass densities can be contemplated. For example, the multifilaments can have a linear mass density in a range of about 150-250 denier. In one embodiment, the multifilaments can have a linear mass density of about 200 denier.

The woven retention device can be configured such that the intersecting sets of filaments form a plurality of differently shaped and differently sized interstices. In one embodiment, as shown in FIG. 9, the first inner and outer filaments of one set of first filaments can be grouped closer to each other than the other sets of first filaments. Likewise, the second inner and outer filaments of one set of second filaments can be grouped closer to each other than the other sets of second filaments. When the two sets of filaments intersect, as shown in FIG. 9, the area which is outlined by the first and second plurality of sets of filaments is a plurality of differently shaped and differently sized interstices 148. By having differently shaped and sized interstices, a more conducive environment for non-uniform bony surface can allow for ingrowth of bone to occur. Additionally, improved interdigitation with the bony structure can be achieved with a combination of the interstices and protuberances.

Figure 11A:
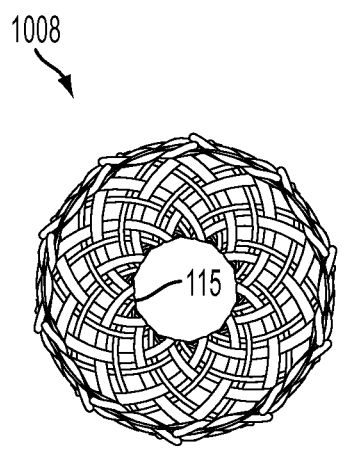
FIG. 11A shows an end view of the woven retention device of FIG. 8 as seen from a non-tapered end view.
Figure 11B:
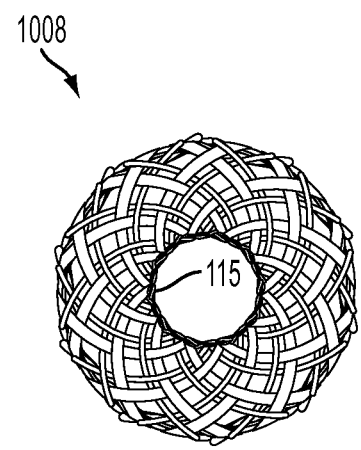
FIG. 11B shows an axial view of the woven retention device of FIG. 8 as seen from a tapered end view.
Figure 12A:
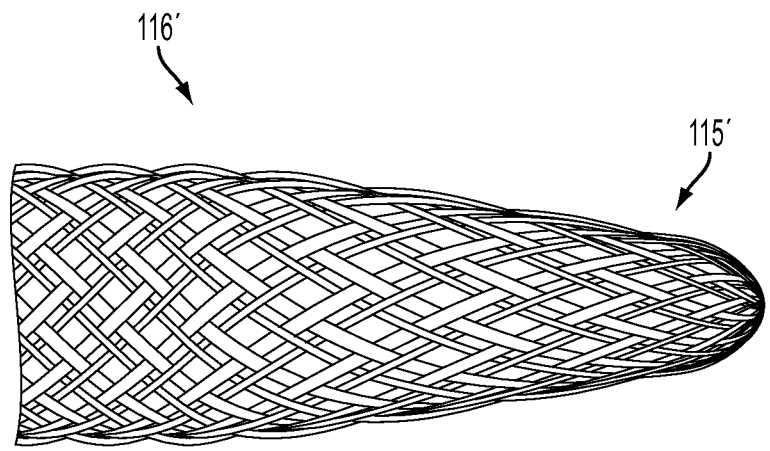
FIG. 12A shows a tapered end of a woven retention device having a closed end, according to an embodiment of the present invention.
Figure 12B:
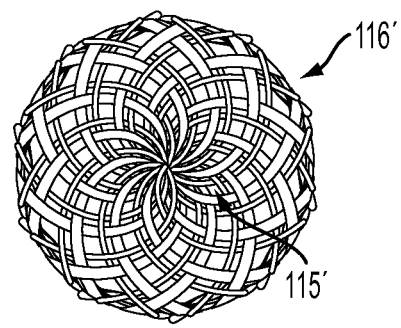
FIG. 12B shows a distal end view of the closed end of the woven retention device shown in FIG. 12A.

The tapering end portion can be seen from FIGS. 11A and 11B a front and rear axial direction of the woven retention device 1008, as indicated in FIG. 8. An edge of the distal tip 115 can be seen in FIGS. 11A and 11B from inner and outer sides, respectively, the distal end 116 (see FIG. 8). The tapered end can be used to facilitate inserting the woven retention device 1008 into a bone hole. In one embodiment, the tapered end can have at least a portion of the end be closed. As shown in FIGS. 12A and 12B, a distal end 116' of a woven retention device according to another embodiment has a distal tip 115' that can be closed to further allow for a push rod to push the woven retention device 100 into the hole. The closure of the end can be made (i.e., tip can be made) via knitting, energy (heat stake, laser, optical, ultrasound energy to melt fibers), and chemical (glue, or superglue).

Figure 13:
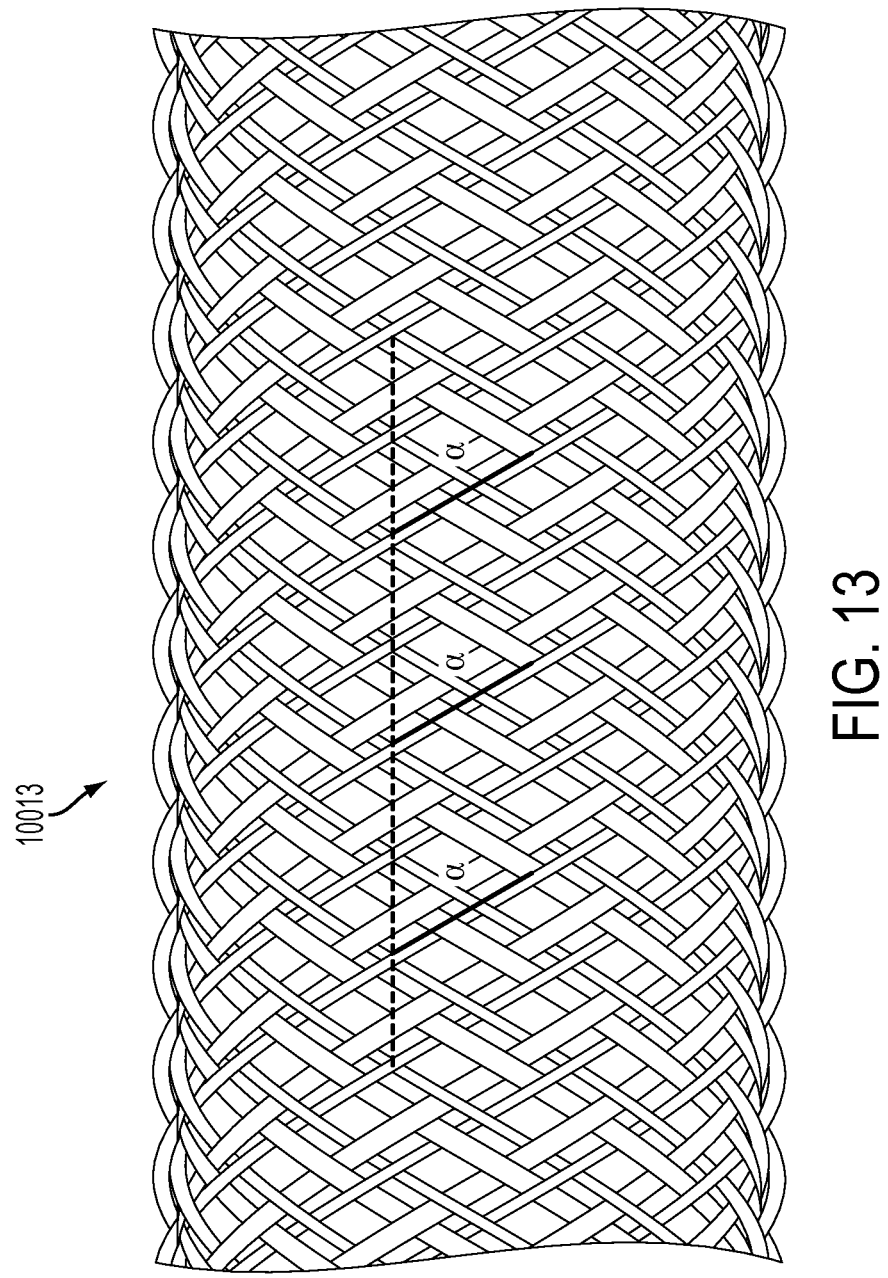
FIG. 13 shows a section of a woven retention device, illustrating a representative fiber angle, according to an embodiment of the present invention.

In FIG. 13, the interwoven filaments of a woven retention device 10013 extend around the tubular lattice in an angle range of α. In one embodiment, α can represent a range from about 40-60 degrees with respect to a longitudinal direction of the woven retention device. In another embodiment, α can represent a range from about 15-75 degrees with respect to a longitudinal direction of the body sleeve. In one embodiment, α represents 45 degrees. The retention device can, in the relaxed state, have the interwoven filaments that extend around the tubular lattice at about a 45 degree angle with respect to a longitudinal direction of the woven retention device. The configuration and angle α shown in FIG. 13 can correspond to a relaxed state of the woven retention device 100 according to some embodiments.

Figure 14:
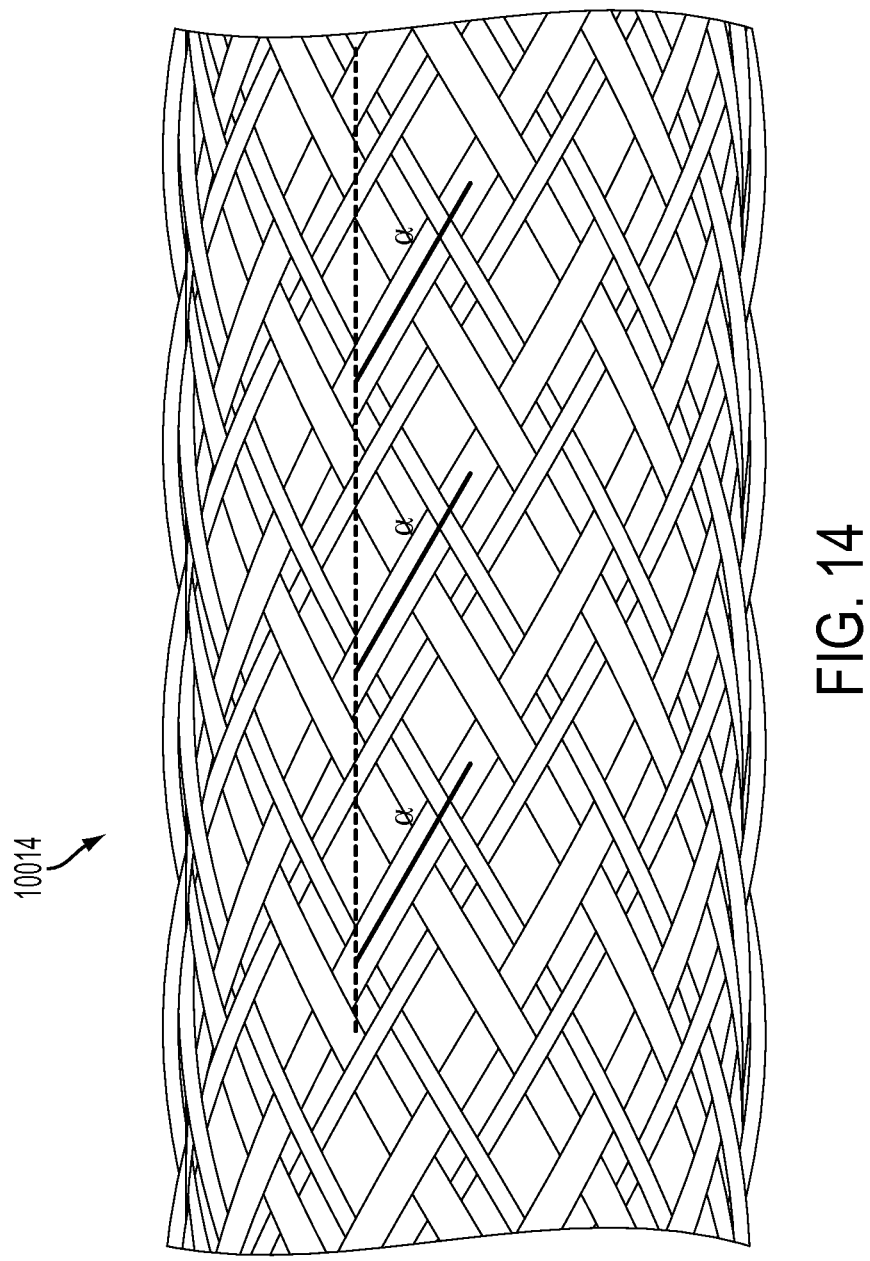
FIG. 14 shows a section of a woven retention device, illustrating another representative fiber angle, according to an embodiment of the present invention.

FIG. 14 shows that the braid angle α for a woven retention device 10014, according to another embodiment. The braid angle α can be smaller than 45 degrees. The configuration and braid angle α in FIG. 14 can also represent the woven retention device 10013 of FIG. 13 in a constricted state or if the woven retention device 10014 has a predetermined diameter lower than a predetermined value and the filaments exceed a predetermined thickness. For example, when the woven retention device has an average diameter of 2 mm, the braid angle α can be about 35 degrees.

Figure 15:
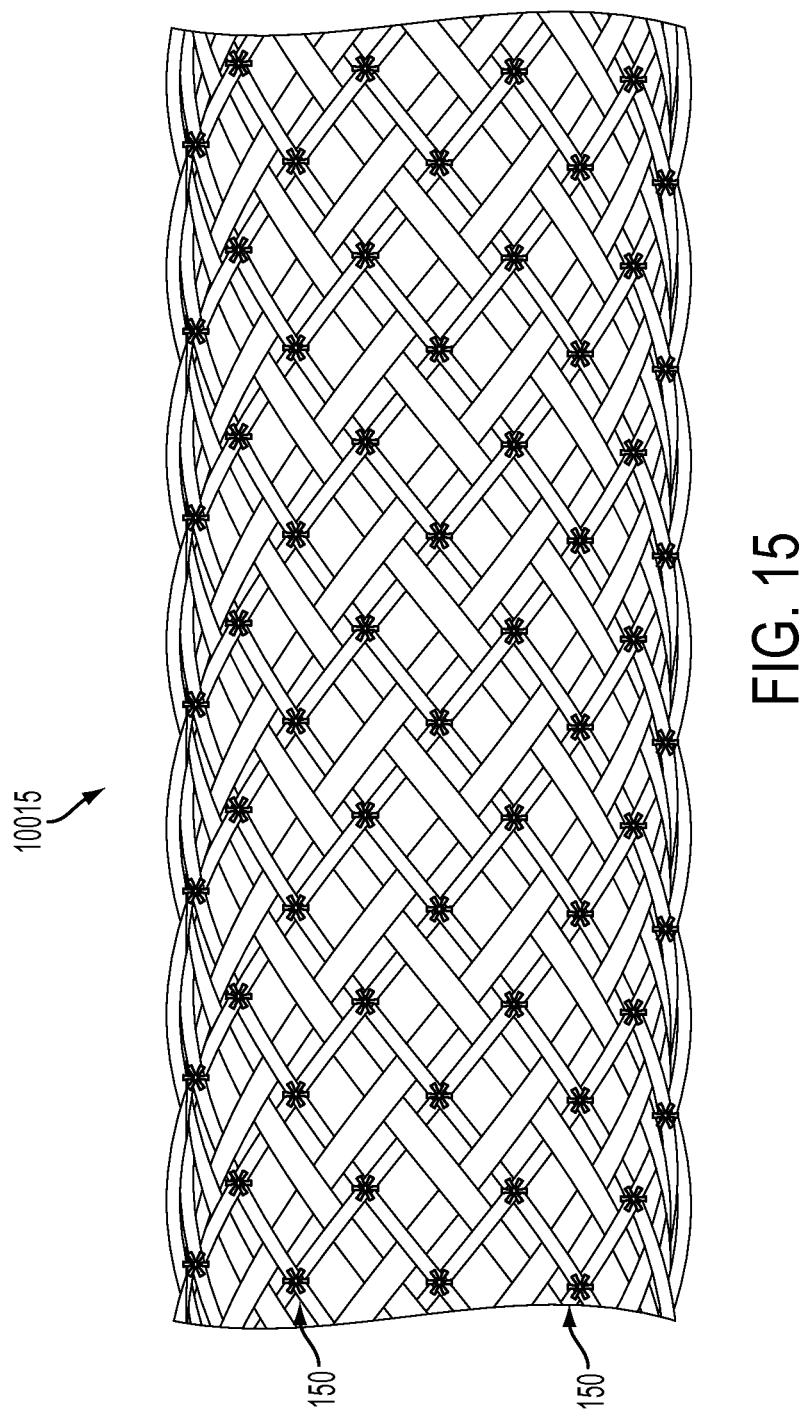
FIG. 15 shows a section of a woven retention device illustrating multiple locations and/or points of contact on an exterior surface of the woven retention device, according to an embodiment of the present invention.

FIG. 15 shows the distributed protuberances 150 on the exterior surface of the woven retention device 10015 according to an embodiment. The woven retention device 10015 can allow for a different loading pattern (dynamic load) than the screw because of uniform radial pressure. Instead of pushing or cutting bone, the screw can push on and deform the woven structure of the woven retention device 10015, which allows for a distributed force. Preferably, the woven structures can be of a strength to not be cut or broken by the screw. The interface can be in random or patterned contacts on the exterior surface and the interior surface. For example, FIG. 15 shows that the protuberances 150 are in a substantially diamond-shaped pattern grid distributed across the tubular lattice.

Figure 16A:
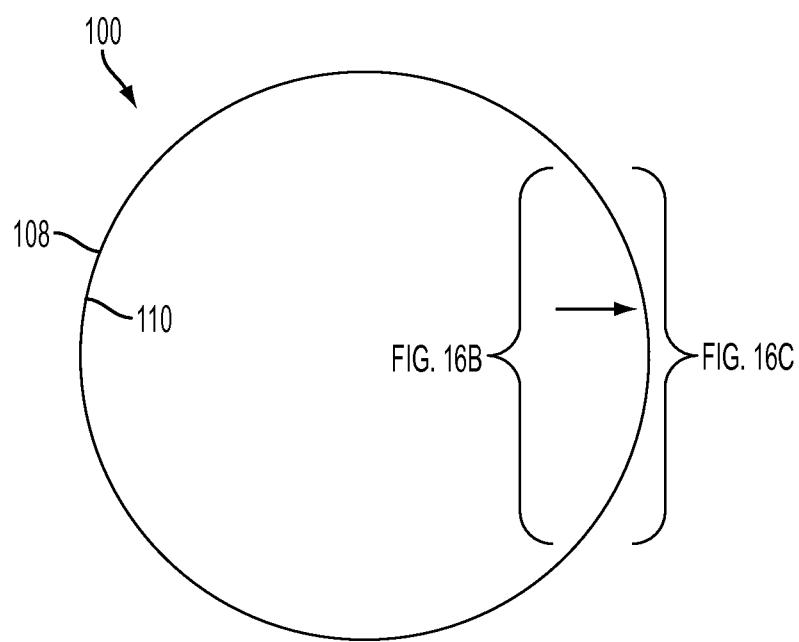
FIG. 16A shows a representation of a woven retention device with a force or pressure applied to a location and/or point on an inside of the retention device, according to an embodiment of the present invention.
Figure 16B:
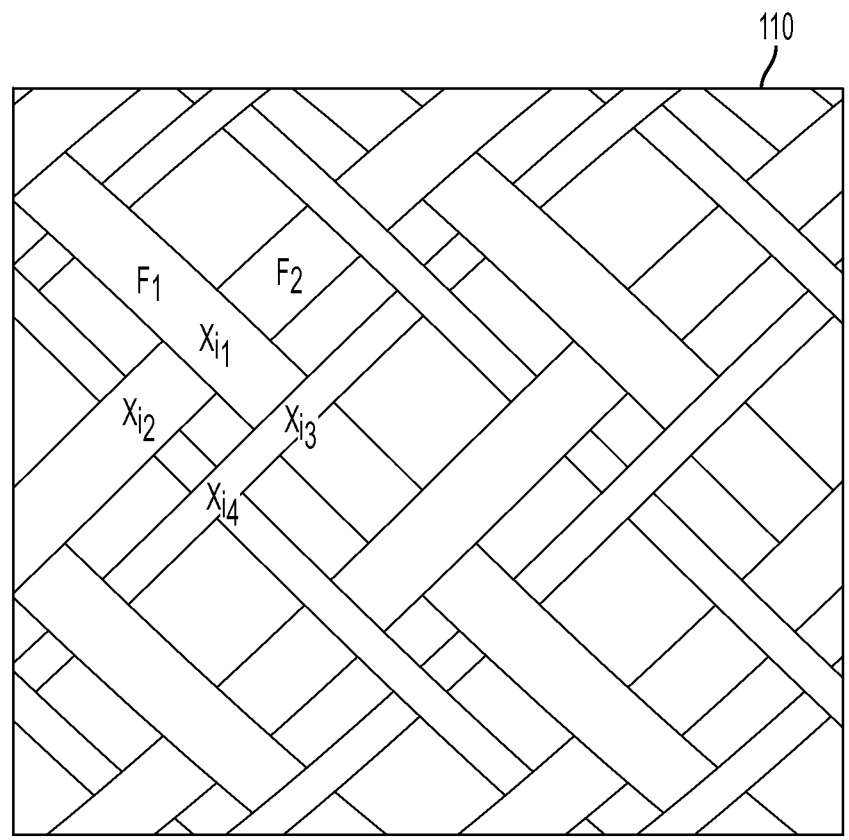
FIG. 16B shows a view of a region of an interior surface of the woven retention device at the point shown in FIG. 16A.
Figure 16C:
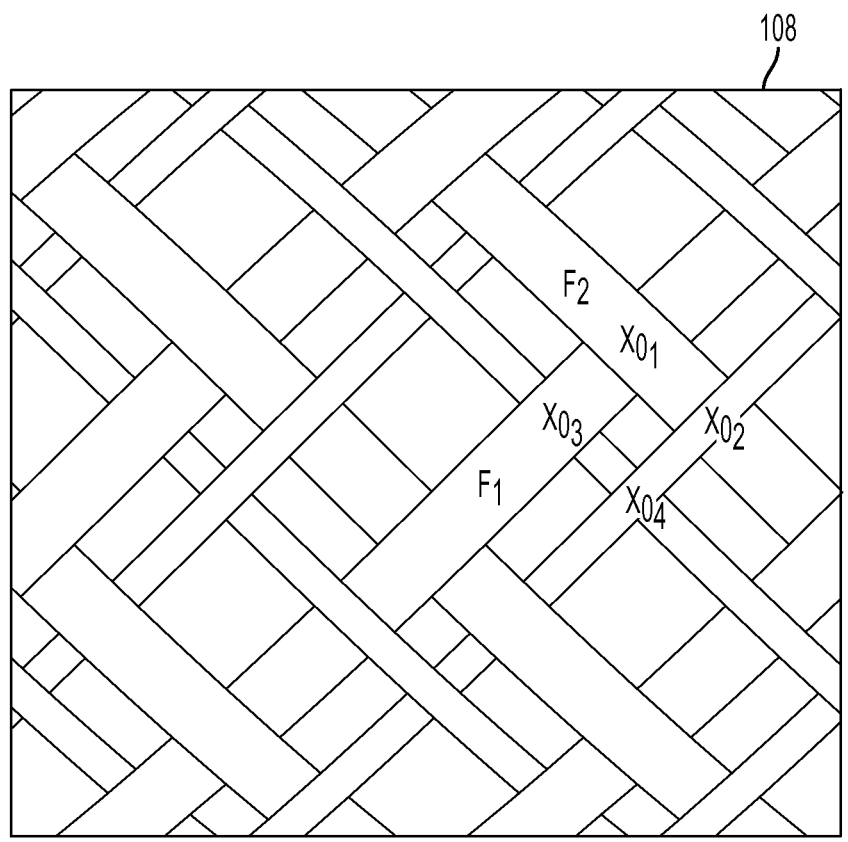
FIG. 16C shows a view of a region of an exterior surface of the woven retention surface at the point shown on FIG. 16A.

FIG. 16A is a cross-sectional schematic of the retention device (in the shape of a general circle) having an arrow representing a point of pressure contact on the interior surface 110 of the woven retention device 100. FIG. 16B represents a portion of the interior surface 110 covering the bracketed portion of FIG. 16A as viewed from inside the woven retention device 100. FIG. 16C represents a reverse view from that of FIG. 16B, and thus shows an outer surface as evidenced by bracket in FIG. 16A as viewed from outside of the woven retention device 100 looking in to the radial center. Intersections points $Xi_1$, $Xi_2$, $Xi_3$, and $Xi_4$ on the interior surface 110 in FIG. 16B respectively correspond to intersection points $Xo_1$, $Xo_2$, $Xo_3$, and $Xo_4$ on the exterior surface 108 in FIG. 16C.

As can be seen from FIGS. 16B and 16C, even though the left to right portions of the portion correspond to different regions of the woven retention device, the configuration of each portion can appear the same. That is, while an over/under weave on a left side of the interior surface can correspond to a under/over weave on a right side of the exterior surface, the left portion in a similar position as the left portion of the interior surface can resemble a similar configuration of the over/under weave. Each of the four Xi regions in FIG. 16B corresponds to a protuberance on the interior surface, and the filaments F1 and F2 can correspond to intersecting multifilaments. When viewed from the exterior surface, this same portion shows that the pressure is located on the right side of the portion. As can be seen, on the interior surface, filament F1 overlies filament F2 at intersection $Xi_1$, whereas on the exterior surface filament F2 overlies filament F2 at intersection $Xo_1$. However, in the left portion of the exterior surface, it resembles the left portion of the interior portion.

Figure 17A:
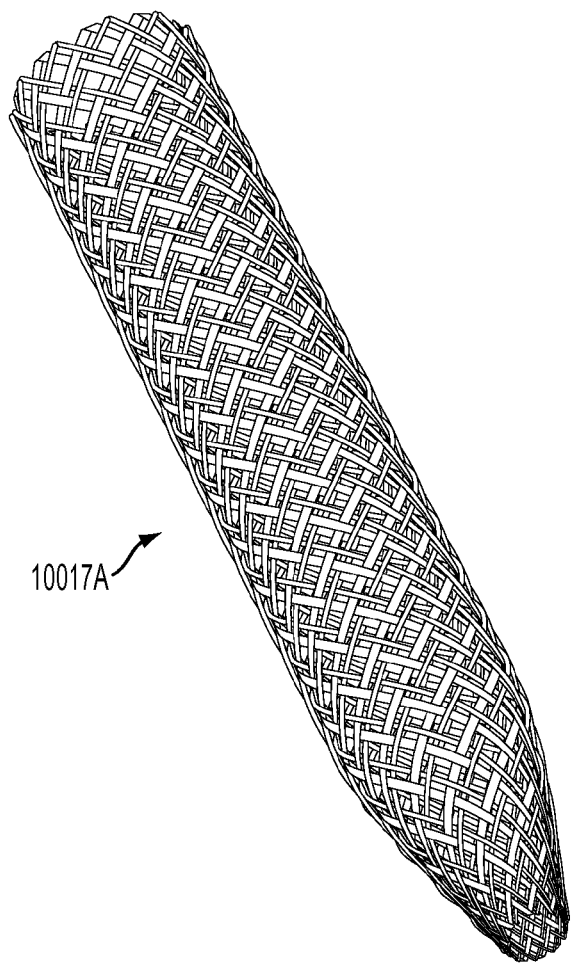
FIGS. 17A and 17B show perspective views of two woven retention devices each having different lengths, according to embodiments of the present invention.
Figure 17B:
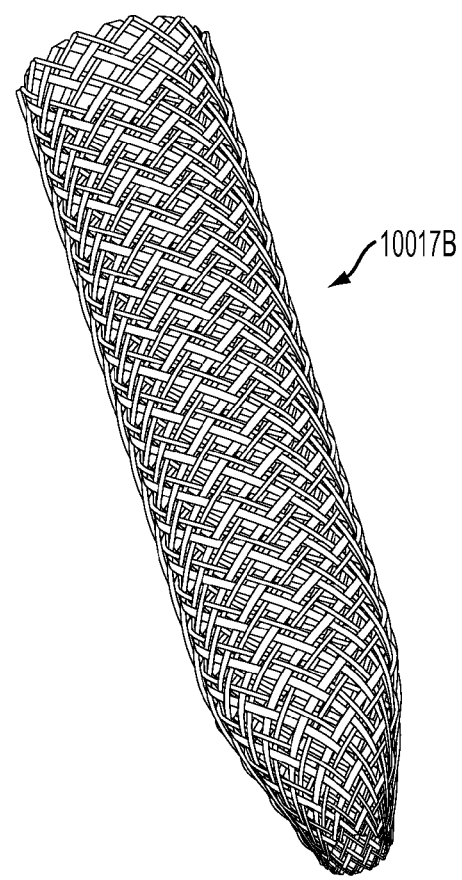
Figures 17C, 17D:
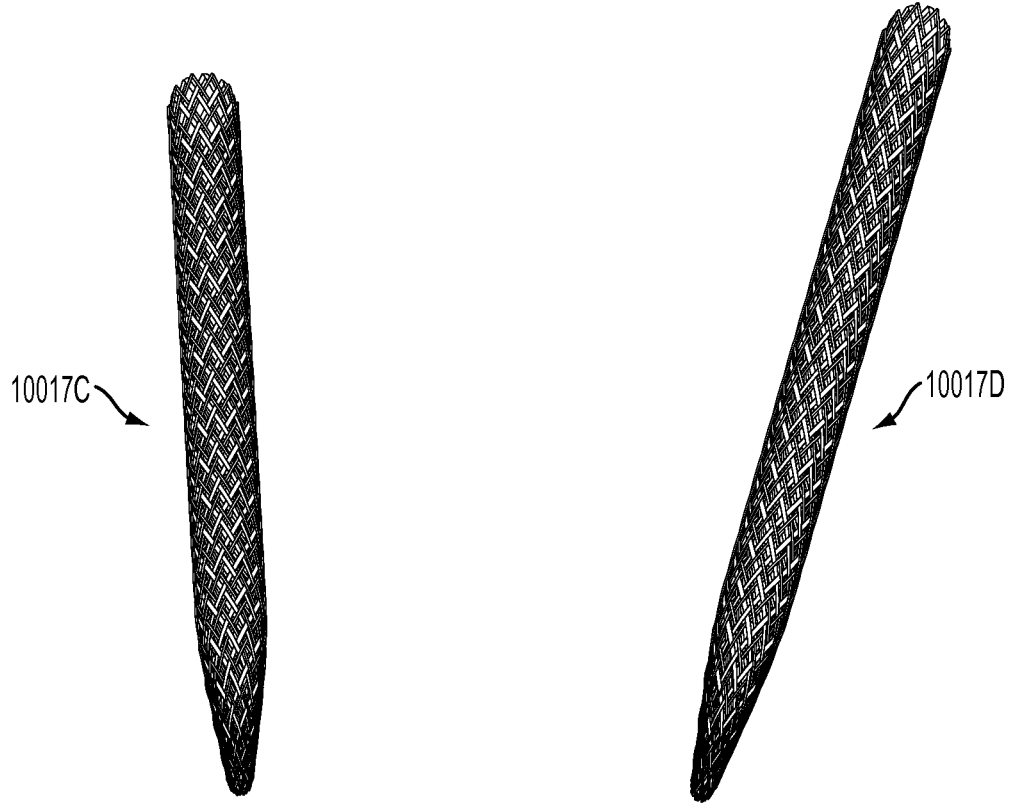
FIGS. 17C and 17D show two woven retention devices each having different lengths, according to embodiments of the present invention.

In a relaxed state, the woven retention device can be of various lengths and diameters. FIGS. 17A and 17B show that two differing lengths of embodiments of woven retention devices 10017A and 10017B, respectively. In one embodiment, the woven retention device can have a length in a range of about 30 mm to 40 mm. The length of the woven retention device can come in dynamically cuttable; and/or predetermined length, such as small—30 mm; medium—40 mm, large—40 mm, and other sizes (or ranges) are also possible. FIGS. 17C and 17D show two embodiments of woven retention devices 10017C and 10017D with differing lengths and each with a diameter that is different from FIGS. 17A and 17B. In one embodiment, the woven retention device can have a diameter of about 1.5 mm to 9.0 mm. The diameter of the woven retention device can come in predetermined sizes, such as (i) small: 2.0 mm fine (can accommodate 1.3 mm to a little over 2.0 mm pilot hole diameter and can fit 2.0 mm-2.7 mm screws); (ii) medium: 3.5 mm-6.0 mm course (can accommodate 2.4 mm to a little over 3.2 mm pilot hole diameters and can fit 3.5-6 mm screws); and (iii) large: 6.5 mm-9 mm very course (can accommodate 4.1 mm to a little over 5.9 mm pilot hole diameters and can fit 6.5-9.0 mm screws).

Figure 17E:
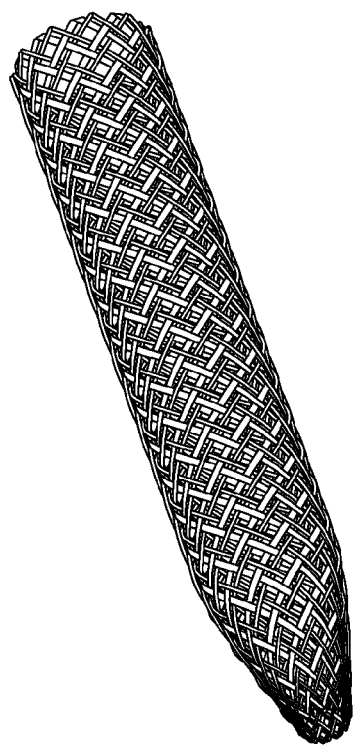
FIGS. 17E, 17F and 17G show a woven retention device in a relaxed state, in a stretched state, and in an implanted state, respectively, according to embodiments of the present invention.
Figure 17F:
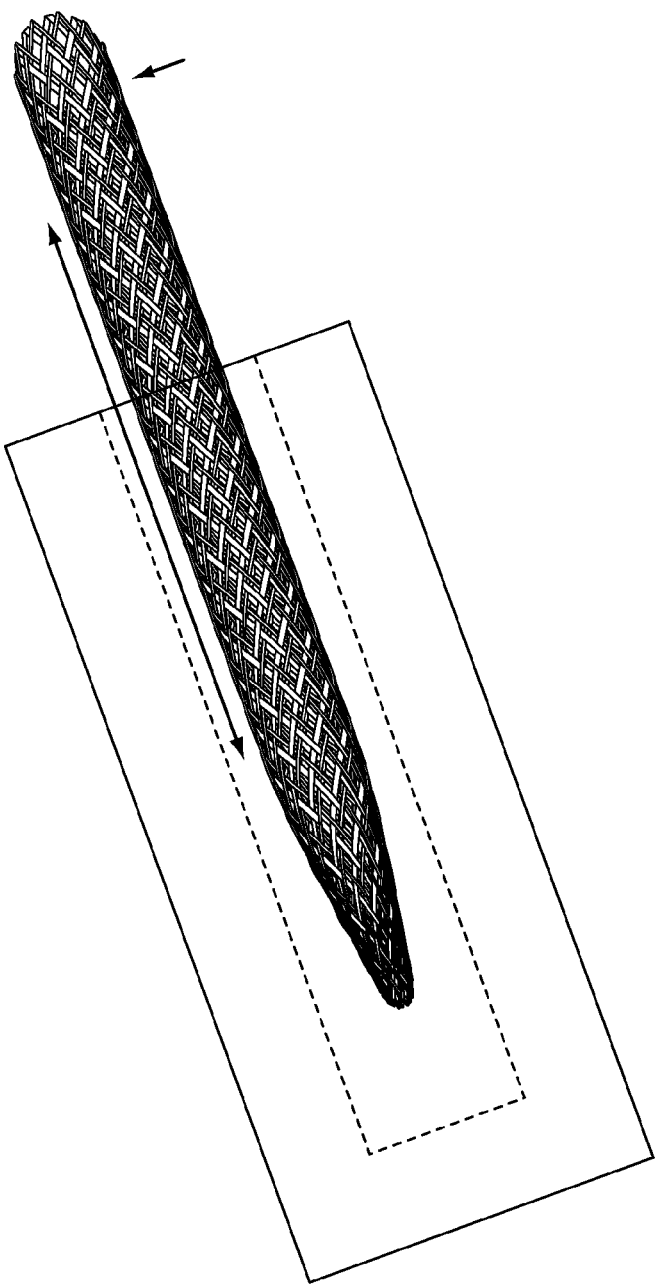
Figure 17G:
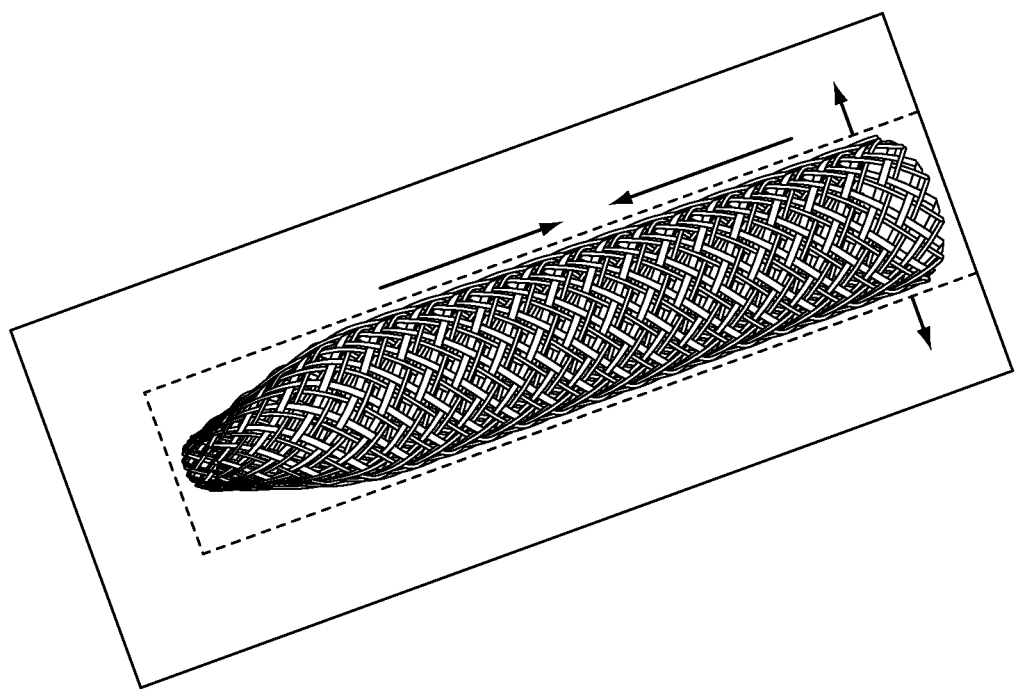

FIG. 17E shows a woven retention device 100 in a relaxed state. FIG. 17F shows that applying pressure in a longitudinal direction stretches the woven retention device 100 such that the diameter of the woven retention device 100 decreases. In this manner, the woven retention device 100 can be easily inserted into a bone hole 101. FIG. 17G shows that once inside the bone hole 101, the woven retention device 100 can have longitudinal forces applied to return the woven retention device 100 to a less constricted shape. In this manner, it allows for the woven retention device to snugly fit into the bone hole 101. In a relaxed state, the braid angles of the interwoven filaments can be larger than the braid angle in a construed or elongated state. In one embodiment, the retention device allows for a maximum distribution of protuberances based on the braid angle. Thus, the retention device 100 in the elongated state of FIG. 17F can have less distributed protuberances than the retention device 100 in the less constricted state of FIG. 178G.

Figure 18:
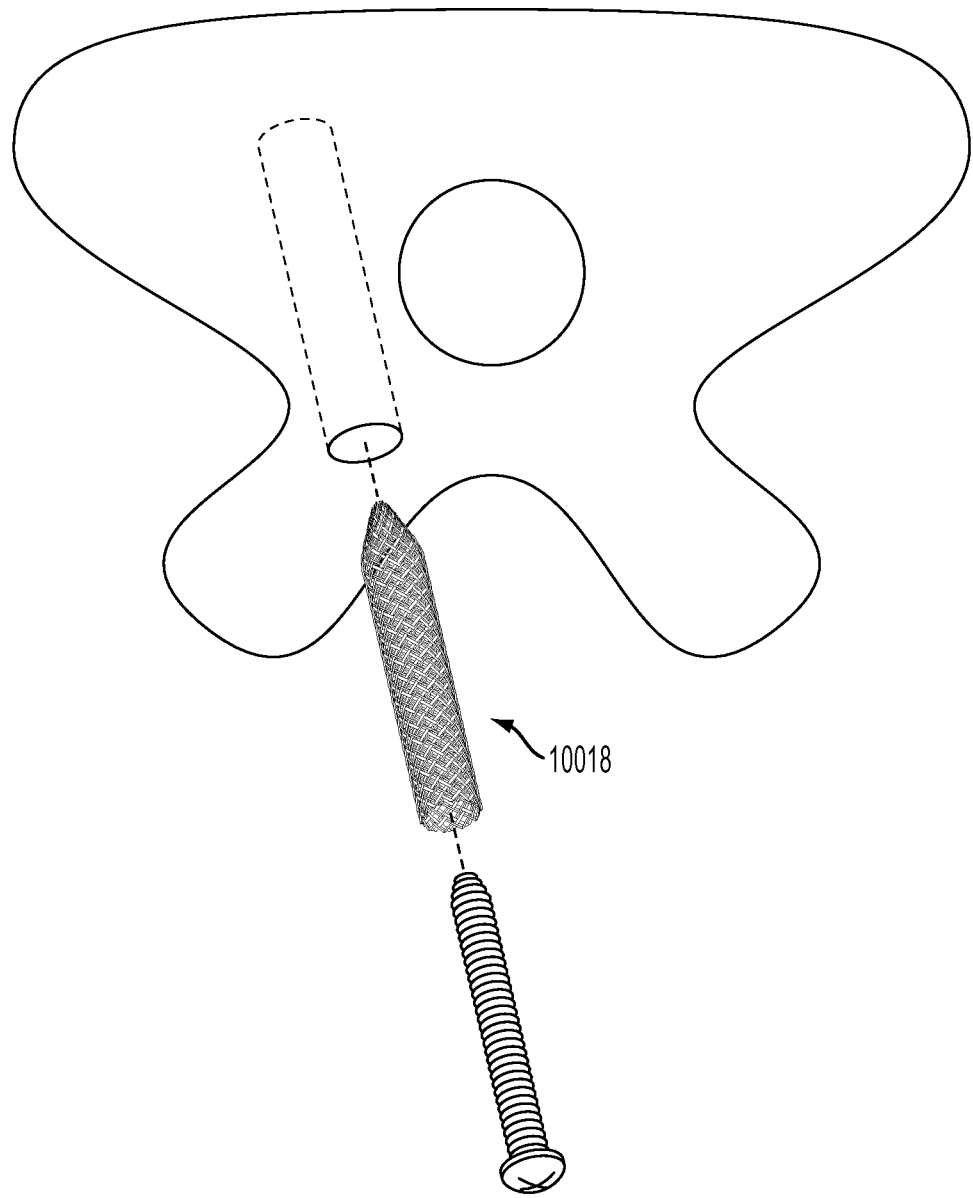
FIG. 18 shows an exploded view of a screw, a woven retention device and a pedicle hole, according to an embodiment of the present invention.

As can be seen from FIG. 18, a screw can be inserted into the woven retention device 10018, which can then be inserted into a hole in a vertebra. Embodiments of the invention are not limited to being used in any particular bone, and may be configured for use in any bone.

Figure 19:
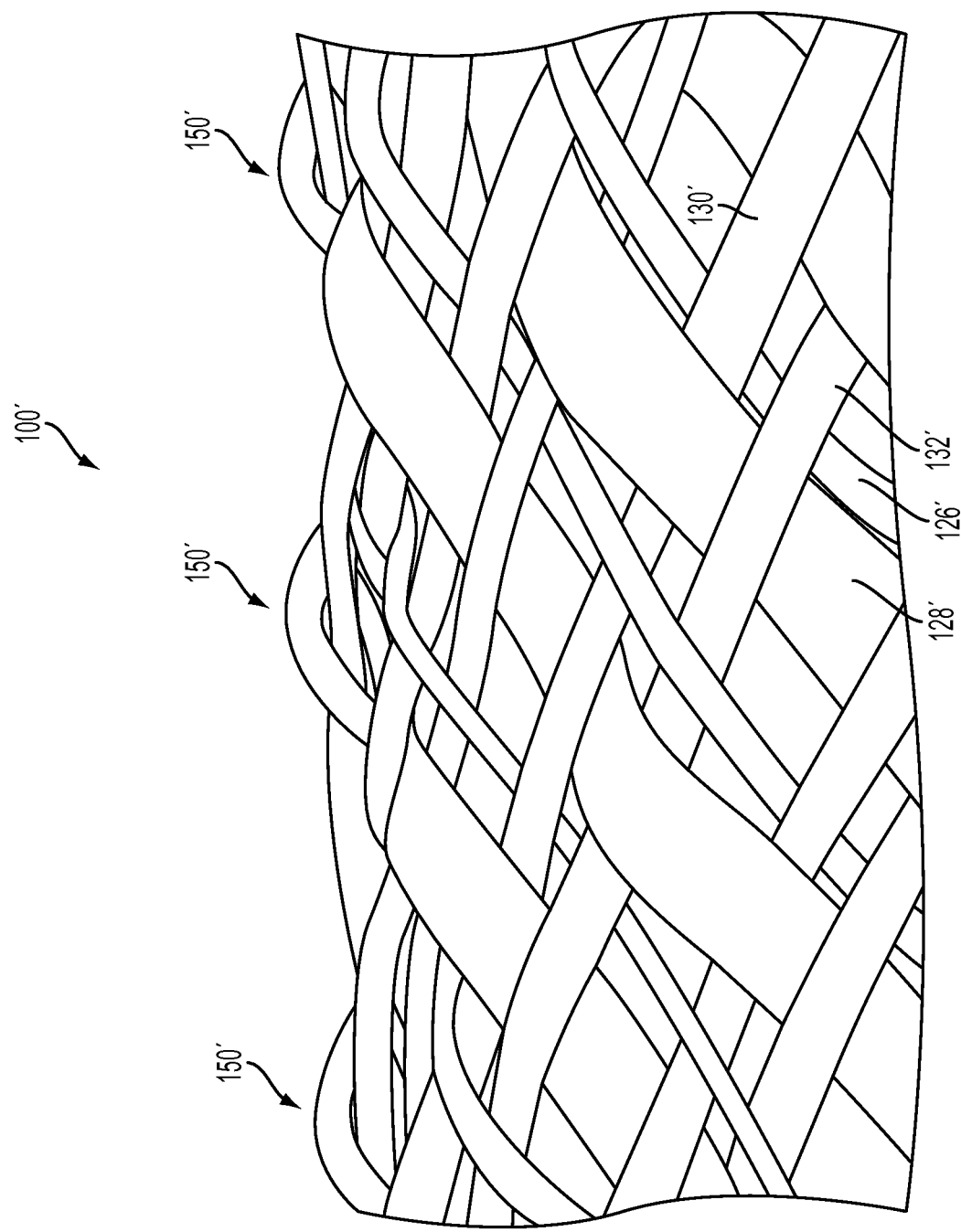
FIG. 19 shows a close-up perspective view of an exterior surface of the woven retention device according to an embodiment of the present invention.

FIG. 19 shows a perspective view of a portion of a woven retention device 100' according to an embodiment of the present invention. The profile of protuberances 150' are shown. According to this embodiment, the woven retention device 100' comprises a pair of monofilaments 126' and 132', and a pair of multifilaments 128' and 130'. In this example, each of the multifilaments 128' and 130' has a different width or linear mass thickness. Additionally, each of the monofilaments 126' and 132' have a different thickness. Specifically, multifilament 128' is wider than multifilament 130', and monofilament 132' is thicker than monofilament form 126'. However, the specific arrangement and relative thicknesses of the filaments in FIG. 19 are just examples of an embodiment. It should be understood that the monofilaments 126' and 132' may have the same or different relative thicknesses, and likewise for the widths or linear mass densities of multifilaments 128' and 130'.

Figure 20:
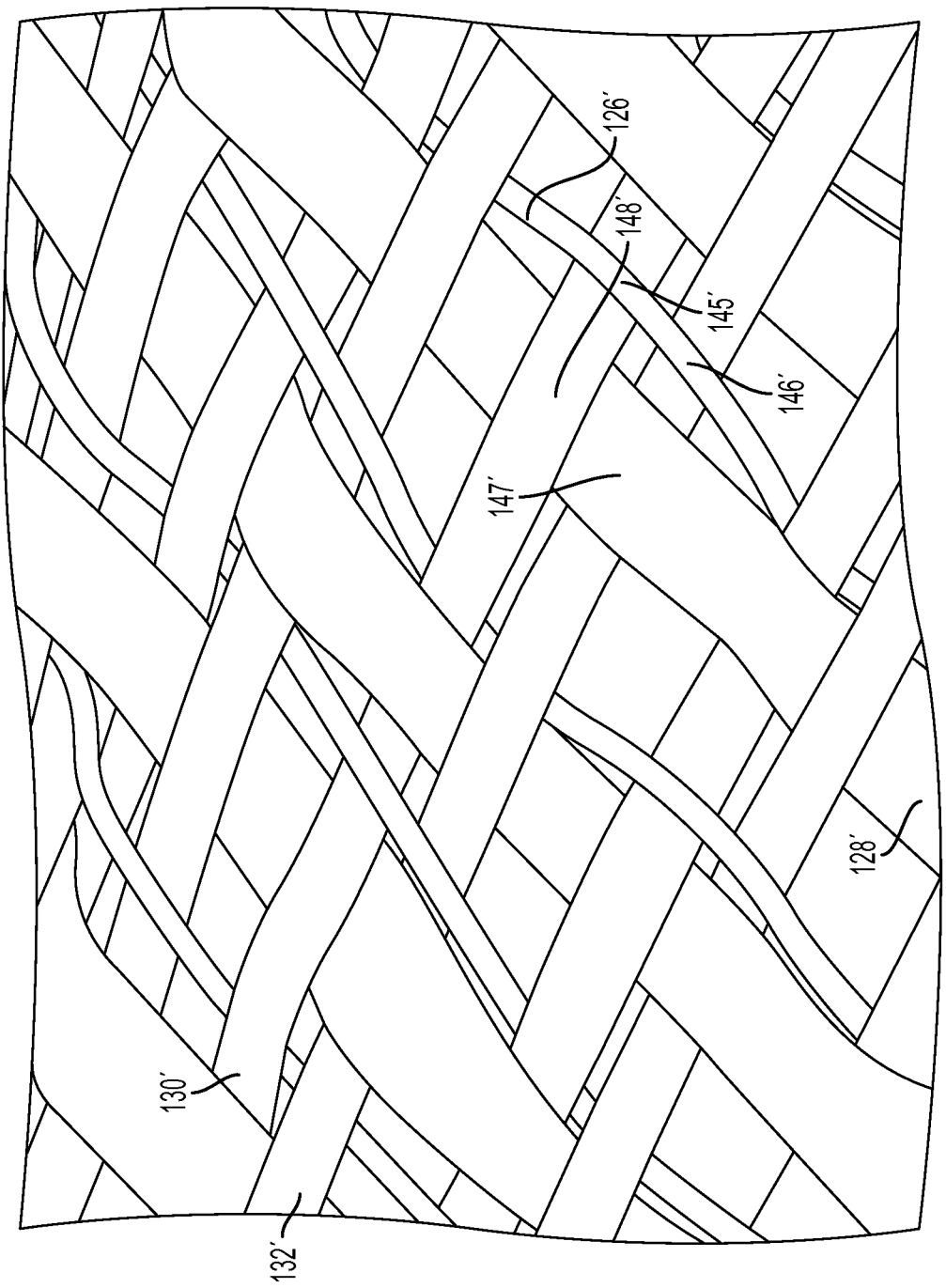
FIG. 20 shows a perspective view of a section of a woven retention device having differently-shaped diameters of monofilaments according to an embodiment of the present invention.

FIG. 20 shows another view of the embodiment shown in FIG. 19. The intersections of filaments 126', 128', 130', and 132' are shown to provide examples of the different types of intersections which can provide a plurality of combinations of filament cross-section geometries according to this embodiment. Specifically, intersection 145' represents the intersection of a monofilament 126' and multifilament 130'. Intersection 146' is the intersection of monofilament 126' and monofilament 132', which would represent the thickest protuberance according to this embodiment. Intersection 147' is the intersection of monofilament 132' and multifilament 128'. Finally, intersection 148' is the intersection of multifilament 130' and multifilament 128', which would form the smallest intersection thickness according to this embodiment. In the embodiment of FIG. 20, the plurality of plurality of filaments include thicker monofilaments (e.g., 132') wound in a first spiral direction of the woven retention device, and smaller monofilaments (e.g., 126') wound in a second spiral direction of the woven retention device.

Figure 21:
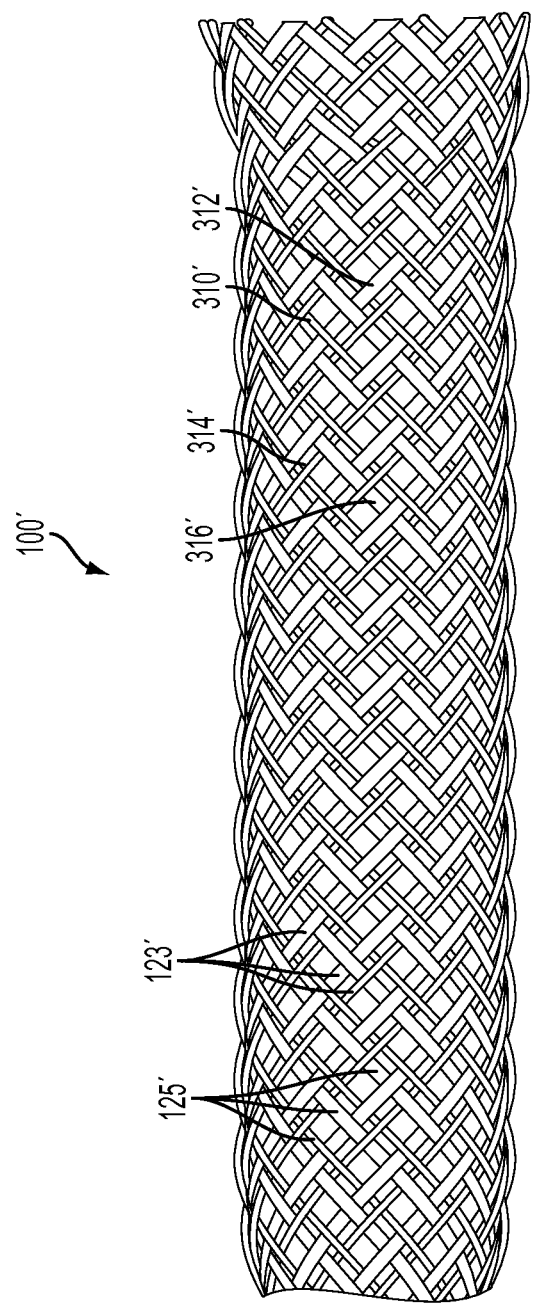
FIG. 21 shows a woven retention device having differently-shaped diameters of monofilaments according to an embodiment of the present invention.

FIG. 21 is a view of an embodiment of the woven retention device 100' shown in FIGS. 19 and 20. As shown, the first plurality of filaments 123', including monofilament 314' and multifilament 312', are wound in the first direction, and the second plurality of filaments 125', including monofilament 310' and multifilament 316', are wound in the second direction.

Figure 22:
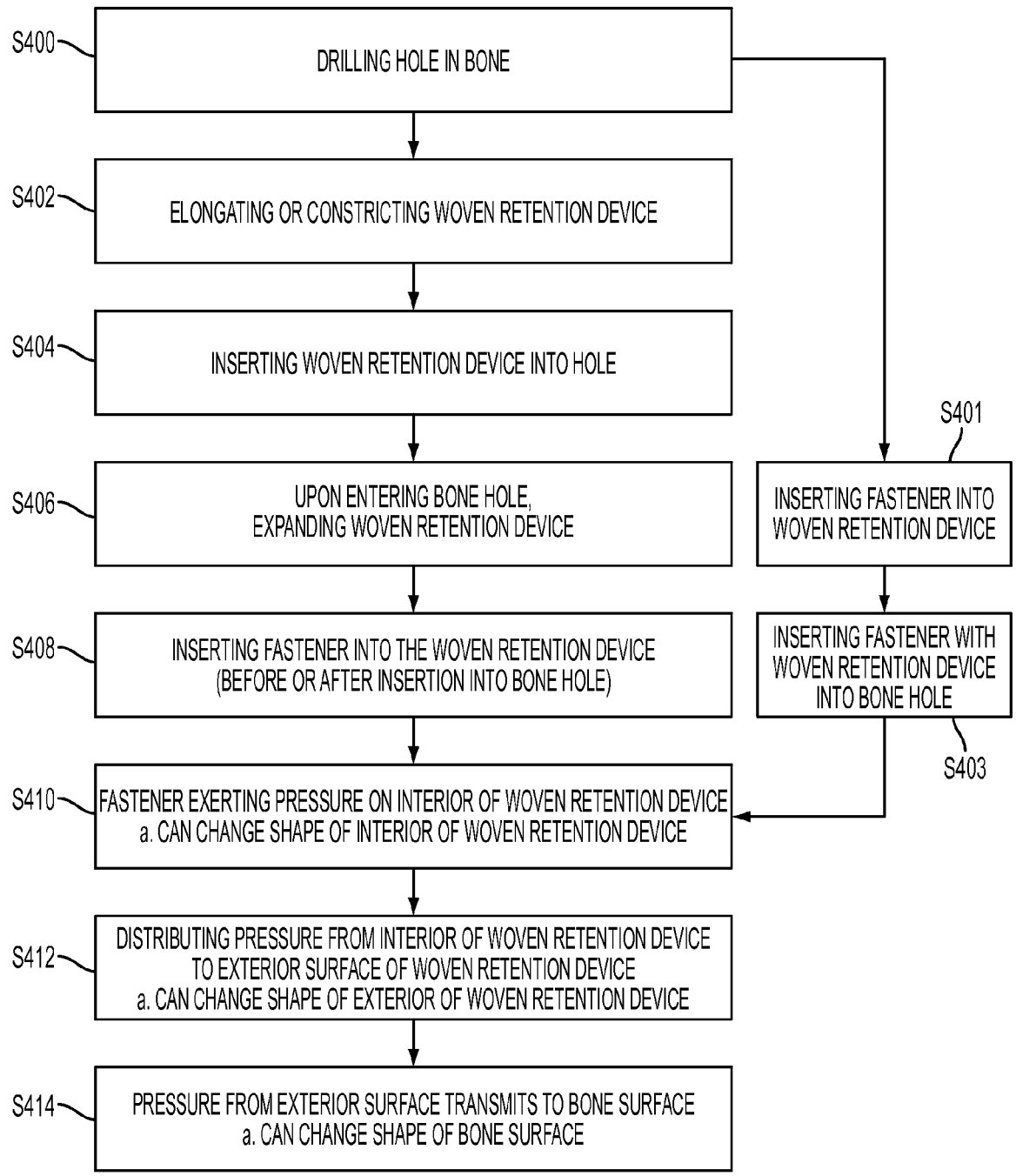
FIG. 22 shows a flow diagram of a method of utilizing a woven retention device in an embodiment, in accordance with the principles of the present invention.

Various methods of using the woven retention device can be used. FIG. 22 details steps that can be performed in conjunction with the woven retention device. The woven retention device may be inserted into a bone hole alone and then a fastener can be inserted. Alternatively, the woven retention device and screw can we combined prior to insertion and the combination inserted into the bone hole. The invention is not limited to the steps described in FIG. 22, is not limited to the order of the steps disclosed, and does not require that certain of the disclosed steps be performed.

In one embodiment, in step S400, a bone can be drilled to form a bone hole. In one embodiment, the woven retention device can be elongated or constricted in step S402, after which in step S404 the woven retention device can be inserted into the bone hole. After step S404, in step S406 the woven retention device upon entering the bone hole can be expanded. Thus, upon entering the bone hole, the woven retention device can expand to a less elongated and constricted state to interface with the bone surface. After step S406, in step S408 the fastener can be inserted into the woven retention device either before or after insertion into the bone hole. Next, the fastener can exert pressure on an interior of the woven retention device in step S410. In step S410, the fastener can optionally change the shape of the interior of the woven retention device. Next, in step S412, pressure from an interior of the woven retention device can be distributed to an exterior surface of the woven retention device. In step S412, the shape of the exterior surface of the woven retention device can optionally change shape. In step S414, pressure from an exterior surface of the woven retention device can transmit to bone surface. In step S414, the pressure transmission to the bone surface can optionally change the shape of the bone surface. In other embodiments, the steps can be performed in different orders or steps can be optionally omitted.

In another embodiment, instead of following steps S402, S404, S406 and S408, in step S401, a fastener can be inserted into the woven retention device before the woven retention device has been inserted into the bone hole, after which in step S403 the fastener with woven retention device can be inserted into the bone hole. After step S403, in step S410 the fastener can optionally change the shape of the interior of the woven retention device. Next, in step S412, pressure from an interior of the woven retention device can be distributed to an exterior surface of the woven retention device. In step S412, the shape of the exterior surface of the woven retention device can optionally change shape. In step S414, pressure from an exterior surface of the woven retention device can transmit to bone surface. In step S414, the pressure transmission to the bone surface can optionally change the shape of the bone surface.

In another embodiment, the distributing pressure step comprises dynamic micro-loading of the woven retention device based on differences in loading patterns of the woven retention device and the interfacing surface shape of the fastener. Based on a uniform radial distribution of the woven retention device, a different loading pattern, or in other words, a dynamic load, is possible. That is, instead of solely pushing or cutting bone, the fastener can deform the woven structure. Further, based on the flexibility of the weave, the woven retention device can facilitate an even distribution of load on uneven bone structure.

Thus, a fastener can be inserted into the woven retention device either before or after the woven retention device is inserted into the bone hole. Upon being inserted into the woven retention device, the fastener can exert a pressure on an interior surface of the woven retention device, which can optionally change the shape of the interior surface. The pressure exerted on the interior surface of the woven retention device can distribute pressure to an exterior surface of the woven retention device, which can optionally change the shape of the exterior surface. The change in the exterior surface can allow for better interfacing with the bone surface based on the changes to the exterior surface. The bone surface can optionally change shape based on the pressure that is applied by the woven retention device.

Figure 23:
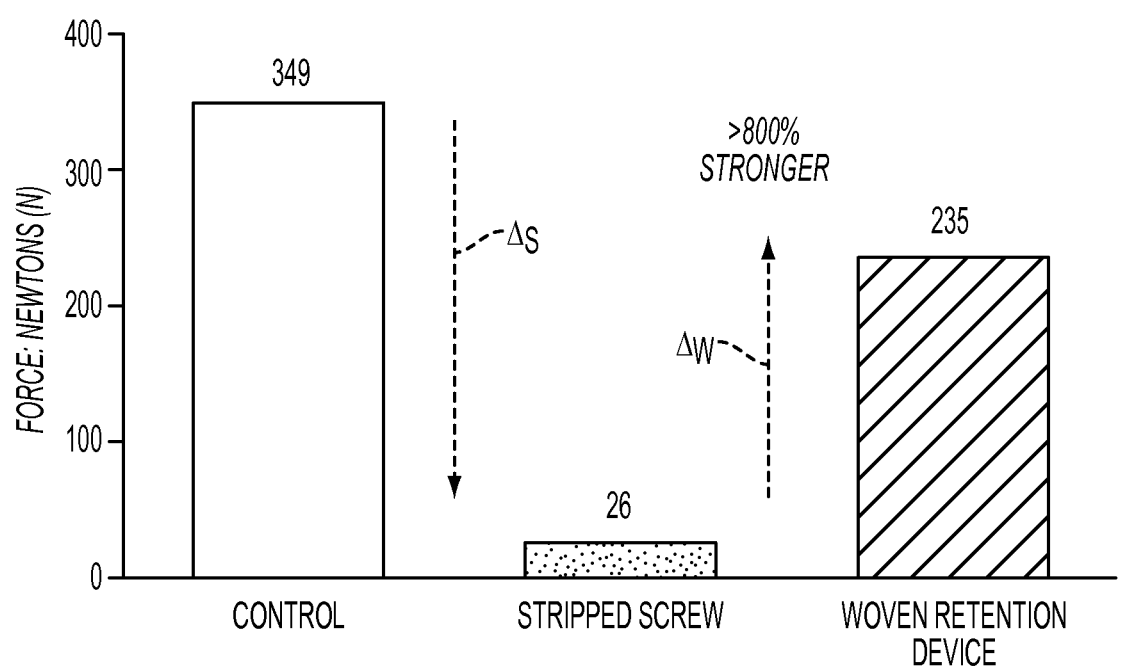
FIG. 23 shows a pullout strength comparison for a screw, a screw in a stripped bone hole, and a woven retention device with screw in a stripped bone hole, according to an example of an embodiment of the present invention.

FIG. 23 shows a graph of examples of pullout strengths of a screw in control bone hole, a screw in a stripped bone hole, and, according to an example of an embodiment of the invention, a screw in a woven retention device in a stripped bone hole. A stripped bone hole is one in which a screw, for one reason or another, has lost purchase or fit. For example, the bone may degrade or break to the point that the fit between the bone and the screw is lost, or part of the structure of the bone may be stripped or sheared by the screw itself, for example. As can be seen from FIG. 23, a screw in a stripped bone hole can cause a decrease $\Delta_S$ in the pullout strength of the screw as compared to a control screw that is in a bone hole that is not stripped. In addition, the woven retention device in accordance with the principles of the invention can cause an increase $\Delta_W$ in the force required to pullout the screw as compared to the screw by itself in a stripped hole. Although not shown in FIG. 23, the woven retention device can increase the pullout strength of the screw beyond that of a screw in a non-stripped hole, such as the control screw, including in cases where the woven retention device is used in conjunction with a screw in a non-stripped hole.

Figure 24:
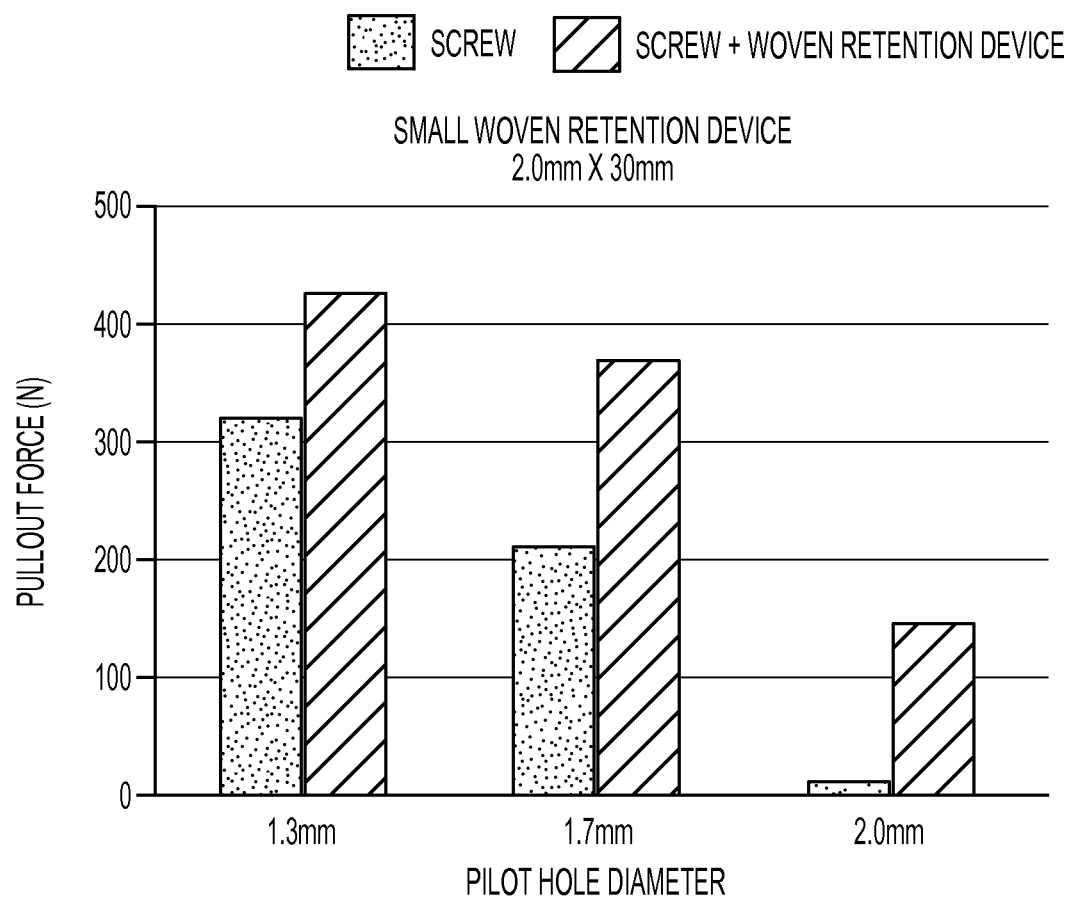
FIG. 24 shows a pullout force versus hole diameter for a screw and a screw with a woven retention device, in accordance with the principles of the present invention.

FIG. 24 shows a graph showing examples of different pullout forces between small screws in various different pilot holes. As can be seen from FIG. 24, the combination of the screw and woven fixation device, in accordance with the principles of the invention, has more pullout force in each of the tested sizes.

Figure 25:
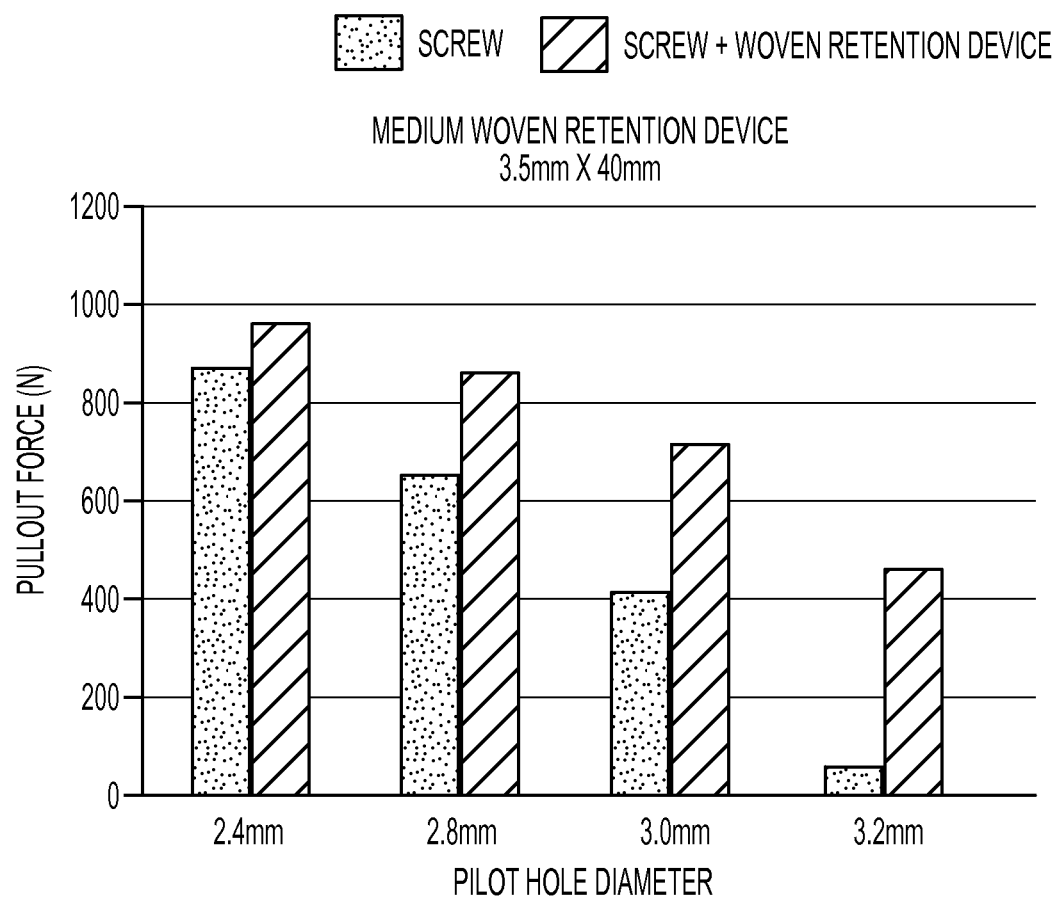
FIG. 25 shows another pullout force versus hole diameter for a screw and a screw with a woven retention device, in accordance with the principles of the present invention.

FIG. 25 shows a graph showing examples of different pullout forces between medium screws in various different pilot holes. As can be seen from FIG. 25, the combination of the screw and woven fixation device, in accordance with the principles of the invention, has more pullout force in each of the tested sizes.

Figure 26:
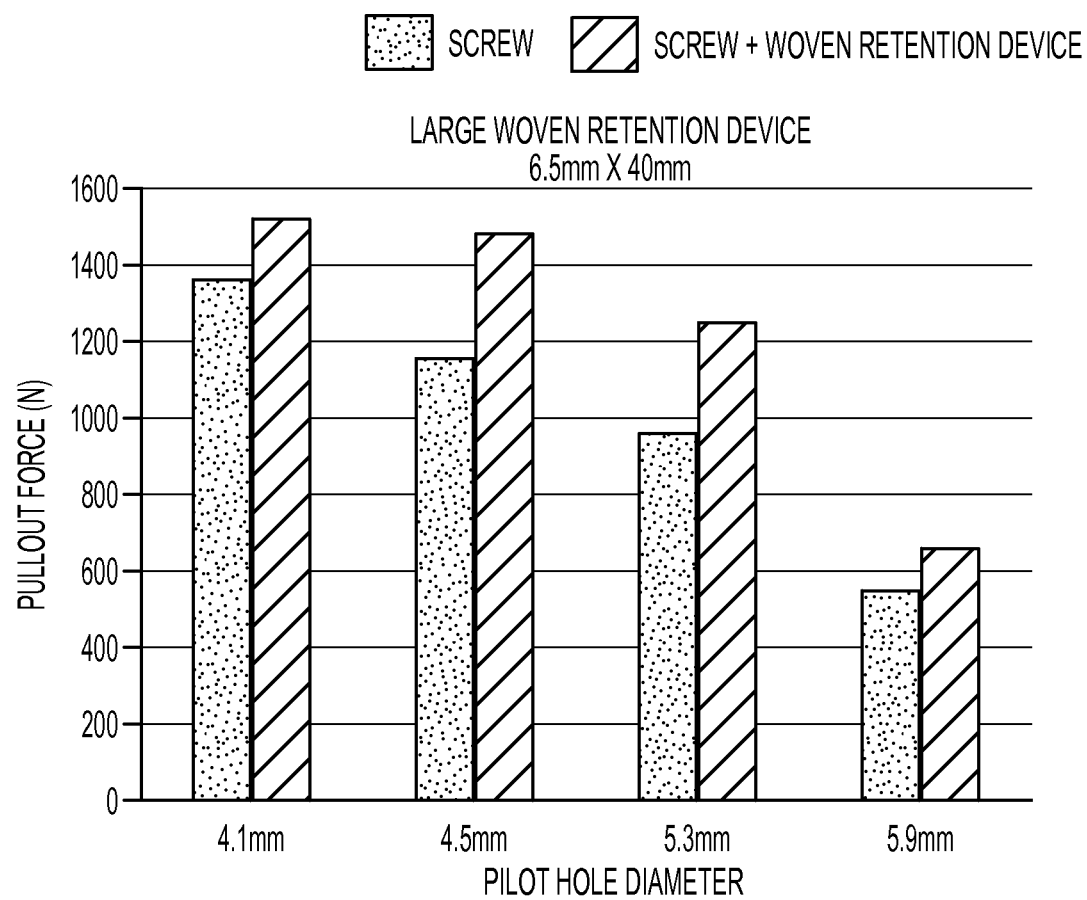
FIG. 26 shows another pullout force versus hole diameter for a screw and a screw with a woven retention device, in accordance with the principles of the present invention.

FIG. 26 shows a graph showing examples of different pullout forces between large screws in various different pilot holes. As can be seen from FIG. 26, the combination of the screw and woven fixation device, in accordance with the principles of the invention, has more pullout force in each of the tested sizes.

According to embodiments of the invention, the woven retention device can enhance pullout force percentage compared with a screw alone for a range of hole diameters. However, the woven retention device used with a small screw may allow for a higher percentage increase of pullout force than with medium and large screws. For example, the woven retention device according to an embodiment has been shown to add at least a 10% increase in pullout strength compared with the pullout force of a screw without a woven retention device. Specifically, for small hole diameters, the increase has been shown to be 33% to 77%, according to an example of one embodiment. For medium hole diameters, the increase has been shown to be 10% to 72%, according to another example of an embodiment. Finally, for large hole diameters, the increase has been shown to be 12% to 30% according to another example of an embodiment.

Examples of woven retention devices according to embodiments were fabricated using different combinations of filaments. Table 1 shows details of the four versions of these examples. Each version includes two types of counter clockwise filaments, and two types of clockwise filaments. "Type" refers to whether the filament is mono-filament or multi-filament. "Size" indicates the diameter (measured in millimeters) of the monofilaments, and the linear mass density (measured in decitex, or dtex, which is grams per 10,000 meters) for the multifilament. "# of Carriers" refers to the number of each filament. Version 1 is a combination of mono- and multifilaments. Version 2 is only monofilaments, where the monofilaments are all the same size. Version 3 is a combination of two different sizes of monofilaments. Version 4 is a combination of three different sizes of monofilaments. The woven retention devices in Versions 1-4 each had a braid angle of about 40° to 45°, and were sized to accommodate screw with an inner core diameter of about 6.5 mm (corresponding to the "large" size discussed above). The filaments were made of polyethylene terephthalate (PET).

TABLE 1

Examples of woven retention devices used for measuring pullout strength

| | Counter Clockwise Filaments | | | Clockwise Filaments | | |
|---|---|---|---|---|---|---|
| | Type | Size | # of Carriers | Type | Size | # of Carriers |
| Version 1 | mono | 0.2 mm | 12 | mono | 0.2 mm | 12 |
| | multi | flat 196 dtex | 12 | multi | flat 196 dtex | 12 |
| Version 2 | mono | 0.2 mm | 12 | mono | 0.2 mm | 12 |
| | mono | 0.2 mm | 12 | mono | 0.2 mm | 12 |
| Version 3 | mono | 0.2 mm | 12 | mono | 0.2 mm | 12 |
| | mono | 0.1 mm | 12 | mono | 0.1 mm | 12 |
| Version 4 | mono | 0.4 mm | 12 | mono | 0.2 mm | 12 |
| | mono | 0.1 mm | 12 | mono | 0.1 mm | 12 |

Figure 27:
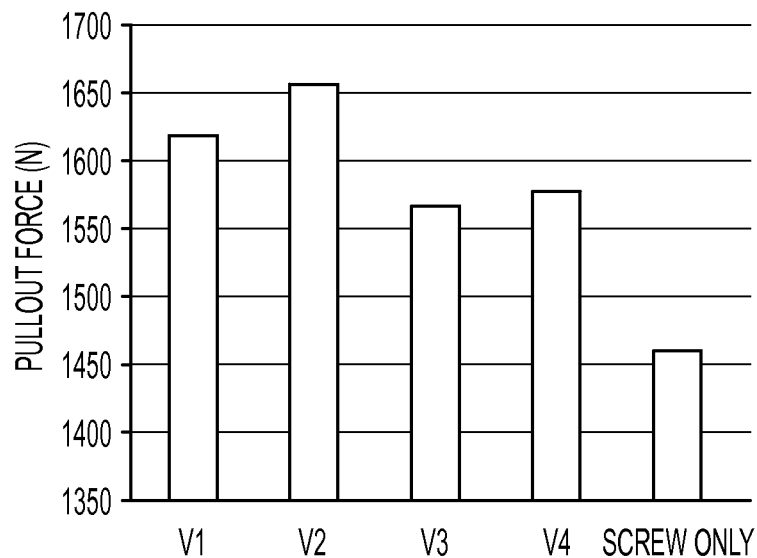
FIG. 27 shows pullout forces measured for woven retention devices of varying construction pulled from a first material, according to examples of embodiments of the present invention.
Figure 28:
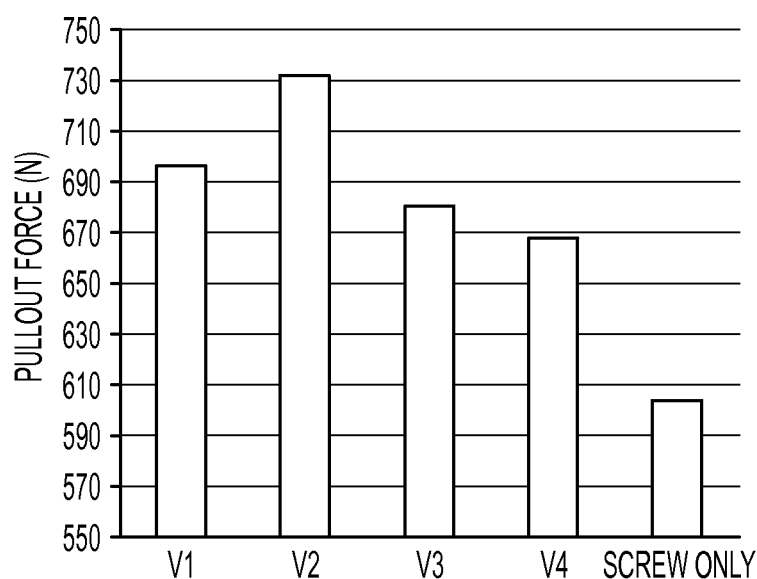
FIG. 28 shows pullout forces measured for woven retention devices of varying construction pulled from a second material, according to examples of embodiments of the present invention.

FIGS. 27 and 28 show the results of axial pullout strength using Versions 1-4 of the woven retention device in Table 1 as compared to the pullout strength of a screw without a woven retention device. Both tests used pilot holes with a diameter of 4.1 mm in polyurethane foam, and a screw with an inner core diameter of 6.5 mm and length of 40 mm. In the tests of FIG. 27, 15 pcf rigid polyurethane foam was used. In the tests of FIG. 28, 10 pcf rigid polyurethane foam was used. For all tests, the axial pullout strength was greater when a woven retention device was used, compared to when a screw was used without a woven retention device. Furthermore, FIGS. 27 and 28 show that the greatest pullout strength in these tests was achieved for Version 2, which comprised only monofilaments of the same size. Also, the percentage increase compared to screw-only pullout was greater in the less dense (10 pcf) polyurethane foam, indicating that embodiments of the present invention may well suited for lower density bone, such as osteoporotic or osteopenic bone, for example.

The woven retention device can be beneficial for use with low bone mineral density, which is the amount of mineral matter per square centimeter of bone that is between 1 and 2.5 standard deviations away from young normal adult. Low bone mineral density can include osteoporosis, osteopenia, hyperparathyroidism and/or osteomalacia. A notable part of the woven retention device's inner surface is its ability to engage with the screw without having a matching threaded surface on the interior in a preferred embodiment. The material of the woven retention device can be made of any plastic or fiber. Other materials can also be used, including metallic and natural or biological materials.

The dual interface can be achieved through having a tube-shaped, braided retention device with sufficient rigidity, stability (returning to the woven retention device's original shape or configuration after deformation), and tensile strength when a screw can be inserted to provide sufficient sheer strength to a screw on the one side and a uniform and distributed pressure to the bone on the other side. The woven retention device can have a multi-filament comprising a one-under/one-over arrangement of 45 degree angle intersections and a mono filament that runs adjacent to each of the braids such that each filament goes over two other filaments before going under two filaments (2-over/2-under, twill or herringbone). A three-under/three-over arrangement can also be possible. Other types of weaves are possible (including only a monofilament) as long as there can be sufficient stability, rigidity, compressibility, sheer strength, and/or tensile strength.

The Young's modulus (or load modulus) can also be used to quantify the woven retention device according to some embodiments. In one embodiment, there can be two portions associated with the response of the woven retention device shape upon exertion of pressure from the fastener and upon interfacing with the bony surface. For example, there can be a linear portion to the response curve (stress over strain curve), and there can be a non-linear portion where the material stops behaving elastically. If the material/structure exhibits the linear response over the range of the test (i.e., the amount of stretching performed on the sample), then the sample is "linear." The amount of stretching performed on the sample is typically an amount of stretching that the sample can be expected to experience in use because all samples will exhibit non-linear response eventually. If the sample exhibits the non-linear response within the test range, the sample can be "non-linear". In one embodiment, the Young's modulus of the woven retention device can be substantially linear over the load range of the fastener. In another embodiment, the Young's modulus of the woven retention device can be non-linear over the load range.

One configuration of the interlaced filaments can be at a 45 degree braid angle in relation to the axis of the retention device in the position after the woven retention device can be inserted into the hole. Such a braid angle allows for maximum distribution of the protuberances on the exterior surface of the tubular lattice. Other angles are also preferably contemplated to be between 40-50 degree braid angles relative to the retention device longitudinal axis. The woven retention device diameter can be dynamically determined depending on the size of pilot hole diameter such that braid angles are 45 degrees when in hole (which can be less critical for larger screws).

In one embodiment, the woven retention device can be shaped like a hollow rope. In another embodiment, the woven retention device does not require that the filaments be interwoven provided that other characteristics of the filaments provide for a sufficiently rigid and flexible lattice. For example, a retention device for interfacing with a bone surface can include a sleeve body comprising a plurality of intersecting filaments forming a substantially tubular wall, the tubular wall having an interior surface and an exterior surface, the sleeve body being configured to surround at least a portion of a fastener on an interior surface-side of the tubular wall. The retention device can also include a proximal end and a distal end, the sleeve body extending between the proximal and distal ends. The retention device can also include a plurality of protuberances distributed on the tubular wall, each of the plurality of protuberances being formed by intersecting two or more of the plurality of intersecting filaments.

In the retention device, the plurality of intersecting filaments can include a plurality of filament cross-section geometries. Further, the plurality of protuberances can have a plurality of protuberance thicknesses based on a plurality of combinations of the filament cross-section geometries, where a thickness of each of the plurality of protuberances can be based on a particular combination of the plurality of filament cross-section geometries at the intersection point, and the thickness being measured in a radial direction of the sleeve body. In the retention device, the sleeve body, when surrounding at least a portion of the fastener, can be configured to distribute pressure from the fastener on the interior surface-side of a protuberance to an exterior surface-side of two or more protuberances, and the plurality of protuberance thicknesses accommodate deviations in the bone surface. In an alternative configuration, the sleeve body can be configured to distribute pressure from the fastener on the interior surface side of a protuberance to an exterior surface-side of one protuberance having more than one force.

A retention device can include a substantially tubular lattice of intersecting fibers that can be configured to be inserted into a bone tunnel, the tubular lattice including a proximal end and a distal end, the proximal end having a receiving portion that can be configured to receive a fastener along a longitudinal axis of the retention device, wherein: the tubular lattice includes an inner surface that has a distributed interface with protruding and recessed portions that are configured to interact with an outer surface of the fastener, the tubular lattice includes an outer surface that has protruding and recessed multiple points of contact configured to interact with an interior bone surface, and the tubular lattice has a degree of stability that maintains a three-dimensional structure of the tubular lattice and has a degree of flexibility, the degree of stability and flexibility allowing for the distributed interface of the inner surface to distribute applied pressure to the protruding and recessed multiple points of contact of the outer surface, the pressure resulting from the fastener being inserted.

In some embodiments, the woven retention device can have the alternative or additional use of insulating surrounding biological tissue from the implanted device within the woven retention device. Some implantable devices, such as fasteners or screws, for example, can impinge on sensitive tissues or nerves. The woven retention device can ask as a barrier or cushion between the fastener, screw, or other device and the sensitive tissue. In particular, the woven retention device can shield the tissue or nerves from traumatic features of the fastener, such as sharp edges (e.g., screw threads) or pointed ends (e.g., the distal end of screws, nails, or other implantable devices).

In addition to acting as a physical barrier between tissue and the implanted device, the woven retention device according to some embodiments can provide other types of insulation for the biological tissue, including thermal insulation, for example. Certain materials, such as metal, can become heated when exposed to certain field or radiation, including those present in magnetic resonance imaging (MRI). If a patient undergoing MRI has implanted devices, those devices may become hot during the imaging, and pain or harm to the patient may result. Therefore, it is desirable to prevent pain and/or harm from such devices during these procedures. Accordingly, in a case where an implanted device may become heated, the woven retention device may insulate the tissue from that heat according to the physical structure and/or materials used in the woven retention device. For example, the filaments may be made of a material having low thermal conductance.

Although it is contemplated that embodiments of the present invention may be used in human subjects, embodiments are not limited to use in human bone and could be used in veterinary applications.

In describing embodiments, specific terminology is employed for the sake of clarity. However, the invention is not intended to be limited to the specific terminology and examples selected. A person skilled in the relevant art will recognize that other equivalent components can be employed and other methods developed without departing from the broad concepts of the current invention.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

I claim:

1. A woven retention device for interfacing with a bone surface, the retention device comprising:
a sleeve body comprising a plurality of sets of interwoven monofilaments that form a substantially tubular lattice with a plurality of protuberances distributed on an interior surface and an exterior surface of the tubular lattice at a predetermined spatial relationship, the plurality of sets of interwoven monofilaments having a plurality of different diameters, the sleeve body being configured to surround at least a portion of a fastener, wherein the plurality of protuberances being formed by intersection points of the plurality of sets of the interwoven monofilaments;
a proximal end that is proximal to the sleeve body and that is configured to receive at least a portion of the fastener; and
a distal end that is distal to the sleeve body,
wherein in a first, relaxed state, the sleeve body has a plurality of combinations of filament cross-section geometries at the intersection points, the plurality of combinations of filament cross-section geometries forming a plurality of different protuberance thicknesses, a thickness of each protuberance being measured in a radial direction of the sleeve body, and
wherein in a second state when a fastener is inserted into the tubular lattice, pressure from the fastener is transmitted to the tubular lattice such that the spatial relationship of the protuberances changes according to a function of bone density and according to a function of an interfacing surface shape of the fastener.

2. The retention device of claim 1, wherein:
the plurality of sets of interwoven monofilaments includes a first plurality of monofilaments that runs in a first helical direction and a second plurality of monofilaments that runs in a direction intersecting the first plurality of monofilaments, and
for each set of the first and second plurality of monofilaments, there is a substantially same arrangement of cross-section geometries at every other intersection along that set, the substantially same arrangement being different from an arrangement of cross-section geometries at remaining intersections along that set.

3. The retention device according to claim 1, wherein:
the distal end has a distal tip with a first diameter, and
the receiving portion has a second diameter that is greater than the first diameter.

4. The retention device of claim 2, further comprising a first plurality of multifilaments that runs in the first helical direction and a second plurality of multifilaments that runs in the second direction, the first plurality of monofilaments and the first plurality of multifilaments forming a first plurality of sets of filaments and the second plurality of monofilaments and the second plurality of multifilaments forming a second plurality of sets of filaments,
wherein each of the first plurality of sets of filaments comprises a first outer filament and a first inner filament, and each of the second plurality of sets of filaments comprises a second outer filament and a second inner filament.

5. The retention device of claim 4, wherein the first plurality of monofilaments are thinner in diameter than the second plurality of monofilaments.

6. The retention device of claim 5, wherein the plurality of interwoven filaments follow a two-under and two-over configuration, where at each intersection, the second plurality of monofilaments either overlies both of the intersecting monofilaments or is overlain by both of the intersecting monofilaments and the second plurality of monofilaments overlies one of the intersecting filaments and is overlain by the other of the intersecting filaments.

7. The retention device of claim 5, wherein the first plurality of monofilaments have a diameter in a range of about 0.1 mm-0.4 mm.

8. The retention device of claim 7, wherein the first plurality of monofilaments have a diameter of 0.2 mm.

9. The retention device of claim 1, wherein the plurality of interwoven filaments comprise a plurality of flat multifilaments.

10. The retention device of claim 1, wherein:
the interwoven filaments outline interstices that allow for bone ingrowth, and
the interstices formed by the intersecting filaments comprise differently shaped and differently sized interstices.

11. The retention device of claim 1, wherein the plurality of interwoven filaments are arranged in a two-under and two-over configuration.

12. The retention device of claim 1, wherein the plurality of interwoven filaments are arranged in a one-under and one-over configuration.

13. The retention device of claim 1, wherein the plurality of interwoven filaments are arranged in a two-over and one-under configuration.

14. The retention device of claim 1, wherein the plurality of interwoven filaments are arranged in a three-under and three-over configuration.

15. The retention device according to claim 1, wherein the fastener is a screw having a screw thread and the interior surface is configured to interact with the screw.

16. The retention device of claim 1, wherein the distal end is closed.

17. The retention device of claim 2, wherein in the relaxed state, the interwoven filaments extend around the tubular lattice at an angle of about 45 degrees with respect to a longitudinal direction of the woven retention device.

18. The retention device of claim 1, wherein the distributed protuberances are arranged in a diamond-shaped pattern grid.

19. The retention device of claim 1, wherein:
the tubular lattice has an outer radius spanning from a furthest outwardly extending protuberance in the radial direction on the exterior surface of the tubular lattice to a center point of the tubular lattice, the tubular lattice having an inner radius spanning from a furthest inwardly protruding protuberance in the axial direction on the interior surface of the tubular lattice to the center point of the tubular lattice, the tubular lattice having an average radius that is an average between the outer radius and the inner radius, and
wherein the outer radius of the tubular lattice is greatest at the intersection point of two of the thick monofilaments.

20. The retention device of claim 19, wherein the tubular lattice has an average diameter that is in a range of about 1.5 mm to 9.0 mm.

21. The retention device of claim 1, wherein the woven retention device has a length in a range from about 30 mm to 40 mm.

22. The retention device of claim 1, wherein when the fastener applies pressure to the inner surface, the pressure is transmitted to protuberances on the outer surface adjacent to the protuberance on the inner surface and configured to exert pressure on bone material.

23. The retention device of claim 1, further comprising the fastener.

24. The retention device of claim 1, wherein in the second state when the sleeve body distributes pressure from the fastener on the interior surface to the exterior surface, the fastener requires at least 10% more pullout force to pull the fastener out of the bone with the retention device than the pullout force required for a fastener in the bone hole without the retention device.

25. A retention device for interfacing with a bone surface, the retention device comprising:
a substantially tubular lattice of interwoven fibers that is configured to be inserted into a bone tunnel, the tubular lattice including a proximal end and a distal end, the proximal end having a receiving portion that is configured to receive a fastener along a longitudinal axis of the retention device,
wherein:
the tubular lattice includes an inner surface that has a spatially distributed interface with protruding and recessed portions that are configured to interact with an outer surface of the fastener, the tubular lattice includes an outer surface that has a spatially distributed interface with protruding and recessed multiple points of contact configured to interact with an interior bone surface, the protruding and recessed multiple points of contact being formed by intersecting points of the interwoven fibers and forming plurality of protruding and recessed points of contact, the interwoven fibers having a plurality of different diameters, the tubular lattice has a plurality of combinations of fiber cross-section geometries at the intersection points, a combination of the fibers cross-section geometries forming a plurality of different protruding and recessed portions thicknesses, a thickness of each protruding and recessed portion being measured in a radial direction of the sleeve body, and
the tubular lattice has a degree of stability that maintains a three-dimensional structure of the tubular lattice in a relaxed state and has a degree of flexibility, the degree of stability and flexibility allowing for the distributed interface of the inner surface to distribute applied pressure to the protruding and recessed multiple points of contact of the outer surface, such that a spatial relationship of the protruding and recessed portions changes according to a function of bone density and according to a function of an interfacing surface shape of the fastener.

26. The retention device of claim 25, wherein: the plurality of interwoven fibers includes sets of a first plurality of monofilaments that runs in a first helical direction and a second plurality of monofilaments that runs in a direction intersecting the first plurality of monofilaments, and for each set of the first and second plurality of monofilaments, there is a substantially same arrangement of cross-section geometries at every other intersection along that set, the substantially same arrangement being different from an arrangement of cross-section geometries at remaining intersections along that set.

27. The retention device of claim 26, wherein the first plurality of monofilaments are thinner in diameter than the second plurality of monofilaments.

28. The retention device of claim 27, wherein the first plurality of monofilaments have a diameter in a range of about 0.1 mm-0.4 mm.

29. The retention device according to claim 26, wherein:
the distal end has a distal tip with a first diameter, and
the receiving portion has a second diameter that is greater than the first diameter.

30. The retention device of claim 29, wherein the interwoven fibers follow a two-under and two-over configuration, where at each intersection, the second plurality of monofilaments either overlies both of the interwoven monofilaments or is overlain by both of the interwoven monofilaments and the second plurality of monofilaments overlies one of the interwoven filaments and is overlain by the other of the interwoven filaments.

31. The retention device of claim 25, wherein: the interwoven fibers outline interstices that allow for bone ingrowth, and the interstices formed by the intersecting fibers comprise differently shaped and differently sized interstices.

32. The retention device of claim 25, wherein in the relaxed state, the intersecting fibers extend around the tubular lattice at an angle of about 45 degrees with respect to a longitudinal direction of the woven retention device.

33. The retention device of claim 25, wherein: the tubular lattice has an outer radius spanning from a furthest outwardly extending protuberance in a radial direction on the exterior surface of the tubular lattice to a center point of the tubular lattice, the tubular lattice having an inner radius spanning from a furthest inwardly protruding protuberance in an axial direction on the interior surface of the tubular lattice to the center point of the tubular lattice, the tubular lattice having an average radius that is an average between the outer radius and the inner radius, and wherein the outer radius of the tubular lattice is greatest at the intersection point of two of the thick monofilaments.

34. The retention device of claim 25, wherein when the fastener applies pressure to the inner surface, the pressure is transmitted to protruding and recessed portions on the outer surface adjacent to the protruding and recessed portions on the inner surface and exerting pressure on bone material.

35. The retention device of claim 25, wherein in the second state when the sleeve body distributes pressure from the fastener on the interior surface to the exterior surface, the fastener requires at least 10% more pullout force to pull the fastener out of the bone with the retention device than the pullout force required for a fastener in the bone hole without the retention device.

* * * * *